(12) United States Patent
Dejohn et al.

(10) Patent No.: US 11,268,142 B2
(45) Date of Patent: *Mar. 8, 2022

(54) INTEGRATED DEVICE FOR NUCLEIC ACID DETECTION AND IDENTIFICATION

(71) Applicant: Mesa Biotech, Inc., San Diego, CA (US)

(72) Inventors: Marc Dejohn, Santa Fe, NM (US); Robert B. Cary, Santa Fe, NM (US); Nathan J. Cobb, Durham, NC (US)

(73) Assignee: Mesa Biotech, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/678,973

(22) Filed: Nov. 8, 2019

(65) Prior Publication Data

US 2020/0216876 A1 Jul. 9, 2020

Related U.S. Application Data

(63) Continuation of application No. 14/113,146, filed as application No. PCT/US2012/034596 on Apr. 20, 2012, now Pat. No. 10,519,492.

(Continued)

(51) Int. Cl.
*C12P 19/34* (2006.01)
*C12Q 1/686* (2018.01)
(Continued)

(52) U.S. Cl.
CPC ........ *C12Q 1/686* (2013.01); *B01L 3/502723* (2013.01); *C12P 19/34* (2013.01); *C12Q 1/6844* (2013.01)

(58) Field of Classification Search
CPC .................. C12Q 1/6844; B01L 3/502723
See application file for complete search history.

(56) References Cited

U.S. PATENT DOCUMENTS 3,667,607 A 6/1972 Brandt
4,235,601 A 11/1980 Deutsch et al.
(Continued)

FOREIGN PATENT DOCUMENTS

CN 1254844 A 5/2000
CN 1654214 A 8/2005
(Continued)

OTHER PUBLICATIONS

"Jikken Igaku Bessatsu Mokuteki De Eraberu PCR Jikken Protocol", Jan. 1, 2011, p. 50, Fig. 1B; p. 53, lines 1-12 (English translation of relevant passages attached).
(Continued)

*Primary Examiner* — Kenneth R Horlick
(74) *Attorney, Agent, or Firm* — BakerHostetler

(57) ABSTRACT

A disposable assay platform for detecting a target nucleic acid comprising multiple chambers and a method for operating the assay platform. Solutions containing the target nucleic acid move from one chamber to the next chamber by opening a vent pocket. The resulting pressure change enables the solution to flow to the next chamber. The platform comprises an electronic layer and one or more fluid layers bonded together. All heating operations can be performed by using resistive heating elements in the platform. All cooling operations are preferably passive. The platform is preferably operated when in a vertical orientation and can be docked to an external docking station that controls the operation of the platform.

19 Claims, 17 Drawing Sheets

Specification includes a Sequence Listing.

Related U.S. Application Data

(60) Provisional application No. 61/477,357, filed on Apr. 20, 2011, provisional application No. 61/477,437, filed on Apr. 20, 2011.

(51) Int. Cl.
  *C12Q 1/6844* (2018.01)
  *B01L 3/00* (2006.01)

(56) References Cited

U.S. PATENT DOCUMENTS

| | | | |
|---|---|---|---|
| 4,663,277 A | 5/1987 | Wang | |
| 4,683,195 A | 7/1987 | Mullis et al. | |
| 4,683,202 A | 7/1987 | Mullis | |
| 4,800,159 A | 1/1989 | Mullis et al. | |
| 4,960,691 A | 10/1990 | Gordon et al. | |
| 5,225,163 A | 7/1993 | Andrews | |
| 5,354,538 A | 10/1994 | Bunce et al. | |
| 5,514,785 A | 5/1996 | Van Ness et al. | |
| 5,516,664 A | 5/1996 | Hyman | |
| 5,578,467 A | 11/1996 | Schuster et al. | |
| 5,618,494 A | 4/1997 | Bunce et al. | |
| 5,716,819 A | 2/1998 | Chatterjee | |
| 5,736,188 A | 4/1998 | Alcock et al. | |
| 5,741,647 A | 4/1998 | Tam | |
| 5,922,617 A | 7/1999 | Wang et al. | |
| 6,007,999 A | 12/1999 | Clark | |
| 6,037,127 A | 3/2000 | Ebersole et al. | |
| 6,083,502 A | 7/2000 | Pastan et al. | |
| 6,146,589 A | 11/2000 | Chandler | |
| 6,190,612 B1 | 2/2001 | Berger et al. | |
| 6,214,587 B1 | 4/2001 | Dattagupta et al. | |
| 6,261,779 B1 | 7/2001 | Barbera-Guillem et al. | |
| 6,300,069 B1 | 10/2001 | Missel et al. | |
| 6,335,205 B1 | 1/2002 | Bausback | |
| 6,468,749 B1 | 10/2002 | Ulanovsky et al. | |
| 6,471,916 B1 | 10/2002 | Noblett | |
| 6,555,349 B1 | 4/2003 | O'Donnell | |
| 6,743,399 B1 | 6/2004 | Weigl et al. | |
| 7,094,536 B2 | 8/2006 | Kurn | |
| 7,159,618 B2 | 1/2007 | Broyer et al. | |
| 7,186,508 B2 | 3/2007 | Lee et al. | |
| 7,195,872 B2 | 3/2007 | Agrawal et al. | |
| 7,273,590 B2 | 9/2007 | Yao et al. | |
| 8,173,078 B2 | 5/2012 | Yao et al. | |
| 8,980,561 B1 | 3/2015 | Cai et al. | |
| 9,207,236 B2 | 12/2015 | Cary | |
| 9,354,199 B2 | 5/2016 | Selden et al. | |
| 9,428,781 B2 | 8/2016 | Cai et al. | |
| 9,678,065 B2 * | 6/2017 | Sugarman | G01N 33/56988 |
| 9,731,297 B2 | 8/2017 | Glezer et al. | |
| 9,944,922 B2 | 4/2018 | Cary | |
| 10,316,358 B2 | 6/2019 | Cary | |
| 10,458,978 B2 | 10/2019 | Cary | |
| 10,519,492 B2 | 12/2019 | Cary | |
| 2001/0019825 A1 | 9/2001 | Lee et al. | |
| 2002/0028475 A1 | 3/2002 | Ligler et al. | |
| 2002/0058252 A1 | 5/2002 | Ananiev | |
| 2002/0076825 A1 | 6/2002 | Cheng et al. | |
| 2002/0127574 A1 | 9/2002 | Mirkin et al. | |
| 2002/0172969 A1 | 11/2002 | Burns et al. | |
| 2002/0177135 A1 | 11/2002 | Doung et al. | |
| 2002/0179445 A1 | 12/2002 | Alajoki et al. | |
| 2002/0192839 A1 | 12/2002 | Mink et al. | |
| 2003/0003514 A1 | 1/2003 | Kovalenko | |
| 2003/0008308 A1 | 1/2003 | Enzelberger et al. | |
| 2003/0044862 A1 | 3/2003 | Giaccia et al. | |
| 2003/0054176 A1 | 3/2003 | Pantano et al. | |
| 2003/0064364 A1 | 4/2003 | Lockhart et al. | |
| 2003/0100128 A1 | 5/2003 | Kenjyou et al. | |
| 2003/0170686 A1 | 9/2003 | Hoet et al. | |
| 2003/0190608 A1 | 10/2003 | Blackburn | |
| 2004/0029177 A1 | 2/2004 | Nadaoka et al. | |
| 2004/0053256 A1 | 3/2004 | Lee et al. | |
| 2004/0058378 A1 | 3/2004 | Kong et al. | |
| 2004/0086897 A1 | 5/2004 | Mirkin et al. |
| 2004/0110167 A1 | 6/2004 | Gerdes et al. |
| 2004/0152122 A1 | 8/2004 | Hwang et al. |
| 2004/0209309 A1 | 10/2004 | Muldoon et al. |
| 2005/0014192 A1 | 1/2005 | Kurn |
| 2005/0032729 A1 | 2/2005 | Shyamala |
| 2005/0032730 A1 | 2/2005 | Von Der Mulbe et al. |
| 2005/0042627 A1 | 2/2005 | Chakrabarti et al. |
| 2005/0047972 A1 | 3/2005 | Lauks et al. |
| 2005/0079492 A1 | 4/2005 | Burgess, Jr. et al. |
| 2005/0112780 A1 | 5/2005 | Song |
| 2005/0136443 A1 | 6/2005 | Shigemori |
| 2005/0221281 A1 | 10/2005 | Ho et al. |
| 2005/0227275 A1 | 10/2005 | Jung et al. |
| 2005/0243321 A1 | 11/2005 | Cohen et al. |
| 2005/0250141 A1 | 11/2005 | Lambert et al. |
| 2006/0024813 A1 | 2/2006 | Warthoe |
| 2006/0041058 A1 | 2/2006 | Yin et al. |
| 2006/0127886 A1 | 6/2006 | Kaylor et al. |
| 2006/0154286 A1 | 7/2006 | Kong et al. |
| 2006/0160078 A1 | 7/2006 | Cardy et al. |
| 2006/0177873 A1 | 8/2006 | Dowd |
| 2006/0239859 A1 | 10/2006 | Ohman et al. |
| 2006/0246601 A1 | 11/2006 | Song et al. |
| 2006/0286570 A1 | 12/2006 | Rowlen et al. |
| 2007/0015166 A1 | 1/2007 | Nilsen |
| 2007/0020768 A1 | 1/2007 | Rundstrom et al. |
| 2007/0039835 A1 | 2/2007 | Rossier et al. |
| 2007/0231798 A1 | 10/2007 | Collins |
| 2008/0124720 A1 | 5/2008 | Sowerby et al. |
| 2008/0145835 A1 | 6/2008 | Alajem et al. |
| 2008/0207892 A1 | 8/2008 | Iwaki |
| 2008/0280285 A1 | 11/2008 | Chen et al. |
| 2009/0047673 A1 | 2/2009 | Cary |
| 2009/0053106 A1 | 2/2009 | Wu et al. |
| 2009/0130719 A1 | 5/2009 | Handigue |
| 2009/0181411 A1 | 7/2009 | Battrell et al. |
| 2009/0186357 A1 | 7/2009 | Mauk et al. |
| 2009/0246782 A1 | 10/2009 | Kelso et al. |
| 2010/0203532 A1 | 8/2010 | Makrigiorgos |
| 2010/0248273 A1 | 9/2010 | Campbell et al. |
| 2010/0276005 A1 | 11/2010 | Allain et al. |
| 2011/0039261 A1 | 2/2011 | Hillebrand et al. |
| 2011/0117540 A1 | 5/2011 | Cary |
| 2011/0160090 A1 | 6/2011 | Cary |
| 2014/0045191 A1 | 2/2014 | DeJohn et al. |
| 2014/0141484 A1 | 5/2014 | Campbell et al. |
| 2015/0184255 A1 | 7/2015 | Cai et al. |
| 2016/0083716 A1 | 3/2016 | Cary |
| 2016/0222442 A1 | 8/2016 | Cary |
| 2016/0310948 A1 | 10/2016 | Nowakowski et al. |
| 2016/0362725 A1 | 12/2016 | Cai et al. |
| 2017/0160271 A1 | 6/2017 | Cary |
| 2017/0233794 A1 | 8/2017 | Cai et al. |
| 2018/0304260 A1 | 10/2018 | Thomas et al. |
| 2019/0330681 A1 | 10/2019 | Cai et al. |

FOREIGN PATENT DOCUMENTS

| | | |
|---|---|---|
| CN | 1954214 A | 4/2007 |
| CN | 10140993 A | 4/2009 |
| EP | 0805215 A2 | 5/1997 |
| EP | 1972938 A1 | 9/2008 |
| GB | 2261284 A | 5/1993 |
| JP | 05240872 | 9/1993 |
| JP | 2001518614 A | 10/2001 |
| JP | 2005185972 A | 7/2005 |
| JP | 2005532827 | 11/2005 |
| JP | 2006520190 A | 9/2006 |
| JP | 2007503958 A | 3/2007 |
| JP | 2008521432 A | 6/2008 |
| JP | 2009100761 A | 5/2009 |
| WO | WO199423055 A1 | 10/1994 |
| WO | WO1997003207 A1 | 1/1997 |
| WO | WO200029112 A1 | 5/2000 |
| WO | WO2004007078 A1 | 1/2004 |
| WO | WO2004090555 A1 | 10/2004 |
| WO | WO2004092342 A2 | 10/2004 |
| WO | WO2005098439 A2 | 10/2005 |

(56) References Cited

FOREIGN PATENT DOCUMENTS

| | | |
|---|---|---|
| WO | WO2006059911 A1 | 6/2006 |
| WO | WO2006098804 A2 | 9/2006 |
| WO | WO2006122311 A2 | 11/2006 |
| WO | WO2007030505 A1 | 3/2007 |
| WO | WO2007083388 A1 | 7/2007 |
| WO | WO2008105814 A2 | 9/2008 |
| WO | WO2009103843 A2 | 8/2009 |
| WO | WO2009137059 A2 | 11/2009 |
| WO | WO2010037012 A2 | 4/2010 |
| WO | WO2010105074 A1 | 9/2010 |
| WO | WO2011087813 A2 | 7/2011 |
| WO | WO2012083189 A2 | 6/2012 |
| WO | WO2012145725 A2 | 10/2012 |
| WO | WO2012145730 A2 | 10/2012 |

OTHER PUBLICATIONS

Kodak DCS Quick Start Guide, 2005, 2 pages.
NanoComposix [retrieved on Jul. 27, 2017-07-27]: retrieved from the Internet: <URL: nanocomposix.com/pages/gold-colloid>, 2014.
PCR Amplification, Protocols and Applications Guide, https:/lwww.promega.ca/resources/product-guides-and-,electors/protocols-and-applicati Jns-guide/pcr-amplification/, 2016.
Akane, Atsushi et al., "Identification of the Heme Compound Copurified with Deoxyribonucleic Acid (DNA) from Bloodstains, a Major Inhibitor of Polymerase Chain Reaction (PCR) Amplification1", Journal of Forensic Sciences, vol. 39, No. 2, ASTM Internationa, Mar. 1994, 362-372.
Albretsen, Catrine et al., "Optimal Conditions for Hybridization with Oligonucleotides: A Study with myc-Oncogene DNA Probes", Analytical Biochemistry, vol. 170, Academic Press, Inc., 1988, 193-202.
Al-Soud, et al., "Effects of Amplification Facilitators on Diagnostic PCR in the Presence of Blood, Feces, and Meat", Feb. 2000, 4463-4470.
An, Lixin et al., "Characterization of a Thermostable UvrD Helicase and Its Participation in Helicase-dependent Amplification", The Journal of Biological Chemistry, vol. 280, No. 32, American Society for Biochemistry and Molecular Biology, Inc., Aug. 12, 2005, 28952-28958.
Andreotti, Peter E. et al., "Immunoassay of infectious agents", BioTechniques Euro Edition, vol. 35, No. 4, Oct. 2003, 850-859.
Ausbel, et al., "Current Protocols in Molecular Biology", John Wiley & Sons, Inc., 1992, 15.6.1-15.6.4.
Aveyard, et al., "One step visual detection of PCR products with gold nanoparticles and a nucleic acid lateral flow (NALF) device", Chem. Commun., 2007, 4251-4253.
Baeumner, Antje J., "Biosensors for environmental pollutants and food contaminants", Anal Bioanal Chem, vol. 377, 2003, 434-445.
Baeumner, Antje J. et al., "A rapid biosensor for viable B. anthracis spores", Anal. Bioanal. Chem., vol. 380, 2004, 15-23.
Baeumner, Antje J. et al., "A Universal Nucleic Acid Sequence Biosensor with Nanomolar Detection Limits", Analytical Chemistry, vol. 76, No. 4, American Chemical Society, Feb. 15, 2004, 888-894.
Baeumner, Antje J. et al., "Biosensor for Dengue Virus Detection: Sensitive, Rapid, and Serotype Specific", Analytical Chemistry, vol. 74, No. 6, American Chemical Society, Mar. 15, 2002, 1442-1448.
Barany, Francis, "The Ligase Chain Reaction in a PCR World", Genome Research, vol. 1, Cold Spring Harbor Laboratory Press, Aug. 1991, 5-16.
Barnes, "PCR amplification of up to 35-kb DNA with high fidelity and high yield from A bacteriophage templates", Proc. Natl. Acad. Sci., vol. 91, Mar. 1994, 2216-2220.
Baskaran, et al., "Uniform Amplification of a Mixture of Deoxyribonucleic Acids with Varying GC Content", Genome Research, Jul. 1996, 633-638.
Berthelet, Marc et al., "Rapid, direct extraction of DNA from soild for PCR analysis using polyvinylpyrrolidone spin columns", FEMS Microbiology Letter, vol. 138, Federation of European Microbiological Societies, 1996, 17-22.

Biagini, Raymond E. et al., "Rapid, Sensitive, and Specific Lateral-Flow Immunochromatographic Device to Measure Anti-Anthrax Protective Antigen Immunoglobulin G in Serum and Whole Blood", Clinical and Vaccine Immunology, vol. 13, No. 5, May 2006, 541-546.
Blake, R. D. et al., "Thermodynamic effects of formamide on DNa stability", Nucleic Acids Research, vol. 24, No. 11, Oxford University Press, 1996, 2095-2103.
Boom, R. et al., "Rapid and Simple Method for Purification of Nucleic Acids", Journal of Clinical Microbiology, vol. 28, No. 3, American Society for Microbiology, Mar. 1990, 495-503.
Boom, R. et al., "Rapid Purification of Hepatitis B Virus DNA from Serum", Journal of Clinical Microbiology, vol. 29, No. 9, American Society for Microbiology, Sep. 1991, 1804-1811.
Braasch, Dwaine A. et al., "Locked nucleic acid (LNA): fine-tuning the recognition of DNa and RNA", Chemistry & Biology, vol. 8, Elsevier Science Ltd., 2001, 731-735.
Braun, et al., "Exponential DNA Replication by Laminar Convection", Physical Review Letters, Oct. 10, 2003, 158103-1-158103-4.
Bright, Rick A. et al., "Incidence of adamantane resistance among influenza A (H3N2) viruses isolated worldwide from 1994 to 2005: a cause for concern", Lancet, vol. 366, Sep. 22, 2005, 1175-1181.
Brlansky, R. H. et al., "Colonization of the Sharpshooter Vectors, Oncometopia nigricans and Homalodisca coagulata, by Xylem-LOimited Bacteria", Phytopathology, vol. 73, No. 4, The American Phytopathological Society, 1983, 530.535.
Brlansky, R. H. et al., "Transmission of the Citrus Variegated Chlorosis Bacterium Xylella fastidiosa with the Sharpshooter Oncometopia nigricans", Plant Disease, vol. 86, No. 11, American Phytopathological Society, Nov. 2002, 1237-1239.
Buck et al., Design Strategies and Performance of Custom DNA Sequencing Primers, BioTechniques 27:528-536 (Sep. 1999).
Buhro, William E. et al., "Semiconductor nanocrystals: Shapematters", Nature Materials, vol. 2, No. 3, Nature Publishing Group, Mar. 2003, 138-139.
Burns, et al., "An Integrated Nanoliter DNA Analysis Device", Science, Oct. 16, 1998, 484-487.
Cai, et al., "Oscillating Amplification Reaction for Nucleic Acids", U.S. Appl. No. 61/477,437, filed Apr. 20, 2011.
Capaldi, Stephen et al., "Signal amplification through nucleotide extension and excision on a dendritic DNA platform", Nucleic Acids Research, vol. 28, No. 7, Oxford University Press, 2000, i-vii.
Carney, et al., "Present and future applications of gold in rapid assays", IVD Technology, Mar. 1, 2006, 1-8.
Carter, Darren J. et al., "Lateral flow microarrays: a novel platform for rapid nucleic acid detection based on miniaturized lateral flow chromatography", Nucleic Acids Research, vol. 35, No. 10, 2007, 1-11.
Caruthers, Jonathan M. et al., "Helicase structure and mechanism", Curr Opin Struc Biol, vol. 12, 2002, 123-133.
Cary, "An Integrated Low Cost Nucleic Acid Analysis Platform for the Rapid Detection of Plan Pathogens", Jan. 6, 2011.
Chang, Chung J. et al., "Culture and Serological Detection of the Xylem-Limited Bacterium Causing Citrus Variegated Chlorosis and Its Identification as a Strain of Xylella fastidiosa", Current Microbiology, vol. 27, Springer-Verlag New York, Inc., 1993, 137-142.
Chanteau, Suzanne et al., "Early diagnosis of bubonic plague using F1 antigen capture ELISA assay and rapid immunogold dipstick", Int. J. Med. Microbiol., vol. 290, No. 3, Urban & Fischer Verlag, 2000, 279-283.
Cheek, Brady J. et al., "Chemiluminescence Detection for Hybridization Assays on the Flow-Thru Chip, a Three-Dimensional Microchannel Biochip", Analytical Chemistry, vol. 73, No. 24, American Chemical Society, Dec. 15, 2001, 5777-5783.
Cheng, et al., "Chip PCR. II Investigation of different PCR amplification systems in Microfabricated silicon-glass chips", Nucleic Acids Research, 1996, 380-385.
Chin, Curtis D. et al., "Lab-on-a-chip devices for global health: Past Studies and future opportunities", Lab Chip, vol. 7, The Royal Society of Chemistry, 2007, 41-57.

(56) References Cited

OTHER PUBLICATIONS

Ciapina, L. P. et al., "A nested-PCR assay for detection of Xylella fastidiosa in citrus plants and sharpshooter leafhoppers", Journal of Applied Microbiology, vol. 96, Society for Applied Microbiology, 2004, 546-551.

Cirino, Nick M. et al., "Multiplex diagnostic platforms for detection of biothreat agents", Expert Rev. Mol. Diagn., vol. 4, No. 6, Future Drugs, Ltd., 2004, 841-857.

Collins, Ruairi, "Purification and characterization of Thermus thermophilus UvrD", Extremophiles, vol. 7, 2003, 35-41.

Compton, J. , "Nucleic acid sequence-based amplification", Nature, vol. 350, Nature Publishing Group, Mar. 7, 1991, 91-92.

Cook, Alan F. et al., "Synthesis and hybridization of a series of biotinylated oligonucleotides", Nucleic Acids Research, vol. 16, No. 9, IRL Press Limited, Oxford, England, 1988, 4077-4095.

Corstjens, et al., "Use of Up-Converting Phosphor Reporters in Lateral-Flow Assays to Detect Specific Nucleic Acid Sequences: A Rapid, Sensitive DNA Test to Identify Human Papillomavirus Type 16 Infection", Clinical Chemistry, 2001, 1885-1893.

Cubero, J. et al., "Genetic Relationship among Worldwide Strains of Xanthomonas Causing Canker in Citrus Species and Design of New Primers for Their Identification by PCR", Applied and Environmental Microbiology, vol. 68, No. 3, American Society for Microbiology, Mar. 2002, 1257-1264.

Cubero, J. et al., "Quantitative PCR Method for Diagnosis of Citrus Bacterial Canker", Applied and Environmental Microbiology, vol. 67, No. 6, American Society for Microbiology, Jun. 2001, 2849-2852.

Davis, Michael J. et al., "Pierce's Disease of Grapevines: Isolation of the Causal Bacterium", Science, vol. 199, Jan. 6, 1978, 775-778.

Dawson, Erica D. et al., "Identification of A/H5N1 Influenza Viruses Using a Single Gene Diagnostic Microarray", Anal. Chem., vol. 79, American Chemical Society, 2007, 378-384.

Day, Philip J. et al., "Immobilization of polynucleotides on magnetic particles", Biochem. J., vol. 278, 1991, 735-740.

De Jong, Menno D. et al., "Oseltamivir Resistance during Treatment of Influenza A (H5N1) Infection", New England Journal of Medicine, vol. 353, No. 25, Massachusetts Medical Society, Dec. 22, 2005, 2667-2672.

Deiman, Birgit et al., "Characteristics and Applications of Nucleic Acid Sequence-Based Amplification (NASBA)", Molecular Biotechnology, vol. 20, Humana Press, Inc., 2002, 163-179.

Dineva, Magda A. et al., "Simultaneous Visual Detection of Multiple Viral Amplicons by Dipstick Assay", Journal of Clinical Microbiology, vol. 43, No. 8, American Society for Microbiology, Aug. 2005, 4015-4021.

Dobkin, Carl et al., "RNA Replication: Required Itermediates and the Dissociation of Template, Product, and QB Replicase", Biochemistry, vol. 18, American Chemical Society, 1979, 2038-2044.

Dong, Feng et al., "A coupled complex of T4 DNA replication helicase (gp41) and polymerase (gp43) can perform rapid and processive DNA strand-displacement synthesis", Proc. Natl. Acad. Sci. USA, vol. 93, Dec. 1996, 14456-14461.

Duck, P. et al., "Probe Amplifier System Based on Chimeric Cycling Oligonucleotides", Biotechniques, vol. 9, No. 2, 1990, 142-148.

Easterday, W. R. et al., "Use of Single Nucleotide Polymorphisms in the plxR Gene for Specific Identification of Bacillus anthracis", Journal of Clinical Microbiology, vol. 43, No. 4, American Society for Microbiology, Apr. 2005, 1995-1997.

Easterday, William R. et al., "Specific detection of Bacillus anthracis using a TaqMan mismatch amplification mutation assay", BioTechniques, vol. 38, No. 5, 2005, 731-735.

Edwards, Katie A. et al., "Optimization of DNA-tagged dye-encapsulating liposomes for lateral-flow assays based on sandwich hybridization", Anal. Bioanal. Chem., vol. 386, 2006, 1335-1343.

Eggerding, "A One-step Coupled Amplification and Oligonucleolide Ligation Procedure for Multiplex Genetic Typing", PCR Methods and Applications, Cold Spring Harbor Laboratory Press, 1995, 337-345.

Elliott, K. et al., "Use of laser microdissection greatly improves the recovery of DNA from sperm on microscope slides", Forensic Science International, vol. 137, No. 1, Elsevier Ireland Ltd., 2003, 28-36.

Findlay, et al., "Automated Closed-Vessel System for inVitro Diagnostics Based on Polymerase Chain Reaction", Clinical Chemistry, 1993, 1927-1933.

Fisher, et al., "Development of a Quantum Dot-Lateral Flow Assay", BEACON e-news at Jet Propulsion Laboratory, 2003.

Fong, Whalley K. et al., "Rapid Solid-Phase Immunoassay for Detection of Methicillin-Resistant *Staphylococcus aureus* Using Cycling Probe Technology", Journal of Clinical Microbiology, vol. 38, No. 7, American Society for Microbiology, Jul. 2000, 2525-2529.

Frackman, et al., "Betaine and DMSO: Enhancing Agents for PCR", Promega Notes, 1998, 27.

Fu, et al., "Controlled reagent transport in disposable 2D paper networks", Lab Chip, 2010, 918-920.

Fukuta, Shiro et al., "Development of immunocapture reverse transcription loop-mediated isothermal amplification for the detection of tomato spotted wilt virus from chrysanthemum", Journal of Virological Methods, vol. 121, No. 1, Elsevier B.V., 2004, 49-55.

Gani, Raymond et al., "Potential Impact of Antiviral Drug Use during Influenza Pandemic", Emerging Infectious Diseases, vol. 11, No. 9, Sep. 2005, 1355-1362.

Gershon, "Microarray technology: An array of opportunities", Nature, vol. 416, Macmillan Magazines, Ltd., Apr. 25, 2002, 416:885-891.

Gill, Peter, "Application of Low Copy Number DNA Profiling", Croatian Medical Journal, vol. 42, No. 3, 2001, 228-232.

Gill, Peter et al., "An investigation of the rigor of interpretation rules for STRs derived from less than 100 pg of DNA", Forensic Science International, vol. 112, Elsevier Science Ireland Ltd., 2000, 17-40.

Glynou, Kyriaki et al., "Oligonucleotide-Functionalized Gold Nanopartices as Probes in a Dry-Reagent Strip Biosensor for DNA Analysis by Hybridization", Analytical Chemistry, vol. 75, No. 16, American Chemical Society, Aug. 15, 2003, 4155-4160.

Goda et al., "Label-Free Potentiometry for Detecting DNA Hybridization Using Peptide Nucleic Acid and NA Probes", Sensors, vol. 13, 2013, 2267-2278.

Goheen, A. C. et al., "Association of a Rickettsialike Organism with Pierce's Disease of Grapevines and Alfalfal Swarf and Heat Therapy of the Disease in Grapevines", Phytopathology, vol. 63, Mar. 1973, 341-345.

Goldmeyer, et al., "Development of a Novel One-Tube Isothermal Reverse Transcription Thermophilic Helicase-Dependent Amplification Platform for Rapid RNA Detection", Journal of Molecular Diagnostics, Nov. 2007, 639-644.

Grainge, Ian et al., "Biochemical analysis of components of the pre-replication complex of Archaeoglobus fulgidus", Nucleic Acids Research, vol. 31, No. 16, Oxford University Press, 2003, 4888-4898.

Groody, E. P., "Detection of Foodborne Pathogens Using DNA Probes and a Dipstick Format", Molecular Biotechnology, vol. 6, Humana Press, Inc., 1996, 323-327.

Guatelli, John C. et al., "Isothermal, in vitro amplification of nucleic acids by a multienzyme reaction modeled after retroviral replication", Proc. Natl. Acad. Sci. USA, vol. 87, Mar. 1990, 1874-1878.

Guo, Zhen et al., "Direct fluorescence analysis of genetic polymorphisms by hybridization with oligonucleotide arrays on glass supports", Nucleic Acids Research, vol. 22, No. 24, Oxford University Press, 1994, 5456-5465.

Harmon, Frank G. et al., "Biochemical Characterization of the DNA Helicase Activity of the *Escherichia coli* RecQ Helicase", The Journal of Biological Chemistry, vol. 276, No. 1, American Society for Biochemistry and Molecular Biology, Inc., 2001, 232-243.

Hartley, Harriet A. et al., "Biosensor for the specific detection of a single viable B. anthracis spore", Anal. Bioanal. Chem., vol. 376, 2003, 319-327.

Hartung, J. S. et al., "Detection of *Xanthomonas campestris* pv. Citri by the Polymerase Chain Reaction Method", Applied and Environmental Microbiology, vol. 59, No. 4, American Society for Microbiology, Apr. 1993, 1143-1148.

(56) References Cited

OTHER PUBLICATIONS

Hartung, John S. et al., "Rapid and Sensitive Colorimetric Detection of *Xanthomonas axonopodis* pv. citri by Immunocapture and a Nested-Polymerase Chain Reaction Assay", Phytopathology, vol. 86, No. 1, American Phytopathological Society, 1996, 95-101.

Heller, M. J., "DNA microarray technology: devices, systems, and applications", Annu. Rev. Biomed. Eng., vol. 4, 2002, 129-153.

Hendson, Mavis et al., "Genetic Diversity of Pierce's Disease Strains and Other Pathotypes of Xylella fastidiosa", Applied and Environmental Microbiology, vol. 67, No. 2, American Society for Microbiology, Feb. 2001, 895-903.

Henegariu, et al., "Multiplex PCR: Critical Parameters and Step-by-Step Protocol", BioTechniques, 1997, 504-511.

Henke et al., "Betaine improves the PCR amplification of GC-rich DNA sequences", Nucleic Acids Research, vol. 25, No. 19, Oxford University Press, 1997, 3957-3958.

Hill, B. L. et al., "Acquisition and Retention of Xylella fastidiosa by an Efficient Vector, Graphocephala atropunctata", Phytopathology, vol. 85, No. 2, American Phytopathological Society, 1997, 209-212.

Hill, B. L. et al., "Populations of Xylella fastidiosa in Plants Required for Transmission by an Efficient Vector", Phytopathology, vol. 87, No. 12, American Phytopathological Society, 1997, 1197-1201.

Hill, Karen K. et al., "Fluorescent Amplified Fragment Length Polymorphism Analysis of Bacillus anthracis, Bacillus cereus, and Bacillus thuringiensis Isolates", Applied and Environmental Microbiology, vol. 70, No. 2, American Society for Microbiology, Feb. 2004, 1068-1080.

Hopkins, D. I., "Xylella fastidiosa: Xylem-Limited Bacterial Pathogen of Plants", Ann. Rev. Phytopathol., vol. 27, Annual Reviews Inc., 1989, 271-290.

Huang et al., "A Capillary-Driven Microfluidic Device for Rapid DNA Detection with Extremely Low Sample Consumption", 17th International Conference on Miniaturized Systems for Chemistry and Life Science, Freiburg, Germany, Oct. 27-31, 2013, 191-193.

Huber, Martin et al., "Accessing Single Nucleotide Polymorphisms in Genomic DNA by Direct Multiplex Polymerase Chain Reaction Amplification on Oligonucleotide Microarrays", Analytical Biochemistry, vol. 303, Elsevier Science (USA), 2002, 25-33.

Huckle, David, "Point-of-care diagnostices: will the hurdles be overcome this time?", Expert Review of Medical Devices, vol. 3.4, 2006, 421-426.

Hutton et al., "Activity of Endonuclease S1 in Denaturing Solvents: Dimethylsulfoxide, Dimethylformamide, Formamide and Formaldehyde", Biochemical and Biophysical Research Communications, vol. 66, No. 3, Academic Press, Inc., 1975, 942-948.

Iakobashvili, et al., "Low temperature cycled PCR protocol for Klenow fragment of DNA polymerase I in the presence of proline", Nucleic Acids Research, 1999, 1566-1568.

Ilyushina, Natalia A. et al., "Detection of amantadine-resistant variants among avian influenza viruses isolated in North America and Asia", Virology, vol. 341, Elsevier, Inc., 2005, 102-106.

Jacobi, V. et al., "Development of a multiplex immunocapture RT-PCR assay for detection and differentiation of tomato and tobacco mosaic tobamoviruses", Journal of Virological Methods, vol. 74, Elsevier Science B.V., 1998, 167-178.

Jacobsen, Nana et al., "Direct isolation of poly(A)+ RNA from 4 M guanidine thiocyanate-lysed cell extracts using locked nucleic acid-oligo(T) capture", Nucleic Acid Research, vol. 32, No. 7, Oxford University Press, 2004, 1031-1042.

Jensen, et al., "DMSO and Betaine Greatly Improve Amplification of GC-Rich Constructs in De Novo Synthesis", DLoS One, Jun. 11, 2010, e11024.

Jobling, Mark A. et al., "Encoded Evidence: DNA in Forensic Analysis", Nature Reviews: Genetics, vol. 5, Oct. 2004, 739-751.

Kandimalla, Ekambar R. et al., "Design, biochemical, biophysical and biological properties of cooperative antisense oligonucleotides", Nucleic Acids Research, vol. 23, No. 17, Oxford University Press, 1995, 3578-3584.

Kane et al., "Assessment of the sensitivity and specificity of oligonucleotide (50mer) microarrays", Nucleic Acids Research, Vo. 28, No. 22, Oxford University Press, 2000, 4552-4557.

Kaplan, Daniel L. et al., "DnaB from Thermus aquaticus Unwinds Forked Duplex DNA with an Asymmetric Tail Length Dependence", The Journal of Biological Chemistry, vol. 274, No. 11, American Society for Biochemistry and Molecular Biology, Inc., Mar. 12, 1999, 6889-6897.

Kempitiya et al., "Localized microwave heating in microwells for parallel DNA amplification applications", Applied Physics Letters, 2009, 064106-1-064106-3.

Keohavong, Phouthone et al., "Fidelity of DNa polymerases in DNA amplification", Proc. Natl. Acad. Sci. USA, vol. 86, Dec. 1989, 9253-9257.

Kieleczawa, Jan et al., "DNA Sequencing by Primer Walking with Strings of Continguous Hexamers", Science, vol. 258, No. 5089, American Association for the Advancement of Science, Dec. 11, 1992, 1787-1791.

Kievits, Tim et al., "NASBA (TM) isothermal enzymatic in vitro nucleic acid amplification optimzed for the diagnosis of HIV-1 infection", Journal of Virological Methods, vol. 35, Elsevier Science Publishers B.V., 1991, 273-286.

Kilbourne, Edwin D. et al., "The total influenza vaccine failure of 1947 revisited: Major intrasubtypic antigenic change can explain failure of vaccine in a post-World War II epidemic", PNAS, vol. 99, No. 16, Aug. 6, 2002, 10748-10752.

Kim et al., "Recombinant fragment assay for gene targeting based on the polymerase chain reaction", Nucleic Acids Research, vol. 16, No. 18, IRL Press Limited, Oxford, England, 1988, 8887-8903.

Kimura, et al., "One-step immobilization for poly(dT)-modified DNA onto non-modified plastic substrates by UV irradiation for microarrays", Biochemical and Biophysical Research Communications, vol. 347, 2006, 477-484.

Koch, Walter H., "Technology Platforms for Pahrmacogenomic Diagnostic Assays", Nature Reviews Drug Discovery, vol. 3, Sep. 2004, 749-761.

Kohn, J., "An Immunochromatographic Technique", Immunology, vol. 15, 1968, 863-865.

Koonjul, Priyum K., "Inclusion of polyvinylpyrrolidone in the polymerase chain reaction reverses the inhibitory effects of polyphenolic contamination of RHNA", Nucleic Acids Research, vol. 27, No. 3, Oxford University Press, 1999, 915-916.

Kornberg, et al., DNA Replication, 2nd Edition, WH Freeman and Company, New York, 1992, 298-299; 356-365.

Kozwich, Diane et al., "Development of a Novel, Rapid Integrated Cryptosporidium parvum Detection Assay", Applied and Environmental Microbiology, vol. 66, No. 7, American Society for Microbiology, Jul. 2000, 2711-2717.

Kwoh, D. Y. et al., "Transcription-based amplification system and detection of amplified human immunodeficiency virus type 1 with a bead-based sandwich hybridization format", Proc. Natl. Acad. Sci. USA, vol. 86, Feb. 1989, 117301177.

Landegren, Ulf et al., "A Ligase-Mediated Gene Detection Technique", Science, vol. 241, Aug. 26, 1988, 1077-1080.

Lane, Michael J. et al., "The thermodynamic advantage of DNA oligonucleotide 'stacking hybridization' reactions: energetics of a DNA nick", Nucleic Acids Research, vol. 25, No. 3, Oxford University Press, 1997, 611-616.

Leone, G. et al., "Direct detection of potato leafroll virus in potato tubers by immunocapture and the isothermal nuclic acid amplification method NASBA", Journal of Virological Methods, vol. 66, Elsevier Science B.V., 1997, 19-27.

Liao et al., "Miniature RT-PCT system for diagnosis of RNA-based viruses", Nucleic Acids Research, Oct. 12, 2005, 1-7.

Lim, Daniel V. et al., "Current and Developing Technologies for Monitoring Agents of Bioterrorism and Biowarfare", Clinical Microbiology Reviews, vol. 18, No. 4, American Society for Microbiology, Oct. 2005, 583-607.

Liu et al., "Self-Contained, Fully Integrated Biochip for Sample Preparation, Polymerase Chain Reaction Amplification and DNA Microarray Detection", Anal. Chem., vol. 76, 2004, 1824-1831.

(56) References Cited

OTHER PUBLICATIONS

Lockley, Andrew K. et al., "Colorimetric detection of immobilised PCR products generated on a solid support", Nucleic Acids Research, vol. 25, No. 6, Oxford University Press, 1997, 1313-1314.

Loens, K. et al., "Evaluation of NucliSens easyMAG for Automated Nucleic Acid Extraction from Various Clinical Specimens", Journal of Clinical Microbiology, vol. 45, No. 2, American Society for Microbiology, Feb. 2007, 421-425.

Lonnberg, Maria et al., "Chromatographic performance of a thin microporous bed of nitrocellulose", Journal of Chromatography B, vol. 763, Elsevier Science BV, 2001, 107-120.

Lowe, Mary et al., "Multiplexed, Particle-Based Detection of DNa Using Flow Cytometry with 3DNA Dendrimers for Signal Amplification", Cytometry Part A, vol. 60, No. 2, Wiley Intersciences, 2004, 135-144.

Mackay, I. M., "Real-time PCR in the microbiology laboratory", Clin Microbiol Infect., vol. 10, European Society of Clinical Microbiology and Infectious Diseases, 2004, 190-212.

Malek, Larry et al., "Nucleic acid sequence-based amplification (NASBA)", Protocols for Nucleic Acid Analysis by Nonradioactive Probes, ed. Peter G. Isaac, Humana Press, Totowa, New Jersey, 1994, 253-260.

Masny, et al., "Ligation mediated PCR performed at low denaturation temperatures-PCT melting profiles", Nucleic Acids Research, 2003, 1-6.

Michalet, Xavier et al., "Properties of Fluorescent Semiconductor Nanocrystals and their Application to Biological Labeling", Single Mol., vol. 2, No. 4, WILEY-VCH Verlag Berlin GmbH, 2001, 261-276.

Miyoshi, Daisuke et al., "Molecular Crowding Regulates the Structural Switch of the DNA G-Quadruplex", Biochemistry, vol. 41, American Chemical Society, Nov. 20, 2002, 15017-15024.

Monteiro, Lurdes et al., "Complex Polysaccharides as PCR Inhibitors in Feces: Helicdobacter pylori Model", Journal of Clinical Microbiology, vol. 35, No. 4, American Society for Microbiology, Apr. 1997, 995-998.

Mumford et al., "Rapid single-tube immunocapture RT-PCR for the detection of two yam potyviruses," Journal of Virological Methods, 1997, vol. 69, pp. 73-79.

Musso et al., "Belaine, Dimethyl Sulfoxide, and 7-Deaza-dGTP, a Powerful Mixture for Amplification of GC-Rich DNJ Sequences", Journal of Molecular Diagnostics, Nov. 2006, 544-550.

Nicholson, Karl G. et al., "Influenza", The Lancet, vol. 362, Nov. 22, 2003, 1733-1745.

O'Meara, Deirdre et al., "Capture of Single-Stranded DNa Assisted by Oligonucleotide Modules", Analytical Biochemistry, vol. 255, Academic Press, 1998, 195-203.

O'Meara, Deirdre et al., "Cooperative Oligonucleotides Mediating Direct Capture of Hepatitis C Virus RNa from Serum", Journal of Clinical Microbiology, vol. 36, No. 9, American Society for Microbiology, Sep. 1998, 2454-2459.

Palese, Peter et al., "Influenza vaccines: present and future", The Journal of Clinical Investigation, vol. 110, No. 1, Jul. 2002, 9-13.

Pannucci, James et al., "Virulence signatures: microarray-based approaches to discovery and analysis", Biosensors and Bioelectronics, vol. 20, Elsevier, B.V., 2004, 706-718.

Pastinen, Tomi et al., "A System for Specific, High-throughput Genotyping by Allele-specific Primer Extension on Microarrays", Genome Research, vol. 10, No. 7, Cold Spring Harbor Laboratory Press, 2000, 1031-1042.

Pemov, A. et al., "DNA analysis with multiplex microarray-enhanced PCR", Nucleic Acid Research, vol. 33, No. 2, Oxford University Press, 2005, 1-9.

Petrik, J., "Diagnostic applications of microarrays", Transfusion Medicine, vol. 16, Blackwell Publishing, Ltd., 2006, 233-247.

Peytavi, Regos et al., "Microfluidic Device for Rapid (<15 min) Automated Microarray Hybridization", Clinical Chemistry, vol. 51, No. 19, 2005, 1836-1844.

Piepenburg, Olaf et al., "DNA Detection Using Recombination Proteins", PLoS Biology, vol. 4, No. 7, Jul. 2006, 1115-1121.

Pooler, M. R. et al., "Detection of Xylella fastidiosa in potential insect vectors by immunomagnetic separation and nested polymerase chain reaction", Letters in Applied Microbiology, vol. 25, Society for Applied Bacteriology, 1997, 1230126.

Pooler, Margaret R. et al., "Specific PCR Detection and Identification of Xylella fastidiosa Strains Causing Citrus Variegated Chlorosis", Current Microbiology, vol. 31, Springer-Verlag New York, Inc., 1995, 377-381.

Pristoupil, T. I., "Microchromatography and Microelectrophoresis on Nitrocellulose Membranes", Chromatographic Reviews, vol. 12, Elsevier Publishing Company, Amsterdam, Netherlands, 1970, 109-125.

Purcell, A. H. et al., "Fate of Pierce's Disease Strains of Xylella fastidiosa in Common Riparian Plants in Californiat", Plant Disease, vol. 83, No. 9, American Phytopathological Society, 1999, 825-830.

Purcell, Alexander H. et al., "Pierce's Disease Bacterium: Mechanism of Transmission by Leafhopper Vectors", Science, vol. 206, Nov. 16, 1979, 839-841.

Rajendrakumar et al., "DNA helix destabilization by proline and betaine: possible role in the salinitiy tolerance process", FEBS Letters, vol. 410, Federation of European Biochemical Sciences, 1997, 201-205.

Ralser, et al., "An efficient and economic enhancer mix for PCR", Biochemical and Biophysical Research communications, 2006, 747-751.

Rao, et al., "Developing rapid, point-of-care, multiplex detection for use in lateral flow devices", Smart Medical and Biomedical Sensor Technology III, Proc. of SPIE, 2005.

Rapley, "Enhancing PCR Amplification and Sequencing Using DNA-Binding Proteins", Molecular Biotechnology, Dec. 1994, 295-298.

Rees et al., "Betaine can eliminate the base pair composition dependence of DNA melting", Biochemistry, 993 [Abstract], 1993.

Reinhartz, Avraham et al., "A novel rapid hybridization technique: paper chromatography hybridization assay (PACHA)", Gene, vol. 136, Elsevier Science Publishers B.V., 1993, 221-226.

Rodriguez, Jorge L. et al., "Detection and Diversity Assessment of Xylella fastidiosa in Field-Collected Plant and Insect Samples by Using 16S rRNA and gyrB Sequences", Applied and Environmental Microbiology, vol. 69, No. 1, American Society for Microbiology, Jul. 2003, 4249-4255.

Romero, Alicia et al., "Amplification and cloning of a long RNA virus genome using immunocapture-long RT-PCR", Journal of Virological Methods, vol. 66, No. 1, Elsevier Science B.V., 1997, 159-163.

Roper, Michael G. et al., "Advances in Polymerase Chain Reaction on Microfluidic Chips", Analytical Chemistry, vol. 77, No. 12, American Chemical Society, 2005, 3887-3894.

Rouse, Richard et al., "Microarray technology—an intellectual property retrospective", Pharmacogenomics, vol. 4, No. 5, Ashley Publications Ltd., 2003, 1462-2416.

Rule, Geoffrey S. et al., "Rapid method for visual identification of specific DNA sequences based on DNA-tagged liposomes", Clinical Chemistry, vol. 42, No. 8, 1996, 1206-1209.

Saiki, Randall K. et al., "Primer-Directed Enzymatic Amplification of DNA with a Thermostable DNA Poymerase", Science, vol. 239, Jan. 29, 1988, 487-491.

Sambrook, et al., Molecular Cloning: A Laboratory Manual, 3rd Edition, Cold Spring Harbor Laboratory Press, Cold Spring Harbor, New York, 2001, 9.47-9.55.

Sarkar, et al., "Formamide can dramatically improve the specificity of PCR", Nucleic Acids Research, Dec. 25, 1990, 7465.

Schildkraut, Carl et al., "Dependence of the Melting Temperature of DNA on Salt Concentration", Biopolymers, vol. 3, 1965, 195-208.

Schuchard et al., "Two-Step "Hot" PCR Amplification of GC-Rich Avian c-myc Sequences", BioTechniques, vol. 14, No. 3, 1993, 390-394.

Schwab et al., "Immunoaffinity concentration and purification of waterborne enteric viruses for detection by reverse transcriptase PCR," Appl. Environ. Microbiol., 1996, vol. 62, No. 6, pp. 2086-2094.

(56) References Cited

OTHER PUBLICATIONS

Shoffner, et al., "Chip PCR. I. Surface passivation of microfabricated silicon-glass chips for PCR", Nucleic Acids Research, 1996, 375-379.
Singh, Sanjay K. et al., "LNA (locked nucleic acids): synthesis and high-affinity nucleic acid recognition", Chem. Commun., vol. 4, 1998, 455-456.
Spiess, "Trehalose Is a Potent PCR Enhancer: Lowering of DNA Melting Temperature and Thermal Stabilization of Taq Polymerase by the Disaccharide Trehalose", Clinical Chemistry, Jul. 2004, 1256-1259.
Spiro, Alexander et al., "A Bead-Based Method for Multiplexed Identification and Quantitation of DNA Sequences Using Flow Cytometry", Applied and Environmental Microbiology, vol. 66, No. 10, American Society for Microbiology, Oct. 2000, 4258-4265.
Stears, Robin L. et al., "A novel, sensitive detection system for high-density microarrays using dendrimer technology", Physiol. Genomics, vol. 3, American Physiological Society, 2000, 93-99.
Sterne, Max, "The use of Anthrax Vaccines Prepared from Avirulent (encapsulated) Variants of Bacillus anthracis", Onderstepoort Journal of Veterinary Science and Animal Industry, vol. 13, No. 2, Government Printer, Pretoria, Union of South Africa, Oct. 1939, 307-312.
Stiver, Grant, "The treatment of influenza with antiviral drugs", CMAJ, vol. 168, No. 1, Canadian Medical Association, Jan. 7, 2003, 49-57.
Sunen et al., Recovery and detection of enterovirus, hepatitis A virus and Norwalk virus in hardshell clams (*Mercenaria mercenaria*) by RT-PCR methods, Journal of Virological Methods 77 (1999) 179-187.
Tennikova, Tatiana B. et al., "An Introduction to Monolithic Disks as Stationary Phases for High Performance Biochromatography", J. High Resol. Chromatogr., vol. 23, No. 1, WILEY-VCH Verlag GmbH, 2000, 27-38.
Tennikova, Tatiana B. et al., "High-performance membrane chromatography: highly efficient separation method for proteins in ion-exchange, hydrophobic interaction and reversed-phase models", Journal of Chromatography, vol. 646, Elsevier Science Publishers B.V., 1993, 279-288.
Thommes, J. et al., "Membrane Chromatography—An Integrative Concept in the Downstream Processing of Proteins", Biotechnol. Prog., vol. 11, American Chemical Society and American Institute of Chemical Engineers, 1995, 357-367.
Tsai, Yu-Li et al., "Rapid Method for Separation of Bacterial DNA from Humic Substances in Sediments for Polymerase Chain Reaction", Applied and Environmental Microbiology, vol. 58, No. 7, American Society for Microbiology, Jul. 1992, 2292-2295.
Van Ness, Jeffrey et al., "Isothermal reactions for the amplification of oligonucleotides", PNAS, vol. 100, No. 8, Apr. 15, 2003, 4504-4509.
Vincent, Myriam et al., "Helicase-dependent isothermal DNa amplification", EMBO Reports, vol. 5, No. 8, European Molecular Biology Organization, 2004, 795-800.
Wahlestedt, Claes et al., "Potent and nontoxic antisense oligonucleotides containing locked nucleic acids", PNAS, vol. 97, No. 10, May 9, 2000, 5633-5638.
Walker, G. T. et al., "Isothermal in vitro amplification of DNA by a restriction enzyme/DNA apolymerase system", Proc. Natl. Acad. Sci. USA, vol. 89, Jan. 1992, 392-396.
Walker, G. T. et al., "Strand displacement amplification-an isothermal, in vitro DNA amplification technique", Nucleic Acid Research, vol. 20, No. 7, Oxford University Press, 1992, 1691-1696.
Wang, et al., "Droplet-based micro oscillating-flow PCR chip", Journal of Micromechanics and Microengineering, 2005, 1369-1377.
Webby, R. J. et al., "Are we ready for pandemic influenza?", Science, vol. 302, Nov. 28, 2003, 1519-1522.
Webster, Robert G. et al., "Potential Impact of Antiviral Drug Use during Influenza Pandemic", American Scientist, vol. 91, 2003, 122-129.
Wei, Cheng-Wey et al., "Using a microfluidic device for 1 ul DNA micrarray hybridization in 500 s", Nucleic Acids Research, vol. 33, No. 8, Oxford University Press, 2005, 1-11.
Weighardt, et al., "A Simple Procedure for Enhancing PCR Specificity", PCR Methods and Applications, Aug. 1, 1993, 77-81.
Wells, John M. et al., "Isolation, Culture, and Pathogenicity of the Bacterium Causing Phony Disease of Peach", Phytopathology, vol. 73, No. 6, American Phytopathological Society, 1983, 859-862.
Wetzel, T. et al., "A highly sensitive immunocapture polymerase chain reaction method for plum pox potyvirus detection", Journal of Virological Methods, vol. 39, Elsevier Science Publishers B.V., Jul. 1992, 27-37.
Wickenheiser, Ray A., "Trace DNA: A Review, Discussion of Theory, and Application of the Transfer of Trace Quantities of DNA Through Skin Contact", J Forensic Sci, vol. 137, No. 1, ASTM Int'l, 2002, 442-450.
Wilding, et al., "PCR in a Silicon Microstructure", Clinical Chemistry, 1994, 1815-1818.
Wilson, "Inhibition and Facilitation of Nucleic Acid Amplification", Applied and Environmental Microbiology, vol. 63, No. 10, 1997, 3741-3751.
Yang, Samuel et al., "PCR-based diagnositcs for infectious diseases: uses, limitations, and future applications in acute-care settings", The Lancet Infectious Diseases, vol. 4, Jun. 2004, 337-348.
Young, Charles C. et al., "Polyvinylpyrrolidone-Agarose Gel Electrophoresis Purification of Polymerase Chain Reaction-Amplifiable DNA from Soils", Applied and Environmental Microbiology, vol. 59, No. 6, American Society for Microbiology, Jun. 1993, 1972-1974.
Zaytseva, Natalya V. et al., "Multi-analyte single-membrane biosensor for the serotype-specific detection of Dengue virus", Anal. Bioanal. Chem., vol. 380, 2004, 46-53.
Zeng, et al., "High GC Amplification: A Comparative Study of Betaine, DMSO, Formamide and Glycerol as Additives", Life Science Journal, 2006, 67-71.
Zhang, et al., "PCR microfluidic devices for DNA amplification", Biotechnology Advances, 2006, 243-284.
Zijlmans, H.J.M.A.A. et al., "Detection of Cell and Tissue Surface Antigens Using Up-Converting Phosphors: A New Reporter Technology", Analytical Biochemistry, vol. 267, Academic Press, 1999, 30-36.
Zuiderwijk, Michel et al., "An amplication-free hybridization-based DNA assay to detect *Streptococcus pneumoniae* utilizing the upconvewrting phosphor technology", Clinical Biochemistry, vol. 36, The Canadian Society of Clinical Chemists, 2003, 401-403.
Mouritzen et al., "Single Nucleotide Polymorphism Genotyping Using Locked Nucleic Acid (LNA™)," January, vol. 3, No. 1, pp. 27-38 (2003).
Extended European Search Report issued by the European Patent Office for Application No. 16784104.8, dated Feb. 12, 2019, 11 pages.
Wang et al., "Identifying Influenza Viruses with Resequencing Microarrays," Emerging Infectious Diseases, April, vol. 12, No. 4, pp. 638-646. (2006).

* cited by examiner

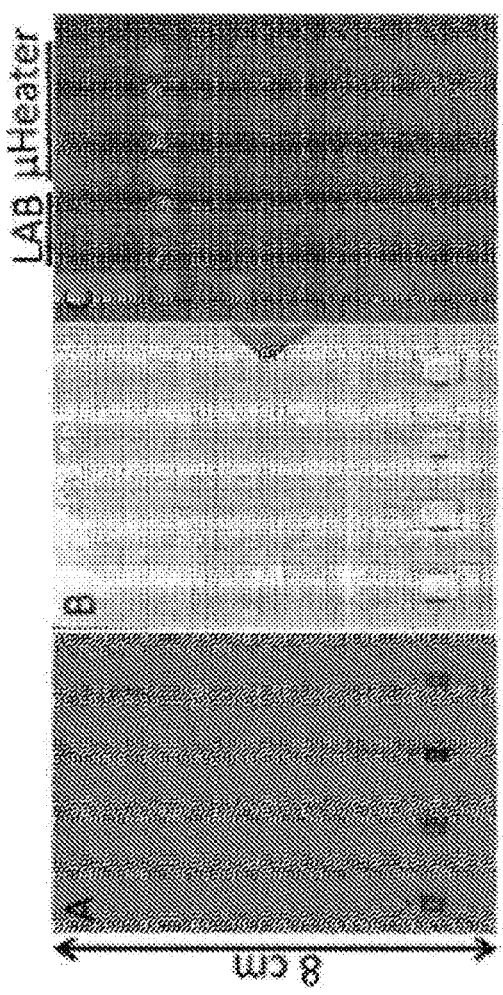
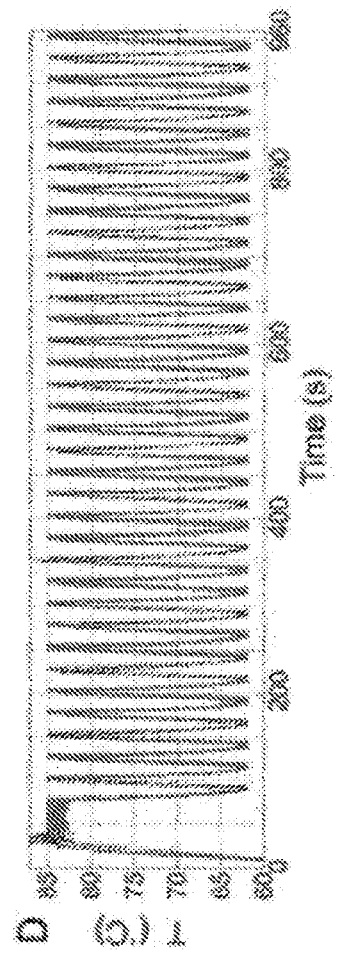
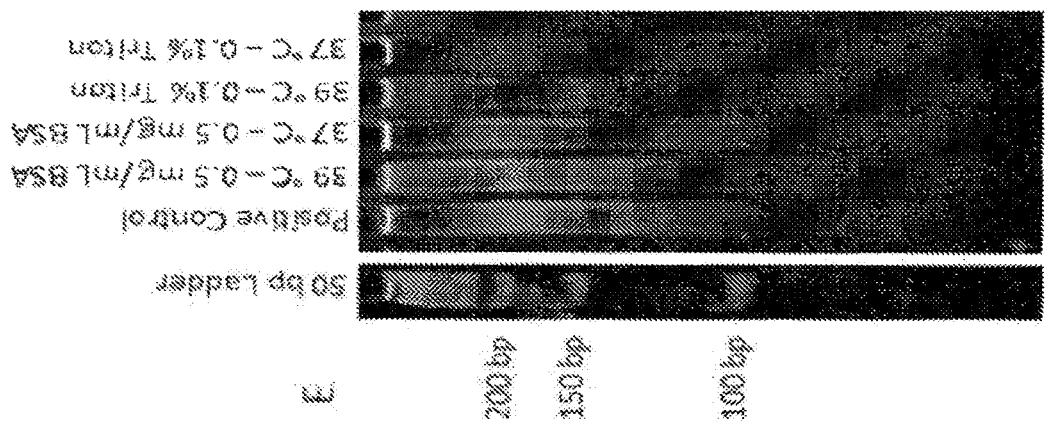
FIG. 4A  FIG. 4B  FIG. 4C
FIG. 4D
FIG. 4E

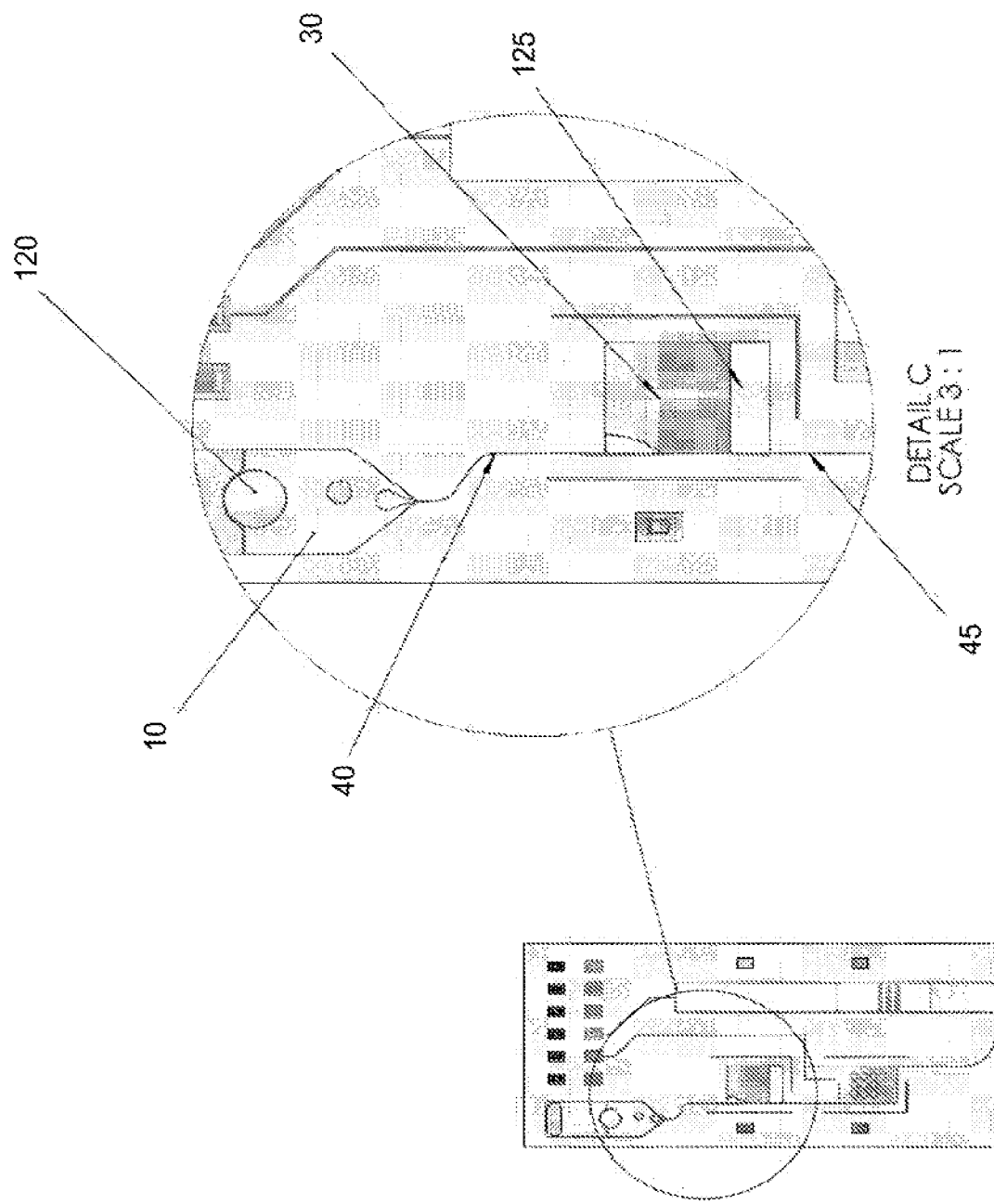

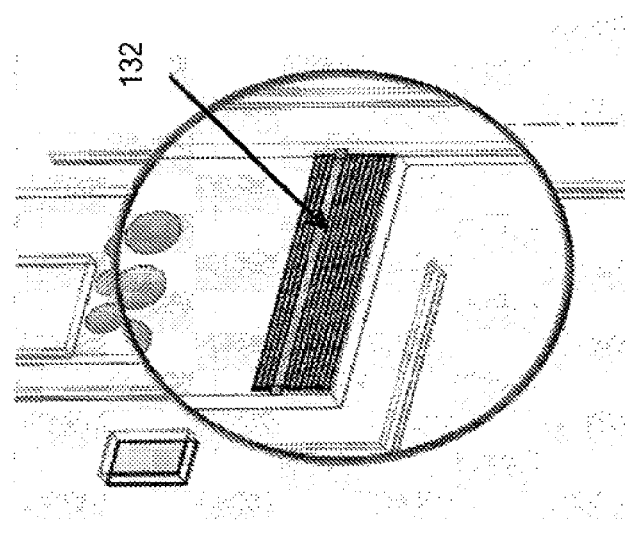
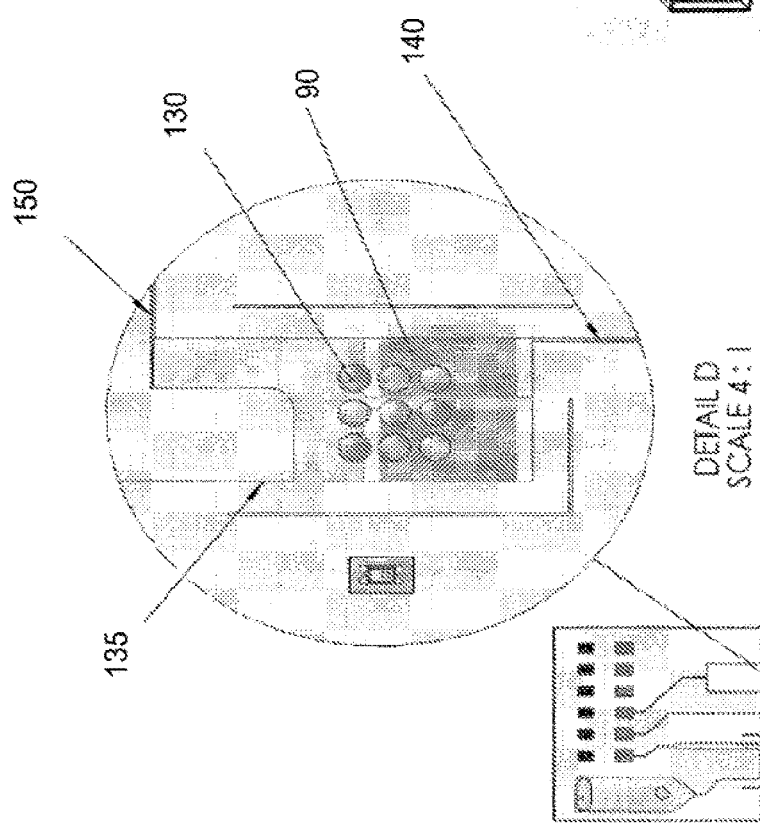
FIG. 6B
FIG. 6A

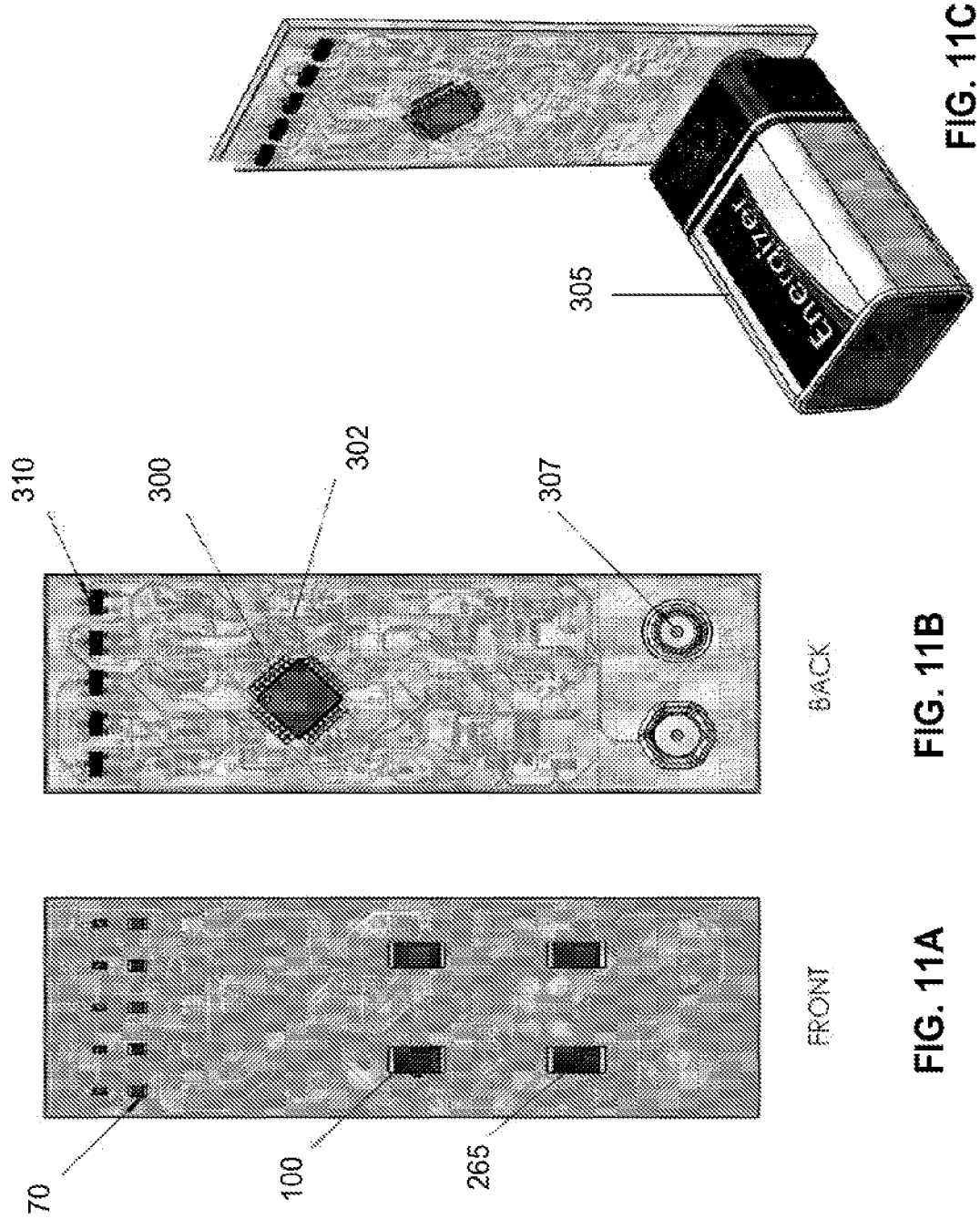

INTEGRATED DEVICE FOR NUCLEIC ACID DETECTION AND IDENTIFICATION

CROSS-REFERENCE TO RELATED APPLICATIONS

This application is a continuation application of U.S. application Ser. No. 14/113,146, filed Oct. 21, 2013 know issued as U.S. Pat. No. 10,519,492), which is a U.S. National Stage Application under U.S.C. § 371 of International Application No. PCT/US2012/034596, filed Apr. 20, 2012, which claims priority to and the benefit of filing of U.S. Provisional Patent Application Ser. No. 61/477,357, entitled "Integrated Device for Nucleic Acid Detection and Identification", filed on Apr. 20, 2011, and U.S. Provisional Patent Application Ser. No. 61/477,437, entitled "Oscillating Amplification Reaction for Nucleic Acids", filed on Apr. 20, 2011, which are incorporated herein by reference.

REFERENCE TO A SEQUENCE LISTING, A TABLE, OR COMPUTER PROGRAM

Applicant hereby submits a sequence listing as a text file titled 042012_ST25.txt created on Nov. 8, 2019 having 1.17 kbytes that is ASCII compliant and is hereby incorporated by reference.

BACKGROUND OF THE INVENTION

Field of the Invention (Technical Field)

Embodiments of the present invention relate to an integrated device and related methods for detecting and identifying nucleic acids. The device may be fully disposable or may comprise a disposable portion and a reusable portion.

Background Art

Note that the following discussion refers to a number of publications and references. Discussion of such publications herein is given for more complete background of the scientific principles and is not to be construed as an admission that such publications are prior art for patentability determination purposes.

As the public health impact and awareness of infectious and emerging diseases, biothreat agents, genetic diseases and environmental reservoirs of pathogens has increased, the need for more informative, sensitive and specific point-of-use rapid assays has increased the demand for polymerase chain reaction (PCR)-based tools. Nucleic acid-based molecular testing by such methods as PCR-based amplification is extremely sensitive, specific and informative. Unfortunately, currently available nucleic acid tests are unsuitable or of limited utility for field use because they require elaborate and costly instrumentation, specialized laboratory materials and/or multiple manipulations dependent on user intervention. Consequently, most samples for molecular testing are shipped to centralized laboratories, resulting in lengthy turn-around-times to obtain the required information.

To address the need for rapid point-of-use molecular testing, prior efforts have focused on product designs employing a disposable cartridge and a relatively expensive associated instrument. The use of external instrumentation to accomplish fluid movement, amplification temperature control and detection simplifies many of the engineering challenges inherent to integrating the multiple processes required for molecular testing. Unfortunately, dependence upon elaborate instrumentation imposes tremendous economic barriers for small clinics, local and state government and law enforcement agencies. Further, dependence upon a small number of instruments to run tests could cause unnecessary delays during periods of increased need, as occurs during a suspected biowarfare agent release or an emerging epidemic. Indeed, the instrument and disposable reagent cartridge model presents a potentially significant bottleneck when an outbreak demands surge capacity and increased throughput. Additionally, instrumentation dependence complicates ad hoc distribution of test devices to deployment sites where logistic constraints preclude transportation of bulky associated equipment or infrastructure requirements are absent (e.g. reliable power sources).

Gravity has been described as a means of fluid movement in existing microfluidic devices. However, the typical device does not allow for programmable or electronic control of such fluid movement, or the mixing of more than two fluids. Also, some devices utilize a pressure drop generated by a falling inert or pre-packaged fluid to induce a slight vacuum and draw reactants into processing chambers when oriented vertically, which increases storage and transport complexities to ensure stability of the pre-packaged fluids. Existing devices which teach moving a fluid in a plurality of discrete steps require frangible seals or valves between chambers, which complicates operation and manufacture. These devices do not teach the use of separate, remotely located vents for each chamber.

Typical microfluidic devices typically make use of smaller reaction volumes than are employed in standard laboratory procedures. PCR or other nucleic acid amplification reactions such as loop mediated amplification (LAMP), nucleic acid based sequence amplification (NASBA) and other isothermal and thermal cycling methods are typically conducted in testing and research laboratories using reaction volumes of 5 to 100 microliters. These reaction volumes accommodate test specimen volumes sufficient to ensure the detection of scarce assay targets in dilute specimens. Microfluidic systems that reduce reaction volumes relative to those employed in traditional laboratory molecular testing necessarily also reduce the volume of specimen that can be added to the reaction. The result of the smaller reaction volume is a reduction in capacity to accommodate sufficient specimen volume to ensure the presence of detectable amounts of target in dilute specimens or where assay targets are scarce.

SUMMARY OF THE INVENTION

An embodiment of the present invention is a disposable platform for detecting a target nucleic acid, the disposable platform comprising a sample chamber for receiving a sample comprising the target nucleic acid; an amplification chamber connected via a first channel to the sample chamber and connected via a second channel to a first vent pocket; a labeling chamber connected via a third channel to the amplification chamber and connected via a fourth channel to a second vent pocket; a detection subsystem connected to the labeling chamber via a fifth channel and connected via a sixth channel to a third vent pocket; a plurality of resistive heating elements; and one or more temperature measuring devices; wherein the vent pockets are each sealed from the atmosphere by a heat labile membrane located in a vicinity of one of the resistive heating elements. The disposable platform optionally further comprises a sample preparation stage comprising an output in direct fluid connection with an input of the sample chamber. Dimensions of a substantially flat surface of the amplification chamber are preferably approximately the same as dimensions of a substantially flat surface of a resistive heating element in thermal contact with the amplification chamber. The amplification chamber is preferably not cooled by an active cooling device. The amplification chamber optionally contains an amplification solution, the sample chamber optionally comprises a liquid amplification reagent mix or a lyophilized amplification reagent mix, and/or the labeling chamber optionally comprises detection particles. The labeling chamber is preferably heatable using one of the resistive heating elements. The detection subsystem comprises a lateral flow strip that preferably does not comprise detection particles. The chambers, the channels, and the vent pockets are preferably located on a fluid assembly layer and the electronic elements are preferably located on a separate layer comprising a printed circuit board, the separate layer bonded to the fluid assembly layer. The detection subsystem is preferably located on the fluid assembly layer or optionally on a second fluid assembly layer. The volume of at least one of the chambers is preferably between approximately 1 microliter and approximately 50 microliters. The disposable platform preferably further comprises a connector for docking the disposable platform with a base unit that is not an external instrument and that maintains the disposable platform in a vertical or tilted orientation.

An embodiment of the present invention is a method for detecting a target nucleic acid, the method consisting of disposing a sample comprising the target nucleic acid in a sample chamber of a disposable platform; orienting the disposable platform vertically or at a tilt; reacting the sample with a liquid or previously lyophilized amplification reagent mix; opening a first vent pocket connected to an amplification chamber to atmosphere, thereby enabling the reacted sample to flow into the amplification chamber; amplifying the target nucleic acid in the amplification chamber; opening a second vent pocket connected to a labeling chamber to atmosphere, thereby enabling the amplified target nucleic acid to flow into the labeling chamber; labeling the amplified target nucleic acid using detection particles in the labeling chamber; opening a third vent pocket connected to a detection subsystem to atmosphere, thereby enabling the labeled target nucleic acid to flow into the detection subsystem; and detecting the amplified target nucleic acid. The amplifying step preferably comprises amplifying the target nucleic acid using a resistive heating element located within the disposable platform in a vicinity of the amplification chamber. The method preferably further comprises passively cooling the amplification chamber. The method preferably further comprises heating the labeling chamber during the labeling step using a resistive heating element located within the disposable platform in a vicinity of the labeling chamber. The detection subsystem preferably does not comprise detection particles. The method preferably further comprises controlling operation of the disposable platform by using a docking station which is not an external instrument.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate embodiments of the present invention and, together with the description, serve to explain the principles of the invention. The drawings are only for the purpose of illustrating certain embodiments of the invention and are not to be construed as limiting the invention. In the drawings:

FIG. 4A-E depict embodiments of the present invention which support either thermal cycling or isothermal-based nucleic acid amplification methodologies. FIG. 4A shows a PCA with four resistor/thermistor pairs. Four surface mount resistors serve as four independently controllable heaters (arrows). FIG. 4B shows a fluidic assembly attached to the PCA of FIG. 4A consistent with the resistive heater detail of FIG. 3. The fluidic layer interfaces with the surface mount resistors of the PCA to provide reaction chambers for nucleic acid amplification. FIG. 4C shows gel electrophoresis of amplification reactions producing a ~150 bp (base pair) product from a PCR machine (LAB) or by an embodiment of the present invention (µHeater) by thermal cycling. The left most lane is size standard. FIG. 4D is a graph of temperature versus time in seconds for fluid within the amplification chamber of the present embodiments. The darker line indicates temperature of solution in the reaction chamber obtained by thermocouple. The lighter line is the temperature measured by the thermistor used by the microcontroller for temperature control. 40 cycles of a two-temperature PCR reaction can be accomplished in less than 20 minutes using a 20 µL reaction volume. FIG. 4E shows gel electrophoresis of isothermal Nucleic Acid Sequence Based Amplification (NASBA) reactions producing an ~150 bp product from a PCR machine (Positive Control), or by use of an embodiment of the present invention. Four separate reactions indicate both the setting of the temperature sensor, and a particular surface treatment applied to the interior of the fluidic chamber.

FIG. 5 illustrates an embodiment of the present invention comprising the technique of transporting fluid without the use of a vent. By heating the chamber below the fluid column, gas will expand and purge itself through the inlet channel. Upon cooling, the gas in the chamber volume will contract and draw in a volume of fluid proportional to that of the purged gas. The fluid drops to the chamber floor. Successive iterations of this cycle can move the full reaction volume. The operation of is technique depends on channel size, length, heat time and temperature, chamber volumes, and surface energies of components.

FIG. 6A-B show the detail and function of a labeling chamber of an embodiment of the present invention. Fluid containing amplicon enters the labeling chamber through the inlet channel and contacts detection particles. Sufficient mixing is accomplished by heating or boiling of fluid. Rising bubbles nucleated at the bottom and sides of the chamber, preferably by a textured feature such as a laser etched line or series of lines, preferably effectively stir the mixture. In this embodiment, SMD components are the same as those used in the amplification heater.

FIG. 11A is drawing of the front side of the PCA of a disposable invention configuration embodiment of the present invention. This side faces the fluidic assembly. Heating and sensor elements as well as user interface components such as LED indicators are present in this embodiment.

FIG. 11B is a drawing illustrating the layout of the back side of the PCA of the disposable invention configuration of FIG. 11A. This side of the PCB holds the control circuitry such as the microcontroller, MOSFET switches, and ancillary circuitry. In this embodiment, terminals are present for a 9V battery, as well as optional user interface devices such as tactile switches useful for assay initiation.

FIG. 11C is a drawing of the PCA of FIG. 11B with 9V battery installed. Plastic housing is not shown. Battery placement is preferably as shown to lower the center of mass and to help prevent tipping or overturning of device during operation.

In FIG. 16A, required enzymes were added to the reaction solution in liquid form. In FIG. 16B, required enzymes were supplied by incorporation of a lyophilized pellet into the sample chamber. The amplification and detection of nucleic acid was performed as described in Example 1. The top line of the detection strip assembly represents the positive control, an oligonucleotide complementary to the detection probe. The line immediately below the positive control represents the capture line, an immobilized oligonucleotide complementary to the same amplification product strand as the detection probe.

DETAILED DESCRIPTION OF THE INVENTION

Figure 1:
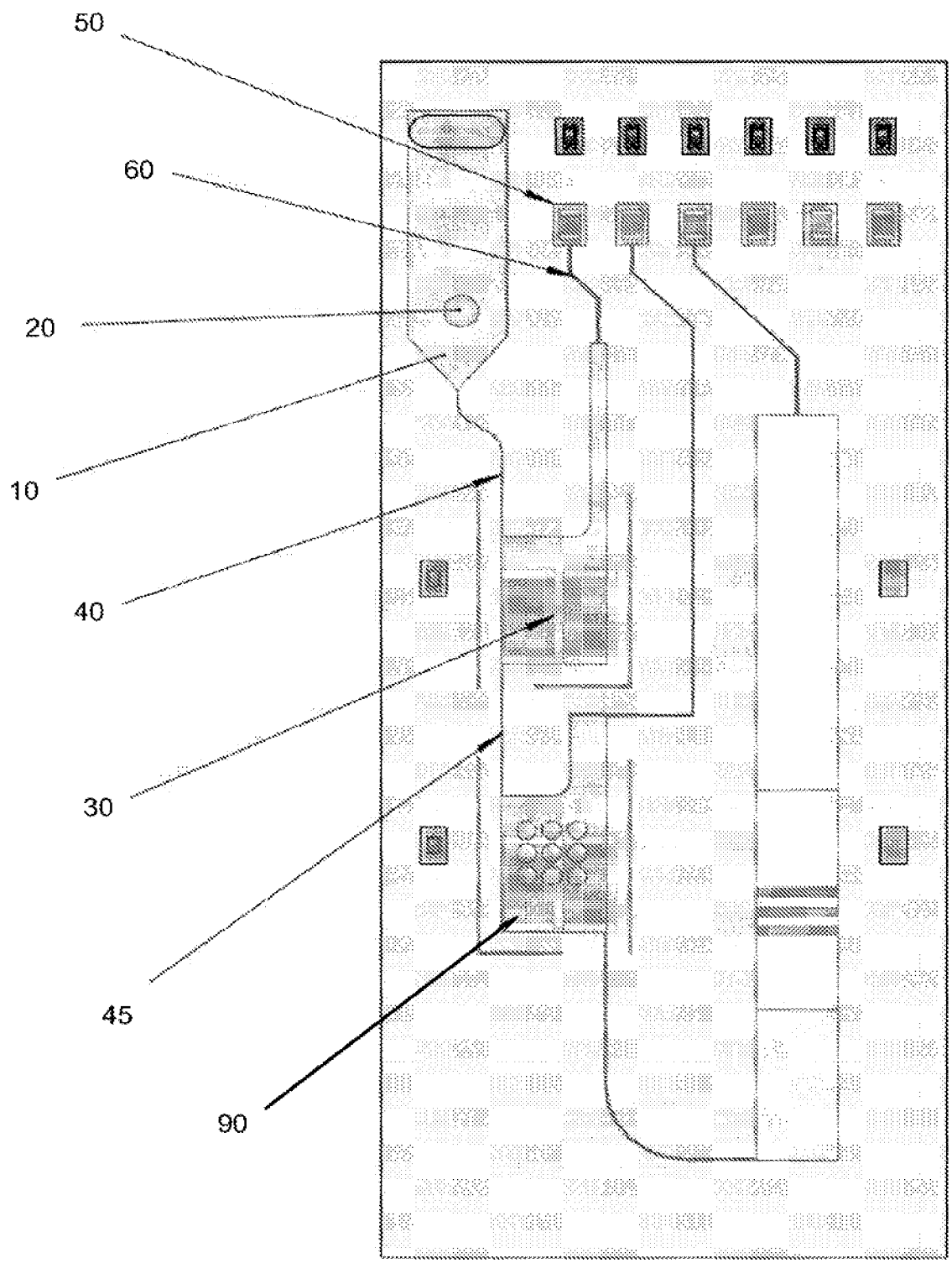
FIG. 1 is a drawing illustrating the fluidic and electronic layers for an embodiment of the present invention. Prepared sample fluid enters the sample chamber where it is mixed with preferably lyophilized reagents. In the vertical orientation, pressure of the fluid column equilibrates with the sealed volume of air below it. Capillarity prevents the escape of air and further advancement of fluid. When the appropriate vent seal underlying the corresponding vent pocket is ruptured, fluid moves through the outlet channel to the next chamber for further processing. Temperature and fluid control is preferably achieved using standard printed circuit assembly (PCA) components and assembly techniques.

Embodiments of the present invention comprise a disposable platform which integrates instrumentation independent means of conducting all requisite steps of a nucleic acid molecular assay and complements current immuno-lateral flow rapid assays with a new generation of nucleic acid tests offering more informative and sensitive analyses. Embodiments of the present invention facilitate the broader use of rapid nucleic acid testing in small clinics and austere settings where infectious disease, biothreat agent, agriculture and environmental testing are the most likely to have the greatest impact. Certain embodiments of the present invention are completely self-contained and disposable which enables "surge capacity" in times of increased demand by allowing parallel tests to be run without instrumentation-imposed bottlenecks. Additionally, in those application areas where a low cost disposable cartridge coupled with an inexpensive battery-powered or AC adapter energized docking station is preferable, an embodiment of the invention where a simple docking station is employed further reduces test costs by placing reusable components in a reusable yet inexpensive base. The platform technology disclosed herein offers sensitivity similar to laboratory nucleic acid amplification-based methods, minimal user intervention and training requirements, sequence specificity imparted by both amplification and detection, multiplex capacity, stable reagents, compatibility with low-cost large-scale manufacturing, battery operation to allow use in austere settings, and a flexible platform technology allowing the incorporation of additional or alternative biomarkers without device redesign.

Embodiments of the present invention provide systems and methods for low-cost, point-of-use nucleic acid detection and identification suitable to perform analyses in locations remote from a laboratory environment where testing would ordinarily be performed. Advantageously, nucleic acid amplification reaction volumes can be in the same volume range commonly used in traditional laboratory testing (e.g. 5-100 µL). The reaction conducted in embodiments of the present invention is thus directly comparable to accepted laboratory assays, and allows the accommodation of the same specimen volumes typically employed in traditional molecular testing.

Embodiments of the present invention may be used to detect the presence of a target nucleic acid sequence or sequences in a sample. Target sequences may be DNA such as chromosomal DNA or extra-chromosomal DNA (e.g. mitochondrial DNA, chloroplast DNA, plasmid DNA etc) or RNA (e.g. rRNA, mRNA, small RNAs and viral RNA). Similarly, embodiments of the invention may be used to identify nucleic acid polymorphisms including single nucleotide polymorphisms, deletions, insertions, inversions and sequence duplications. Further, embodiments of the invention may be used to detect gene regulation events such as gene up- and down-regulation at the level of transcription. Thus, embodiments of the invention may be employed for such applications as: 1) the detection and identification of pathogen nucleic acids in agricultural, clinical, food, environmental and veterinary samples; 2) detection of genetic biomarkers of disease; and 3) the diagnosis of disease or a metabolic state through the detection of relevant biomarkers of the disease or metabolic state, such as gene regulation events (mRNA up- or down regulation or the induction of small RNAs or other nucleic acid molecules generated or repressed during a disease or metabolic state) in response to the presence of a pathogen, toxin, other etiologic agent, environmental stimulus or metabolic state.

Embodiments of the present invention comprise a means of target nucleic acid sample preparation, amplification, and detection upon addition of a nucleic acid sample, comprising all aspects of fluid control, temperature control, and reagent mixing.

In some embodiments of the invention, the device provides a means of performing nucleic acid testing using a portable power supply such as a battery, and is fully disposable. In other embodiments of the invention, a disposable nucleic acid test cartridge works in conjunction with a simple reusable electronic component which does not perform all of the functions of typical laboratory instrumentation.

Embodiments of the present invention provide for a nucleic acid amplification and detection device comprising, but not limited to, a housing, a circuit board, and a fluidic or microfluidic layer. In certain embodiments, the circuit board may contain a variety of surface-mount components such as resistors, thermistors, light-emitting diodes (LEDs), photodiodes, and microcontrollers. The fluidic or microfluidic layer is responsible for moving aqueous reaction volumes and may be made from a variety of plastics and by a variety of manufacturing techniques including bonding, fusing or lamination of laser cut, water-jet cut or injection molded pieces. The fluidics and circuit board components are held together and their thermal coupling may be enhanced by heat conducting materials or compounds. The housing preferably serves in part as a cosmetic and protective sheath, hiding the delicate components of the microfluidic and circuit board layers, and may also serve to facilitate sample input, buffer release, nucleic acid elution and the initiation of processes required for device functionality. For example, the housing may incorporate a sample input port, a button or similar mechanical feature to allow user activation, buffer release, sample flow initiation and/or nucleic acid elution.

In some embodiments of the invention, the fluidic or microfluidic layer preferably comprises four chambers, including a sample input chamber, an amplification chamber, a nucleic acid labeling chamber, and a detection chamber. The solution input chamber preferably comprises a sample input orifice where a nucleic acid containing sample may be added, and an egress conduit leading to the amplification chamber. The sample input chamber may also comprise lyophilized reagents that may include suitable buffers, salt, deoxyribonucleotides, ribonucleotides, oligonucleotide primers, and enzymes such as DNA polymerase and reverse transcriptase. Such lyophilized reagents are preferably solubilized upon addition of the nucleic acid sample. The amplification chamber is preferably situated in register and thermal contact with heater elements on the circuit board. Similarly, electronic components present on the circuit board are placed in physical contact or proximity to vents or valve structures in the fluidic layer to enable electronic control. The circuit board physical layout is designed to provide registration with elements of the fluidic or microfluidic layer such that resistive heating elements of the circuit board for amplification and/or fluid flow control are situated to form contacts with elements of the fluidic component with which they interact.

Other embodiments of the invention comprise a nucleic acid amplification and detection device that is integrated with a sample preparation device. Embodiments including the sample preparation device provide a means for the communication of fluids between sample preparation subsystem output ports or valves and the input port or ports of the fluidic or microfluidic components of the device.

Unless otherwise defined, all terms of art, notations and other scientific terminology used herein are intended to have the meanings commonly understood by those of skill in the art to which this invention pertains. The techniques and procedures described or referenced herein are generally well understood and commonly employed using conventional methodologies by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

As used throughout the specification and claims, the terms 'target nucleic acid' or 'template nucleic acid' mean a single-stranded or double-stranded DNA or RNA fragment or sequence that is intended to be detected.

As used throughout the specification and claims, the terms 'microparticle' or 'detection particle' mean any compound used to label nucleic acid product generated during an amplification reaction, including fluorescent dyes specific for duplex nucleic acid, fluorescently modified oligonucleotides, and oligonucleotide-conjugated quantum dots or solid-phase elements such as a polystyrene, latex or paramagnetic particles or microspheres.

As used throughout the specification and claims, the term 'chamber' means a fluidic compartment where fluid resides for some period of time before being directed to another chamber. For example, a chamber may be the sample chamber, amplification chamber, labeling chamber, or the detection chamber.

As used throughout the specification and claims, the term 'pocket' means a compartment overlaid onto a resistor or other mechanism that serves as a venting mechanism. For example, unlike fluidic chambers as described above, a pocket created in the fluidic layer may have one open face that aligns with a resistor on the PCA. This open face is preferably covered by a thin membrane to create a sealed cavity that is easily ruptured by energizing the underlying resistor.

As used throughout the specification and claims, the term 'channel' means a narrow conduit within the fluidic assembly which typically connects two or more chambers and/or pockets or combinations thereof, including, for example, an inlet, outlet, or a vent channel. In the case of an inlet or outlet channel, fluid sample migrates through the channel. In the case of a vent channel, the conduit remains clear of fluid and connects a fluidic chamber to a vent pocket.

As used throughout the specification and claims, the term "external instrument" means a reusable instrument that heats and/or cools a disposable assay, and/or performs a mechanical action on a disposable assay, including but not limited to piercing buffer packets and/or pumping or otherwise actively providing a transport force for fluids.

Embodiments of the present invention are devices for low-cost, point-of-use nucleic acid testing suitable to perform analyses in locations remote from a laboratory environment where testing would ordinarily be performed. Certain devices comprise fluidic and electronic components or layers, optionally encased by a protective housing. In embodiments of the present invention, the fluidic layer is composed of plastic and is a series of chambers and pockets connected by narrow channels in which chambers are oriented vertically with respect to one another during operation. The fluidic layer is overlaid or otherwise placed in physical contact with electronic components such as a printed circuit board containing off-the-shelf surface mount devices (SMDs) and controlled via a microcontroller. In some embodiments of the device, the entire assembly is disposable. In other embodiments, the fluidic and physically bonded electronic layers are disposable, while a small inexpensive controlling unit is reusable. In another embodiment, the fluidic layer is disposable, and a small controlling base unit is reusable. For all embodiments, the present invention may be integrated with a nucleic acid sample preparation device such as that described in International Publication No. WO 2009/137059 A1, entitled "Highly Simplified Lateral Flow-Based Nucleic Acid Sample Preparation and Passive Fluid Flow Control" (incorporated herein by reference), and/or use methods described therein.

Embodiments of the present invention comprise an integrated nucleic acid testing device that can be manufactured inexpensively with established manufacturing processes. The invention provides molecular test data while retaining the simplicity from the end-user perspective of widely accepted handheld immunoassays, overcoming the challenges of regulating fluid temperatures within the device, transporting small sample volumes in sequential steps, reagent mixing, and detecting nucleic acids. Embodiments of the present invention are uniquely adapted to utilize off-the-shelf electronic elements that may be constructed by standard assembly techniques, and requires no moving parts. Furthermore, the fluid layer design enables the use of readily available plastics and manufacturing techniques. The result is an inexpensive, disposable, and reliable device capable of nucleic acid isolation, amplification, and detection without the need for a dedicated laboratory infrastructure.

Existing nucleic acid testing devices generally use sophisticated heating elements such as deposited film heaters and Peltier devices that add significant cost and/or require specialized manufacturing methods. In embodiments of the invention, heating of the reaction solution is preferably accomplished by use of simple resistive surface-mount devices that may be purchased for pennies or less and are assembled and tested by common manufacturing standards. By layering fluidic chambers over these resistive elements and associated sensor elements, the fluid temperature of the reaction solutions may be conveniently regulated. The broad use of SMD resistors in the electronics industry ensures that the present invention is amenable to well established quality control methods. Many nucleic acid amplification techniques, such as PCR, require not only rapid heating of the reaction solution but rapid cooling as well. Reaction chambers in the present invention are preferably heated on one side and the ambient temperature across the opposite face is used to help reduce fluid temperature. In addition, vertical orientation of embodiments of the device allows for more rapid cooling by passive convection than if the device was oriented horizontally, thus, reducing the thermal cycle period without the use of costly fans or Peltier devices.

Fluid control is another challenge associated with low-cost nucleic acid test device designs. Devices known in the art generally employ electromechanical, electrokinetic, or piezoelectric pumping mechanisms to manipulate fluids during device operation. These pumping elements increase both device complexity and cost. Similarly, valves making use of elaborate micromechanical designs or moving parts can increase fabrication costs and reduce reliability due to complications such as moving part failure or bio-fouling. Unlike previously described nucleic acid testing devices, embodiments of the present invention utilize hydrostatic pressure under microcontroller control together with capillary forces and surface tension to manipulate fluid volumes. The vertical orientation of some embodiments of the present invention allows for the reaction solution to cascade from chamber to chamber under microcontroller control to accommodate required manipulations of the assay. Fluid may be held in individual reaction chambers through a balance of channel size and surface tension, where surface tension prohibits fluid advancement by gas displacement.

Sample advances to the lower chamber preferably only after activation of a simple venting mechanism under microcontroller control. Once open, the vent allows fluid to move from a first chamber to a second chamber by means of providing a path for displaced air to escape from the second chamber as fluid enters. Each chamber within the fluidic layer preferably connects to a sealed vent pocket through a narrow vent channel. The vent pocket is preferably sealed on one face with a thin plastic membrane that is easily ruptured by heating a small surface mount resistor underlying the membrane. Once the vent of a lower chamber is opened, fluid advancement proceeds, even under low hydrostatic pressures.

As more specifically described below, the fluidic or microfluidic valve mechanism used in some embodiments of the present invention preferably employs a heating element in thermal and (optional) physical contact with a heat labile seal to enable electronic control of fluid movement by means of venting a chamber of lower elevation to allow a fluid from a chamber of higher elevation to flow into the lower chamber. In one embodiment, a surface mount resistor is mounted on a printed circuit board, using widely used and well-established electronics manufacturing methods, and placed in physical contact with a channel seal composed of heat labile material. When energized the surface mount resistor generates sufficient heat to rupture the seal, which results in the venting of the chamber to lower pressure, such as ambient pressure, thus allowing the movement of fluid from a chamber of higher elevation to a chamber of lower elevation. A direct seal between higher and lower elevation chambers is preferably not employed. The channel and seal may be located remotely from the fluid chambers, thus facilitating fluidic device layout in configurations efficient for manufacture. The seal material may comprise any material that can seal the vent channel and be ruptured from heating as described, for example a thin plastic sheet. This approach to fluid movement control in the apparatus benefits from low materials costs, suitability for manufacture using established lamination and electronics manufacturing techniques while providing the capacity to move fluids through a series of chambers under the control of electronic control circuits such as microprocessors or microcontrollers. The use of vents, a heat labile material to seal the vents (and not to seal the fluid chambers or fluid microchannels themselves) and an electronic means of breaking said seal with heat provides a means of controlling fluid flow through the device to enable movement of fluid at predetermined times or following the completion of specific events (for example, attaining a temperature, a temperature change or a series of temperature changes, or the completion of an incubation time or times or other events).

In addition, the vent approach has a number of advantages over sealing the fluid chambers themselves. Vent pockets can be located anywhere on the fluidics layout and simply communicate with the chamber they regulate via a vent channel. From a manufacturing standpoint, vent pockets can be localized so that only a single sealing membrane for all vent pockets (which may comprise a vent pocket manifold) is affixed to the fluidic layer, preferably by well established methods such as adhesives, heat lamination, ultrasonic welding, laser welding etc. In contrast, directly sealing a fluid chamber requires that the seal material be placed at different locations corresponding to each chamber location, which is more difficult to manufacture. This presents a more challenging scenario during manufacture compared to a single vent pocket manifold sealed by a single membrane.

In addition, sealing material located at the chamber will likely come into contact with the solution held in the chamber. This requires the use of a material that (i) does not interfere with the reactions conducted in the chamber, and (ii) is not affected by the solution. Given the sensitivity of the biochemical reactions to chemical inhibitors and the elevated temperatures used for both amplification and labeling prior to detection, the list of acceptable materials becomes limited. Furthermore, the physical proximity of heat sensitive material directly associated with reaction chambers used to conduct reactions at elevated temperatures presents a significant challenge to ensure thermal isolation of the valve sealing material from the elevated temperatures employed during the reactions, in addition to preventing the solution from heating up when the sealing material is melted. To avoid valve failure, the heat sensitive material must be remotely located relative to the heat source or the heat sensitive material must be activated at temperatures well above the highest temperature employed in the reactions. Remotely locating seals directly associated with chambers in a miniaturized device imposes constraints on fluidics layouts that impede the use of compact physical designs. And the use of higher temperatures to trigger valves located at the reaction chamber site can be deleterious to biochemical components that lose stability slightly above the employed reaction temperatures. Finally, if chambers are directly sealed, melted sealing material can remain in the channels between chambers, occluding flow. The viscosity of the sealing material may require more pressure in the fluid column than is obtained in a miniaturized gravity driven apparatus.

In embodiments of the present invention, reagent mixing requires no more complexity than other systems. Reagents necessary for nucleic acid amplification such as buffers, salts, deoxyribonucleotides, oligonucleotide primers, and enzymes are preferably stably incorporated by use of lyophilized pellets or cakes. These lyophilized reagents, sealed in a fluidic chamber, may be readily solubilized upon contact with aqueous solution. In the case that additional mixing is required, the vertical orientation of embodiments of the present invention offers opportunities for novel methods of mixing solutions. By utilizing heaters underlying fluidic chambers, gas may be heated, delivering bubbles to the reaction solution in the chamber above when the solution contains thermally-sensitive components. Alternatively, heaters may be used to directly heat a solution to the point that boiling occurs, in the case that the solution contains no thermally-sensitive components. The occurrence of air bubbles is often undesirable in previously disclosed fluidic and microfluidic devices, as they may accumulate in fluidic chambers and channels and displace reaction solutions or impede fluid movement within the device. The vertical design of embodiments of the invention presented herein allows bubbles to rise to the fluid surface, resulting in only minimal and transient fluid displacement, effectively ameliorating any disadvantageous impacts of bubbles on the fluidic or microfluidic system. Mixing by boiling is also convenient with this vertical design, as fluid displaced during the process simply returns to the original fluidic chamber by gravity after the heating elements are turned off.

In embodiments of the invention, a colorimetric detection strip is used to detect amplified nucleic acids. Lateral flow assays are commonly used in immuno-assay tests due to their ease of use, reliability, and low cost. The prior art contains descriptions of the use of lateral flow strips for the detection of nucleic acids using porous materials as a sample receiving zone which is at or near a labeling zone also comprised of a porous material and placed at or near one end of the lateral flow assay device. In these prior inventions labeling moieties are in the labeling zone. The use of porous materials to comprise the sample receiving zone and the labeling zone results in the retention of some sample solution as well as detection particles in the porous materials. Although labeling zones comprising porous materials having reversibly immobilized moieties required for detection may be used in embodiments of the present invention, embodiments of the present invention preferably utilize detection particles or moieties held in a region of the device distinct from the sample receiving zone of the lateral flow strip and comprising nonporous materials with low fluid retention characteristics. This approach allows nucleic acid target containing samples to be labeled prior to introduction to the porous components of the sample receiving end of the lateral flow component of the device and thereby eliminates the retention and/or loss of sample material and detection particles in a porous labeling zone. This method further enables the use of various treatments of the sample in the presence of detection moieties, such as treatment with high temperatures, to accomplish denaturation of a double-stranded target or secondary structures within a single-stranded target without concern for the impacts of temperature on porous sample receiving or labeling zone materials or the lateral flow detection strip materials. Additionally, the use of a labeling zone not in lateral flow contact with the sample receiving zone but subject to the control of fluidic components such as vents or valves allows target and label to remain in contact for periods of time controlled by fluid flow control systems. Thus embodiments of the present invention can be different than traditional lateral flow test strips wherein sample and detection particle interaction times and conditions are determined by the capillary transport properties of the materials. By incorporating the detection particles in a temperature-regulated chamber, denaturation of duplex nucleic acid is possible allowing for efficient hybridization-based detection. In alternative embodiments, fluorescence is used to detect nucleic acid amplification using a combination of LEDs, photodiodes, and optical filters. These optical detection systems can be used to perform real-time nucleic acid detection and quantification during amplification and end-point detection after amplification.

Embodiments of the invention comprise a low cost, point-of-use system is provided wherein a nucleic acid sample may be selectively amplified and detected. Further embodiments include integration with a nucleic acid sample preparation device such as that described in International Publication No. WO 2009/137059 A1, entitled "Highly Simplified Lateral Flow-Based Nucleic Acid Sample Preparation and Passive Fluid Flow Control". An embodiment of the device preferably comprises both a plastic fluidic component and printed circuit assembly (PCA), and is optionally encased in a housing that protects the active components. Temperature regulation, fluid and reagent mixing are preferably coordinated by a microcontroller. The reaction cassette is preferably oriented and run vertically so that hydrostatic pressure, capillary forces and surface tension, in conjunction with microcontroller triggered vents, control fluid movement within the device.

Referring to the representative schematic in FIG. 1, a nucleic acid sample is added to sample chamber 10. The nucleic acid sample may derive from an online (i.e. integrated nucleic acid preparation sub-system), a separate nucleic acid preparation process (such as one of many commercially available methods, e.g. spin-columns) followed by addition of the purified nucleic acid to the device by pipette, or an unprocessed nucleic acid containing sample. Preferably already present in the sample chamber, or alternatively added later, is a reagent mix, which may be in liquid or dry form, containing all components necessary for the amplification reaction, such as buffering agents, salts, dNTPs, rNTPs, oligonucleotide primers, and/or enzymes. In some embodiments the reagent mix is lyophilized to form lyophilized reagents 20. Introduction of the sample to the sample chamber causes reagents and samples to commingle such that the reagents act upon the sample. An optional bubble-mixing step to further mix the sample with the reagents or resuspend the reagents may optionally be performed. Fluid is then preferably directed through inlet channel 40 to one or more amplification chamber(s) 30 that reside below the sample chamber when the device is in the vertical orientation. Outlet channel 45 connects amplification chamber 30 to a subsequent chamber. To facilitate multiplexed tests, wherein multiple amplicons are generated, multiplexed amplification can be accomplished by deposition of multiple primer sets within the amplification chambers. Additionally, circuit board and fluidic designs in which multiple amplification and detection chambers are incorporated into the device support multiple parallel amplification reactions that may be single-plex or multiplex reactions. This approach reduces or eliminates the complications known to those skilled in the art that result from multiplexed amplification using multiple pairs of primers in the same reaction. Moreover, the use of multiple amplification reaction chambers allows simultaneous amplification under different temperature regimens to accommodate requirements for optimal amplification, such as different melting or annealing temperatures required for different target and/or primer sequences.

Figures 2A, 2B:
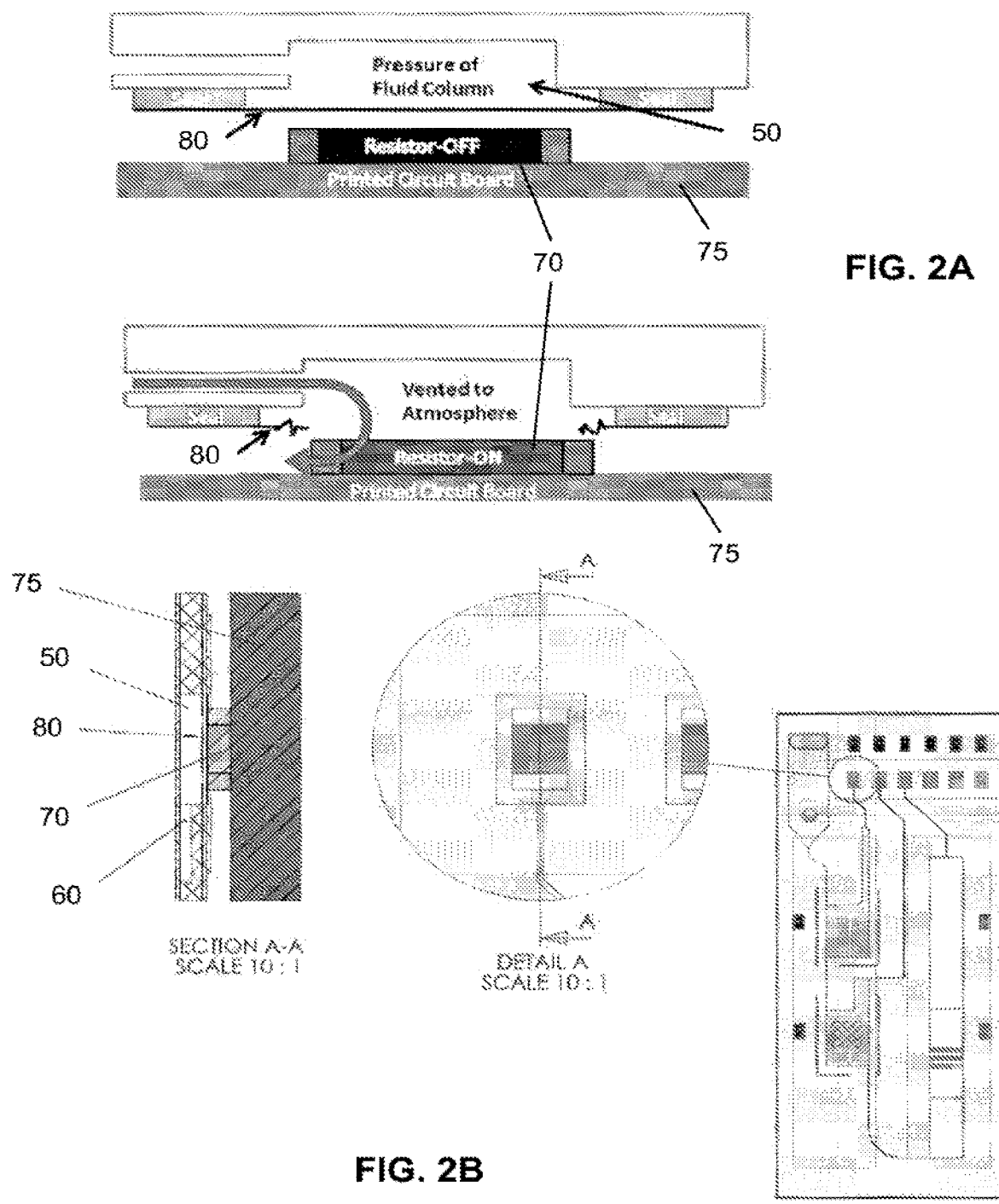
FIG. 2A is a schematic representation of a vent mechanism employed in an embodiment of the present invention to accomplish controlled fluid movement within the fluidic layer.
FIG. 2B is a drawing illustrating the vent location and construction in an embodiment of the present invention. A membrane holds the pressure of the fluid column above ambient. When sufficient heat is applied, the membrane ruptures and allows pressure to equilibrate. Fluid moves along the hydrostatic pressure gradient. Pressures can be less than a few mBar.

Fluid movement from a first chamber to a second chamber of the device is preferably accomplished by the opening of a vent connected to the second chamber as shown in FIGS. 1-2. One embodiment of the vent comprises two components, vent pocket 50, one face of which comprises a membrane such as polyolefin and is in contact with a resistor mounted to the printed circuit board assembly (PCA) 75, and vent channel 60 that connects vent pocket 50 to the microfluidic compartment under its control. When fluid is first added to the system at the sample chamber, the vent, connected to the downstream chamber, is sealed and fluid will not pass through the channel connecting the two chambers. A microcontroller is responsible for sending electrical current to a heating element, such as resistor 70, located at or near the membrane that comprises one face of vent pocket 50. Heat produced by the energized resistor disrupts thin membrane 80, thus opening the vent. Once open, the vent allows fluid to drop from the first chamber to the second chamber by means of providing a path for displaced air to escape from the second chamber as fluid enters. Other embodiments of the vent pocket may comprise seals other than a heat-sensitive membrane, and may utilize other methods of breaking the seals, such as puncturing, tearing, or dissolving.

Figure 3:
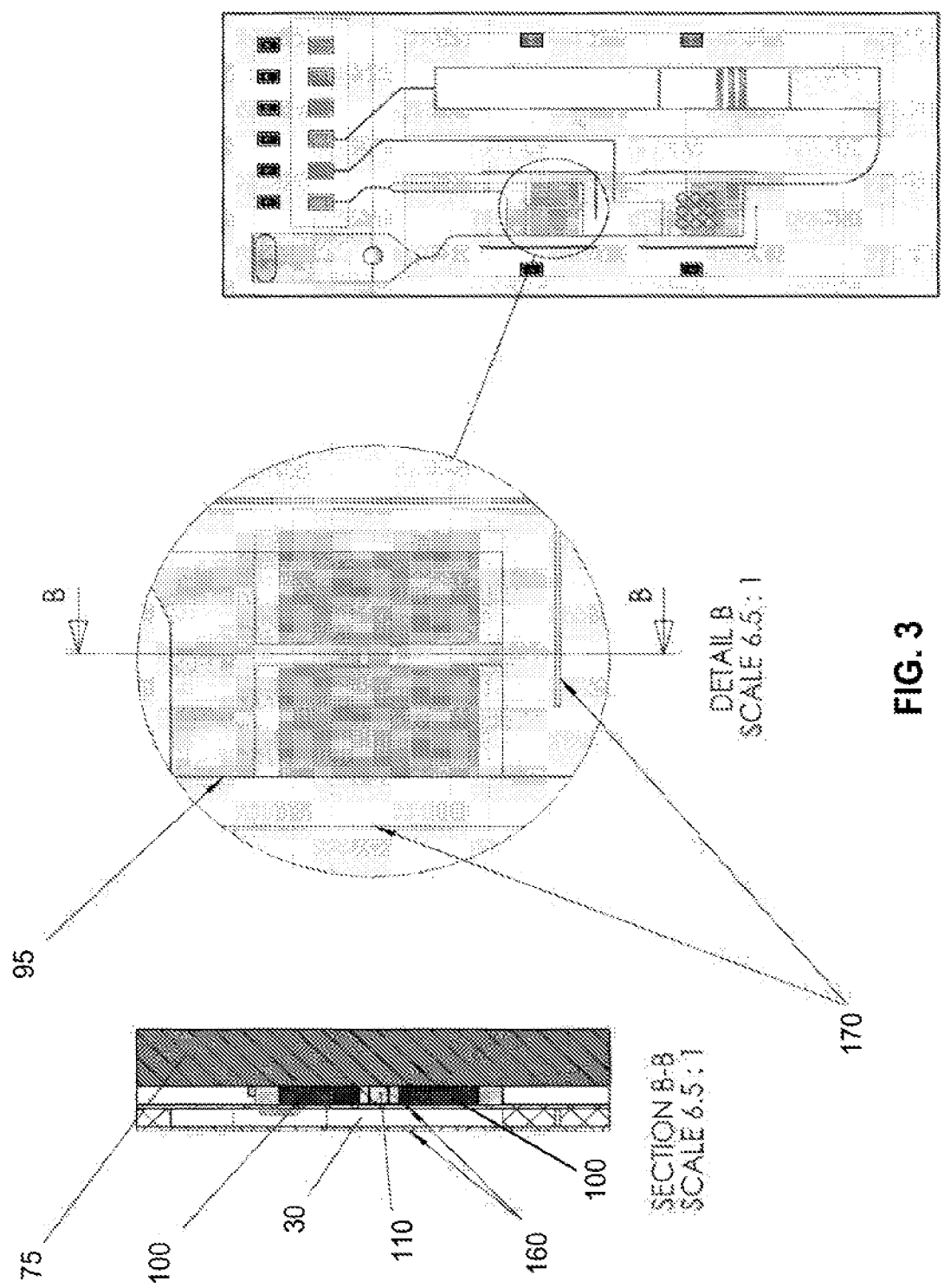
FIG. 3 shows further resistive heater details of an embodiment of the present invention. Two 2512 sized thick-film surface mount device (SMD) resistors (heating element) flank a 0402 sized thermistor (temperature sensor) on the printed circuit board (PCB). A thin layer of thermal compound at the interface of the resistor(s) and the amplification chamber maintains thermal conductivity to the heaters and sensor. Dimensions of the chamber are preferably chosen to maximize the area/volume ratio.

The amplification chamber is preferably in contact with heater elements to provide a means for the temperature regulation necessary to support nucleic acid amplification. In some embodiments of the invention the amplification chamber may contain oligonucleotides on at least a portion of the interior surface. As shown in FIGS. 1-3, an embodiment of the device comprises inlet channel 30 leading from sample chamber 10 to amplification chamber 30, outlet channel 45 preferably leading from amplification chamber 30 to labeling chamber 90, and vent channel 60 leading to vent pocket 50 as described above. At the interface between the amplification chamber wall 95 and heater element(s) 100 it may be advantageous to place a thermally conductive material such as a thermal grease or compound. A microcontroller modulates current to the preferably resistive heating element(s), preferably by means of metal oxide semiconductor field effect transistors (MOSFETs), based upon data collected from temperature sensor 110, preferably using simple on/off or proportional integral derivative (PID) temperature control methods or other algorithmic temperature control known to those skilled in the art.

Existing systems employ active heating and cooling devices located in a reusable instrument to accomplish temperature control for nucleic acid amplification taking place in a disposable cartridge, which necessarily requires an instrument of sufficient precision to be capable of reliably forming reproducible thermal contract with a removable disposable cartridge. This results in increased instrument cost and complexity, as well as reduced reliability of the thermal interface between the temperature control subsystem of the instrument and the fluidic subsystem of the disposable cartridge. Unlike these systems, embodiments of the present invention preferably comprise resistive heating elements for temperature control placed on the disposable portion of the apparatus, such as those illustrated in FIG. 11 and as described above. Placing the heating elements and corresponding temperature sensor(s) on the disposable component enables the manufacture of highly reproducible thermal coupling between the temperature control subsystem and the amplification and detection chambers to which they interface. This approach enables a highly reliable means of coupling the fluidic subsystem to the electronic thermal control subsystem by forming the thermally conductive interface during manufacture. The resulting superior thermal contact between the electronic temperature control components and the fluidic subsystem results in rapid temperature equilibration, and therefore rapid assays.

Embodiments of the amplification chamber preferably comprise materials capable of withstanding repeated heating and cooling to temperatures in the range of approximately 30° C. to approximately 110° C. Even more preferably, the amplification chamber comprises materials capable of withstanding repeated heating and cooling to temperatures in the range of approximately 30° C. to approximately 110° C. at a rate of temperature change on the order of approximately 10° C. to approximately 50° C. per second. The amplification chamber is preferably capable of maintaining solutions therein at temperatures suitable for either thermal cycling (FIG. 4A-D) or isothermal amplification protocols (FIG. 4E), depending on the programming of the microcontroller. In some nucleic acid amplification applications, it is desirable to provide an initial incubation at an elevated temperature, for example a temperature between approximately 37° C. and approximately 110° C. for a period of 1 second to 5 minutes, to denature the target nucleic acid. Subsequently, the reaction solution is varied in temperature between at least two temperatures including, but not limited to, a temperature that results in nucleic acid duplex denaturation and a temperature suitable to primer annealing by hybridization to the target and extension of the primer through polymerase catalyzed nucleic acid polymerization. The duration of incubations at each requisite temperature in a thermal cycling regimen may vary with the sequence composition of the target nucleic acid and the composition of the reaction mix, but is preferably between approximately 0.1 seconds and approximately 20 seconds. Repeated heating and cooling is typically performed for approximately 20 cycles to approximately 50 cycles. In embodiments involving isothermal amplification methods, the temperature of the reaction solution is maintained at a constant temperature (in some cases following an initial incubation at an elevated temperature) for between approximately 3 minutes and approximately 90 minutes depending on the amplification technique used. Once the amplification reaction is complete, the amplification reaction solution is transported, by opening the vent that is in communication with the labeling chamber, to the labeling chamber that is located below the amplification chamber.

In some embodiments, additional biochemical reactions may be conducted in the amplification chamber prior to, during, or after the amplification reaction. Such processes may include but are not limited to reverse transcription wherein RNA is transcribed into cDNA, multiplexing wherein multiple primer pairs simultaneously amplify multiple target nucleic acids, and real time amplification wherein amplification products are detected during the amplification reaction process. In the case of the latter, the amplification chamber may not contain a valve or outlet channel, and the amplification chamber would preferably comprise an optical window or otherwise configured to enable interrogation of amplicon concentration during the amplification reaction process. In one real time amplification embodiment, either fluorescently labeled oligonucleotides complementary to the target nucleic acid or fluorescent dyes specific for duplex DNA are monitored for fluorescence intensity by means of an excitation light source such as LEDs or diode laser(s) and a detector such as a photodiode, and appropriate optical components including but not limited to optical filters.

In alternative embodiments of the invention, fluid movement is facilitated using resistive heating to expand gasses within the device chambers (FIG. 5). For example, by heating amplification chamber 30, gas within the chamber expands and will escape through the vented channel, in this case inlet channel 40, as bubbles 120. In some embodiments of the invention, such heating of a downstream chamber may be used to generate bubbles sufficient to mix reagents present in the fluid volume of an upstream chamber, such as sample chamber 10. Once the heating element is turned off, the gas within amplification chamber 30 will cool and contract, drawing fluid 125 from sample chamber 10 above into amplification chamber 30. By repeating the process several times, the entire fluid volume may be directed from one chamber to another. In alternative embodiments of the invention, such a mechanism may be used in conjunction with a resistor vent mechanism to displace fluid volumes.

Embodiments of the labeling chamber preferably provide for the specific labeling of amplified target nucleic acids generated in the amplification chamber and works in conjunction with the detection chamber to provide the analytical results of the test. As shown in FIG. 6A, labeling chamber 90 may contain detection particles 130 that are dried, lyophilized, or present on at least a portion of the interior surface as a dried mixture of detection particles in a carrier such as a polysaccharide, detergent, protein or other compound known to those skilled in the art to facilitate resuspension of the detection particles. Labeling chamber preferably is connected to inlet channel 135 leading from amplification chamber 30, outlet channel 140 leading to the detection chamber, and vent channel 150 leading to a vent pocket as described above. Inlet channel 135 is typically the same channel as outlet channel 45 of amplification chamber 30. At the interface with the PCA, a thin layer of thermally conductive material such as thermal grease is preferably disposed between one face of the labeling chamber and a resistive heating element.

Suitable detection particles include but are not limited to fluorescent dyes specific for duplex nucleic acid, fluorescently modified oligonucleotides, or oligonucleotide-conjugated dyed microparticles or colloidal gold. Detection of amplicon involves a 'detection oligonucleotide' or other 'detection probe' that is complementary or otherwise able to bind specifically to the amplicon to be detected. Conjugation of a detection oligonucleotide to a microparticle may occur by use of streptavidin coated particles and biotinylated oligonucleotides, or by carbodiimide chemistry whereby carboxylated particles are activated in the presence of carbodiimide and react specifically with primary amines present on the detection oligonucleotide. Conjugation of the detection oligonucleotide to the detectable moiety may occur internally or at the 5' end or the 3' end. Detection oligonucleotides may be attached directly to the microparticle, or more preferably through a spacer moiety such as ethyleneglycol or polynucleotides.

In the case of a duplex DNA amplification product, heating the reaction solution following introduction to the detection chamber facilitates detection. Melting the duplex DNA and then cooling in the presence of detection oligonucleotide results in the sequence-specific labeling of the amplified target nucleic acid. The resistive element underlying the labeling chamber may be used to heat the fluid volume for approximately 1 to approximately 120 seconds to initiate duplex DNA melting. As the solution is allowed to cool to room temperature, the amplified target nucleic acid may specifically hybridize to detection microparticles. The reaction volume is then preferably directed to a region of the detection chamber below the labeling chamber by opening the vent of the detection chamber.

For efficient labeling to occur, the solubilized detection particles are preferably well mixed with the reaction solution. In embodiments of the invention, a second mixing method involving resistive heaters may be employed during labeling to both denature double-stranded nucleic acid target and sufficiently mix detection microparticles in the reaction solution. Heating of the solution in the labeling chamber to above the boiling point may be used to induce turbulence and mixing in solution. Rising bubbles nucleated at the bottom and sides of the chamber by a textured feature such as laser etched line 132, shown in FIG. 6B (or a series of such lines), preferably effectively stirs the solution. This effect has been demonstrated to work at many altitudes, independent of corresponding boiling temperature variations. Any solution displaced into upper chambers by boiling preferably flows downstream back into the labeling chamber during subsequent cooling. In some embodiments of the invention, regions of the inner face or the labeling chamber walls may be textured or otherwise treated to localize nucleate boiling to a specific chamber wall or face. In other embodiments, one or more boiling chips may be placed in the labeling chamber to localize nucleate boiling to a specific point(s).

Embodiments of the detection chamber of the present invention provide for the specific detection of amplified target nucleic acids that have been labeled in the labeling chamber. In certain embodiments of the invention, detection is accomplished by capillary wicking of solution containing labeled amplicon through an absorbent strip comprised of a porous material (such as cellulose, nitrocellulose, polyethersulfone, polyvinylidine fluoride, nylon, charge-modified nylon, or polytetrafluoroethylene) patterned with lines, dots or other visually discernable elements comprising a binding moiety capable of specifically binding to the labeled amplicon either directly or indirectly. In some embodiments, the absorbent strip component of the device comprises up to three porous substrates in physical contact: a surfactant pad comprising amphipathic reagents to enhance wicking, a detection zone comprising a porous material (such as cellulose, nitrocellulose, polyethersulfone, polyvinylidine fluoride, nylon, charge-modified nylon, or polytetrafluoroethylene) to which at least one binding moiety capable of selectively binding labeled amplicon is immobilized, and/or an absorbent pad to provide additional absorbent capacity. Unlike previously described lateral flow detection devices, detection particles are preferably not incorporated within the lateral flow porous materials in the detection chamber, but are instead held upstream in the labeling chamber where manipulations to substantially enhance the formation of binding complexes between amplicon and detection particles, such as heating/boiling, may be conducted prior to the introduction of the resultant labeled nucleic acids to the porous components of the device.

A 'capture oligonucleotide' or 'capture probe' is preferably immobilized to the detection strip element of the device by any of a variety of means known to those skilled in the art, such as UV irradiation. The capture probe is designed to capture the labeled nucleic acid as solution containing the labeled nucleic acid wicks through the capture zone resulting in an increased concentration of label at the site of capture probe immobilization, thus producing a detectable signal indicative of the presence of the labeled target nucleic acid amplicon(s). A single detection strip may be patterned with one or multiple capture probes to enable multiplexed detection of multiple amplicons, determination of amplicon sequence, and assay quality control (positive and negative controls).

Fluidic Subassembly Layer

Figure 7:
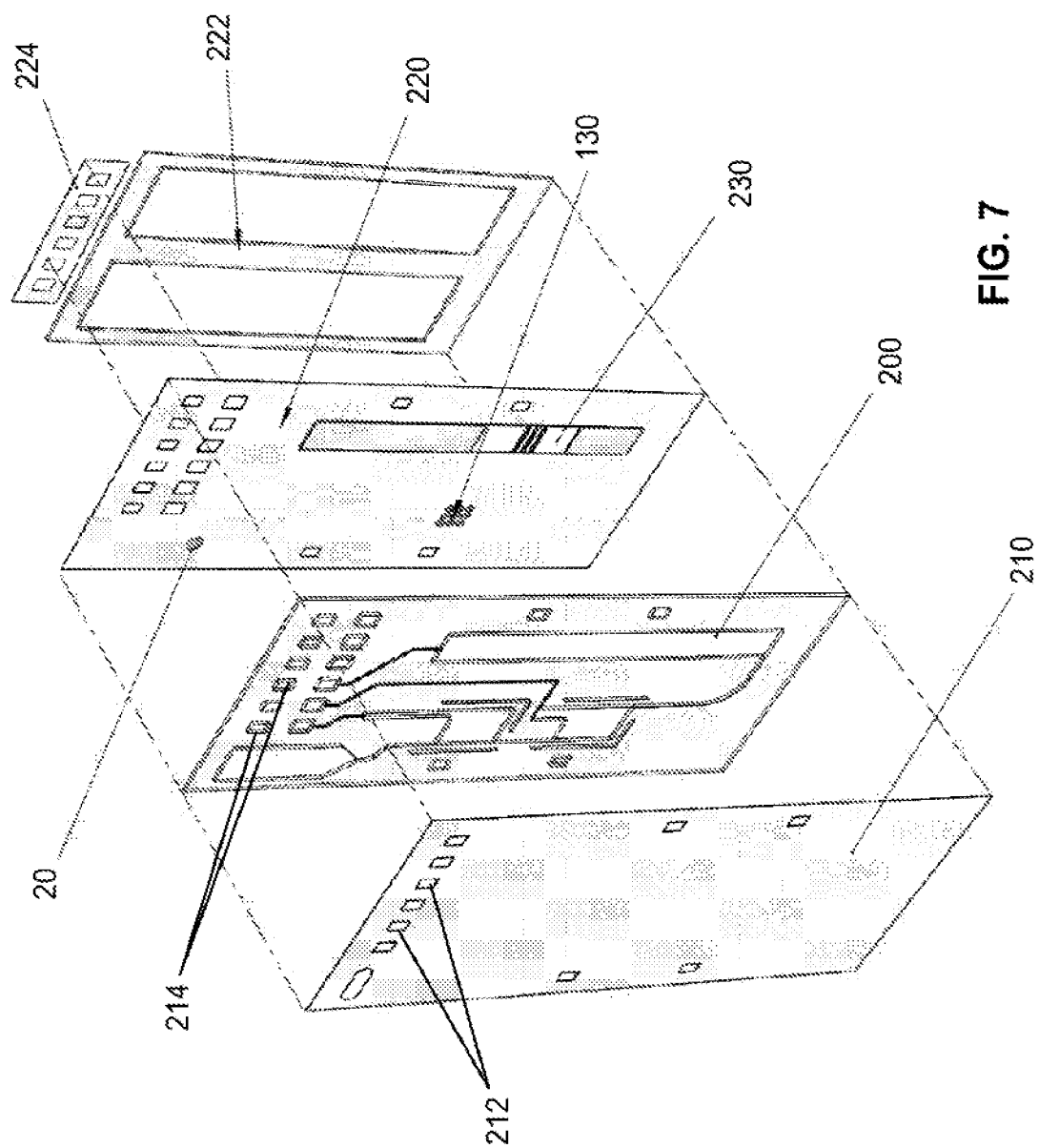
FIG. 7 shows the components of the fluidic layer of an embodiment of the present invention. A wall component of chosen thickness is bonded on two sides by face components. In one embodiment, the wall component is 0.5 mm laser cut acrylic and the faces are 0.004" polyester (PET) film. The parts are preferably bonded together with a silicone transfer adhesive. Interior surfaces are treated to control wetting. Reagents and lateral flow assembly are added during fabrication. An adhesive membrane is preferably sealed over the vent pockets.

Components of embodiments of the fluidic subassembly preferably comprise plastic, such as acrylic, polycarbonate, PETG, polystyrene, polyester, polypropylene, and/or other like materials. These materials are readily available and able to be manufactured by standard methods. As illustrated in FIGS. 3 and 7, fluidic subassemblies comprise both chambers and channels. Fluidic chambers are comprised of walls, two faces 160, and connect to one or more channels such as an inlet, an outlet, or a vent. Channels can connect two fluidic chambers, and are comprised of walls and two faces. Fluidic chamber design preferably maximizes the surface area to volume ratio to facilitate heating and cooling. The internal volume of the chamber is preferably between approximately 1 µL and approximately 50 µL. The area of chamber face 160 in contact with solution preferably corresponds with the area to which heating elements are interfaced to ensure uniform fluid temperature during heating. The shape of the fluidic chambers may be selected to mate with heating elements and to provide favorable geometries for solution ingress and egress. In some embodiments, the volume of the chamber may be larger than the fluid volume in order to provide a space for bubbles that appear during the course of device operation. Fluidic chambers may have enlarged extensions leading to vent channels, to ensure that fluid does not encroach upon the channel by capillary action or otherwise block the venting mechanism. Portions of those chambers to which vent channels communicate may optionally include one or more non-wetting or hydrophobic faces to further reduce fluid invasion into the vent channel.

In some embodiments, each fluidic subassembly comprises three laminated plastic sheets, where one component 200 forms the walls of fluidic chambers and two other face components 210, 220 are laminated to the first to form the faces. Face component 210 may optionally comprise holes 212 for viewing LED indicators 214. Face component 220 preferably comprises lyophilized reagents 20, detection particles 130, and detection strip assembly 230, and preferably interfaces with PCB 75 via adhesive shim 222, which may include membrane with adhesive border 224. In alternative embodiments, each fluidic subassembly may comprise two plastic components, where one component forms the walls and one face, and the other component is laminated to the first to seal the chamber and form the second face. In embodiments of the present invention, plastic components of the fluidic subassembly may be manufactured by means of industrial laser- or water-jet cutting, punch or stamp processes, and injection molding.

In some embodiments of the invention the thickness of the fluidic chambers and channel walls are in the range of approximately 0.025 mm to approximately 1 mm, and preferably in the range of approximately 0.1 mm to approximately 0.5 mm. This thickness preferably meets requirements of both structural integrity of the fluidic layer and to support sealing of the closed chamber under high temperatures and associated pressures. The thickness of channel walls, particularly vent channel walls, are preferably less than that of the chambers and in the range of approximately 0.025 mm to approximately 0.25 mm. The width of inlet and outlet channels is preferably chosen to enhance capillarity. A shallow vent channel imparts improved rigidity to the fluidic layer with no adverse effect on venting to atmospheric pressure. Plastic forming faces of the fluidic layer is preferably thinner than that forming the walls in order to maximize heat transfer. Optional thermal breaks 170 cut through some components of the fluidic layer and surround the amplification and detection chambers, contributing to the thermal isolation of the temperature-controlled chambers.

Plastics used in the assembly of the fluidic layer, such as acrylic and polyester, preferably comprise hydrophobic materials. In embodiments of the invention, components of the fluidic layer may be treated to enhance wettability (i.e. decrease hydrophobicity). Such treatments ensure proper fluid control in conjunction with fluidic channel dimensions. In some embodiments, a biocompatible surfactant such Triton X-100 may be applied to uncoated materials. Plasma discharge treatment is another optional treatment to alter the hydrophobicity of fluid contacting surfaces.

In some embodiments of the invention, double-sided adhesive film may be used to seal the various components of the fluidic layer. Adhesive film, such as that comprising adhesive shim 222 or membrane 224, is applied to sides of the interior component in the case of a three component fluidic layer, or to one side in the case of a two component fluidic layer. Before face component 220 is added to the other layers, additional components of the fluidic layer such as detection strip assembly 230, detection particles 130 and lyophilized reagents 20 may be incorporated. In some embodiments, the components may be laminated by applying pressure to ensure good adhesion. Adhesives known or found to negatively impact performance of nucleic acid amplification reactions must be avoided. Acrylic- or silicon-based adhesives have been successfully used in the invention. One preferred adhesive film is S17876 supplied by Advanced Adhesives Research. Other adhesives may be used if found to be chemically compatible with employed buffers, plastics and reaction chemistries while providing robust sealing over the temperatures encountered during device operation.

Referring to FIGS. 2 and 3, vent pockets are preferably differentiated from other chambers in their construction. After construction of the fluidic layer as described above, vent pockets possess an open face on the side of the fluidic layer that will meet with the PCA layer 75. To form the vent pocket, an additional plastic component is laminated to seal the chamber, preferably comprising a thin, heat labile membrane 80 with one adhesive face for application to the fluidic layer side adjacent to vent resistor 70 of the PCA. Membrane 80 comprises polyolefin of between approximately 5 μm and approximately 200 μm thickness, although other similar films may be used. This thin membrane is well suited to both seal the vent pocket and allow for easy perforation and, thus, venting to the atmosphere when current is passed through the vent resistor generating a rapid temperature increase.

Additional Components of the Fluidic Layer

As described above, several additional components are preferably incorporated within the fluidic layer of the present invention before final lamination and sealing. Reagents including buffers, salts, dNTPs, oligonucleotide primers, and enzymes such as DNA polymerase and reverse transcriptase may be lyophilized, or freeze-dried, into pellets or cakes prior device assembly. Reagent lyophilization is well known in the art and involves dehydration of frozen reagent aliquots by sublimation under an applied vacuum. By adding specific formulations of lyoprotectants such as sugars (di- and polysaccharides) and polyalcohols to the reagents prior to freezing, the activity of enzymes may be preserved and the rate of rehydration may be increased. Lyophilized reagent pellets or cakes are manufactured by standard methods and, once formed, are reasonably durable and may be easily placed into specific chambers of the fluidic layer prior to laminating the final face.

In some embodiments of the invention, detection microparticles are another additional component of the fluidic layer. In some embodiments, these microparticles may be lyophilized as described for the reaction reagents above. In other embodiments, microparticles in liquid buffer may be directly applied to an interior face of a fluidic chamber and dried before sealing. The liquid buffer containing the microparticles preferably also comprises sugars or polyalcohols that aid in rehydration. Incorporation of microparticles in aqueous buffer directly into the fluidic layer prior to drying may simplify and reduce the final cost of manufacturing, and may require heating or nucleate boiling as described above to both adequately mix the microparticles with the reaction solution, and to denature double-stranded nucleic acid product for hybridization to the detection particles.

In some embodiments of the present invention, a lateral flow detection strip assembly is also incorporated into the fluidic layer. The detection strip preferably comprises a membrane assembly comprised of at least one porous component and optionally may comprise an absorbent pad, a detection membrane, a surfactant pad, and a backing film. The detection membrane is made of nitrocellulose, cellulose, polyethersulfone, polyvinylidine fluoride, nylon, charge-modified nylon, or polytetrafluoroethylene and may be backed with a plastic film. As described above, capture probe may be deposited and irreversibly immobilized on the detection membrane in lines, spots, or any pattern that can be visualized by the unaided human eye. Deposited oligonucleotides may be permanently immobilized by UV-irradiation of the detection membrane following capture probe deposition. The surfactant pad may comprise a porous substrate, preferably with minimal nucleic acid binding and fluid retention properties, that permits unobstructed migration of the nucleic acid product and detection microparticles. The surfactant pad may comprise materials such as glass fiber, cellulose, or polyester. In embodiments of the invention, formulations including at least one amphipathic reagent are dried on the surfactant pad to allow uniform migration of sample through the detection membrane. The absorbent pad may comprise any absorbent material, and helps to induce sample wicking through the detection membrane assembly. Using an adhesive backing film, such as a double-sided adhesive film as a base, the detection membrane component is assembled by first placing the detection membrane, followed by optional absorbent pad and/or surfactant pad in physical contact with the detection membrane with between approximately 1 mm and approximately 2 mm overlap.

Electronic Subassembly Layer

In some embodiments, the printed circuit board (PCB) comprises a standard 0.062 inch thick FR4 copper clad laminate material, although other standard board materials and thicknesses may be used. Electronic components such as resistors, thermistors, LEDs, and the microcontroller preferably comprise off-the-shelf surface mount devices (SMDs) and are placed according to industry standard methodology.

In alternative embodiments, the PCA could be integrated with the cassette wall and comprise a flexible plastic circuit. Flex circuit materials such as PET and polyimide may be used. The use of flexible plastic circuitry is well known in the art. In another embodiment, heating elements and temperature sensors may be screen printed onto the plastic fluidic layer with technology developed by companies such as Soligie, Inc.

In some embodiments of the invention, the PCB thickness as well as the amount and placement of copper in regions surrounding the resistive heaters are tailored for thermal management of the reaction solution in the fluidic layer. This can be accomplished by use of standard manufacturing techniques already mentioned.

Example resistor heater assemblies are shown in FIG. 2 and FIG. 3. In some embodiments of the invention, the resistor is a thick film 2512 package, although other resistors may be used. Heating chambers in the fluidic layer are preferentially of dimensions similar to those of the resistor to ensure uniform heating throughout the chamber. A single resistor of this size is sufficient to heat approximately 15 µL of solution, assuming a fluidic layer thickness of 0.5 mm. The schematic in FIG. 3 shows two resistors 100 forming a heater sufficient to heat approximately 30 µL of solution, assuming a fluidic layer thickness of 0.5 mm. In this case, the resistors are preferably 40 ohm each and arranged in a parallel configuration.

Figure 8:
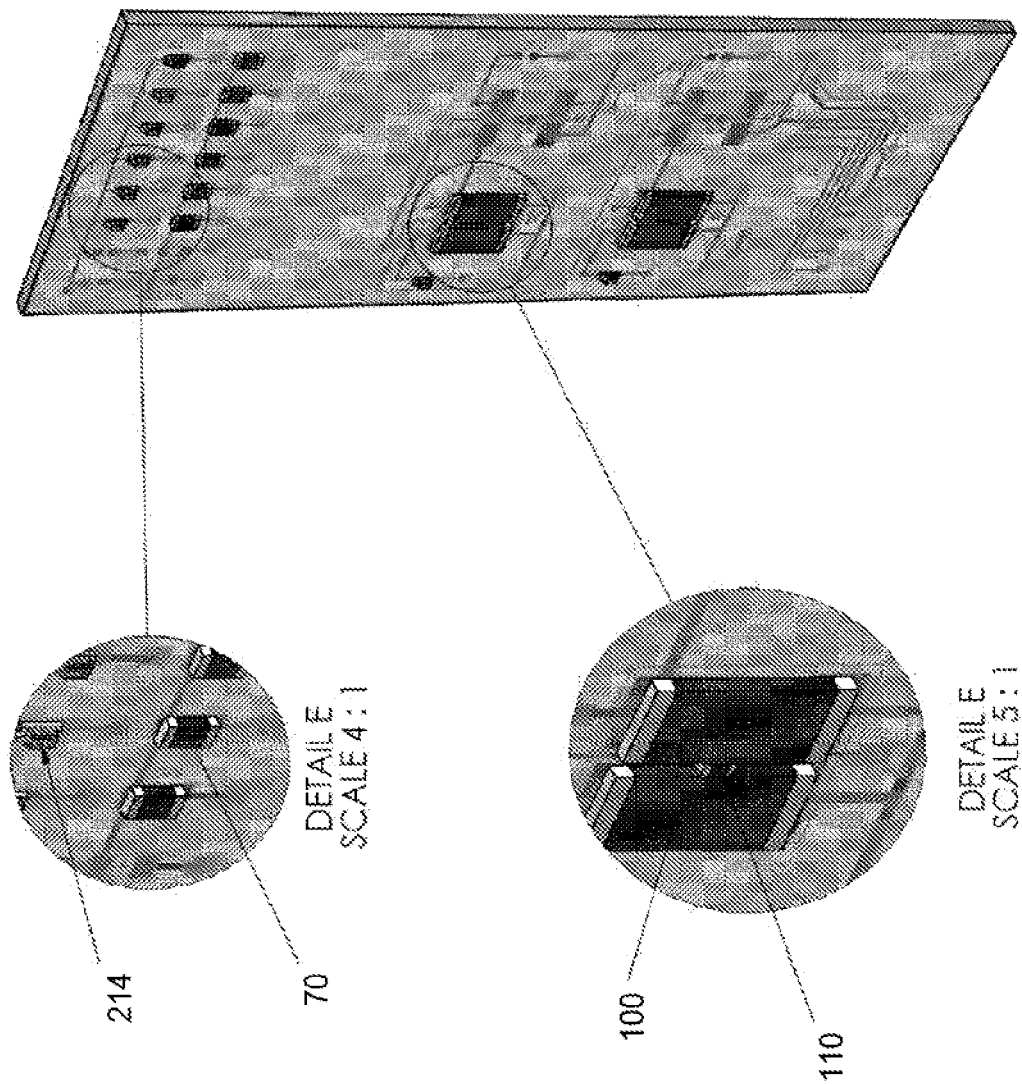
FIG. 8 shows the PCA side facing the fluidic assembly of an embodiment of the present invention in which the heating elements are thick-film resistors. The temperature sensor is a small SMD thermistor positioned in close proximity to the heaters. The PCA may optionally incorporate indicator LEDs for monitoring assay progression, heating, and vent opening.

In some embodiments of the invention, temperature sensor 110 preferably comprises a, thermistor, such as a 0402 NTC device, which has a height similar to that of the 2512 resistor package. The thermistor is preferably aligned either adjacent to or in between the resistor heaters in the case of a one resistor or two resistor set-up, respectively; see for example FIG. 8. By closely aligning these electronic elements, only a very thin air gap results between them. Furthermore, application of a thermal compound before assembling the fluidic with the electronic layer ensures good thermal contact between the fluidic layer, resistor, and thermistor.

In some embodiments of the invention, vent resistor 70 is a thick film 0805 package, although similar resistors may be used.

In some embodiments of the invention, the microcontroller is an AVR Atmega32. The microcontroller is preferably matched to the complexity of the fluidic system. For example, with multiplexing, the number of individual vents and heaters is commensurate with the number of microcontroller I/O lines. Memory size can be chosen to accommodate program size.

In certain embodiments of the invention, N-channel MOSFETs in the SOT-23 package operating in an ON-OFF mode are used to modulate current load to vent and heater resistors. Modulation signals are sent via the microcontroller. In alternative embodiments, a pulse-width-modulation scheme and/or other control algorithms could be used for more advanced thermal management of fluidics. This would typically be handled by the microcontroller and may require additional hardware and/or software features known to those skilled in the art.

Final Device Assembly

Figure 9:
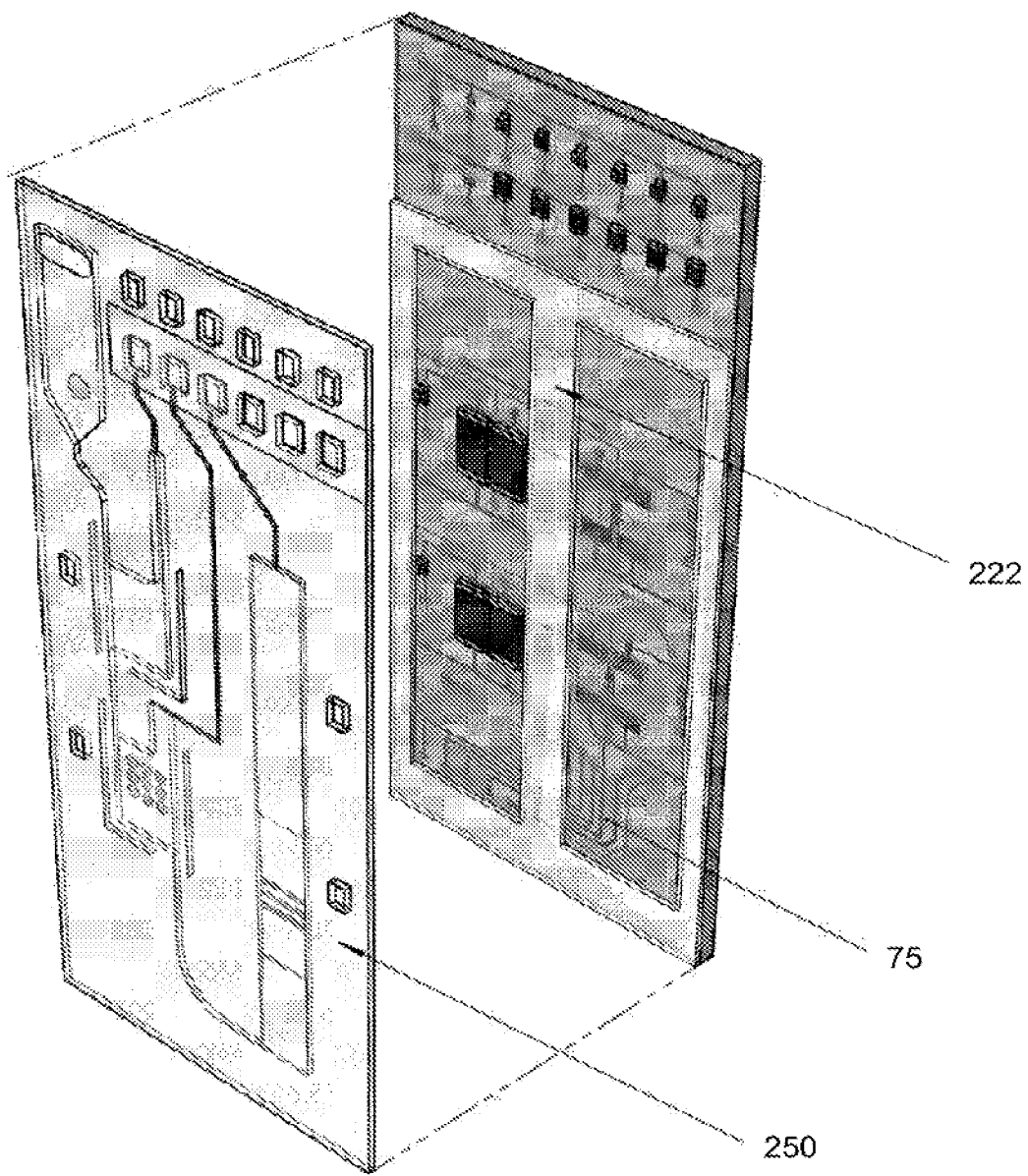
FIG. 9 is a drawing illustrating the fluid cassette bonded to the PCA with an adhesive shim in accordance with an embodiment of the present invention. The shim thickness can be important to proper distancing and function of the vents and heaters.

The final assembly of fluidic, electronic, and housing components into a finished device preferably begins by lamination of the fluidic layer(s) 250 and electronic layer 75 to ensure good thermal contact between PCA heating elements and chambers and/or pockets present in the fluidic layer. As shown in FIG. 9, adhesive shim 222 both binds the two layers together and ensures level contact between the flat fluidic layer and the topographically raised electronic components present on the PCA. Thermal compound or grease may be placed on heating elements before lamination to further improve thermal contact. After assembly of the fluidic and electronic layers, a protective plastic housing may be affixed to result in the final device.

Figure 10B:
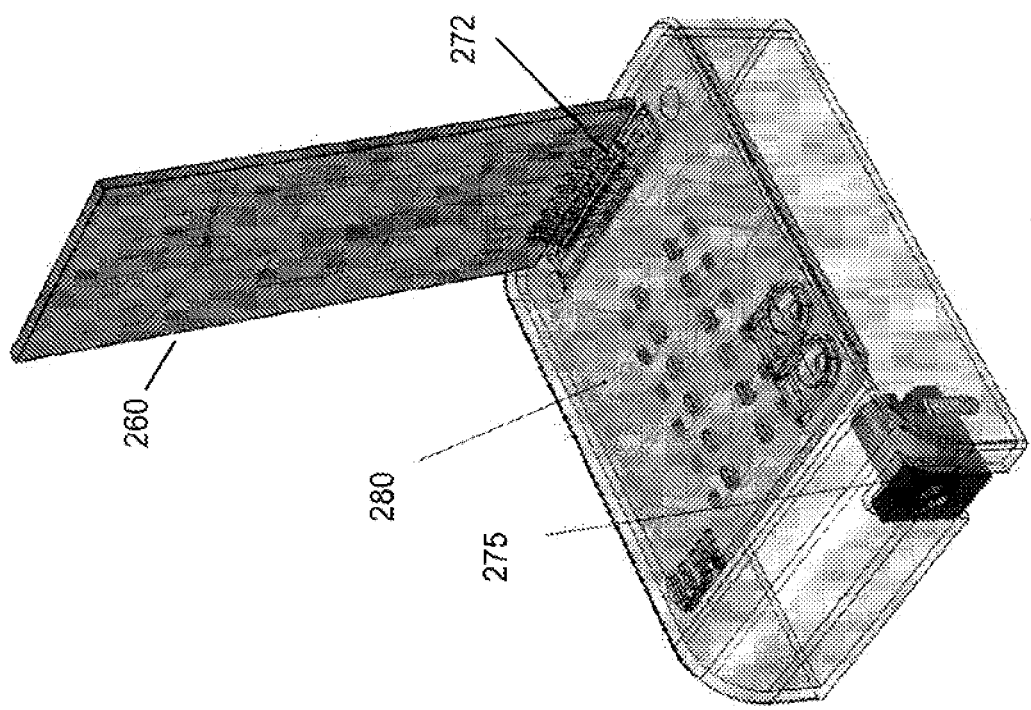
FIG. 10B shows the disposable PCA/fluidic assembly of FIG. 10A in place in a docking station. The docking station contains the control electronics and power supply and is optionally easily portable and handheld. The disposable portion containing the PCA and fluidic assemblies are inserted in the connector, preferably in a vertical orientation. A user interface including indicating LEDs, LCD, and user controls may optionally be present in some embodiments. The docking station may include buttons to initiate electronic processes required for the assay.
Figure 10A:
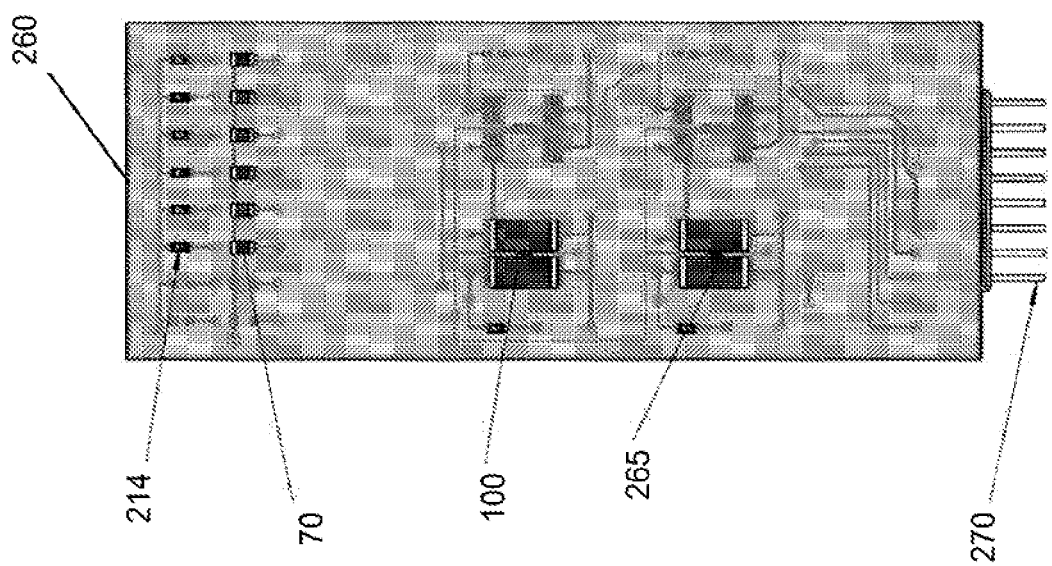
FIG. 10A shows the disposable PCA of a semi-disposable invention configuration embodiment of the present invention. The PCA contains only electronic components that interface with the disposable fluidic assembly. This includes the heating elements, temperature sensors, and optionally LED indicators. A connector is present to complete circuitry and optionally to add support in the vertical orientation.

Depending on the application, different embodiments of the invention may be of the most utility. Some embodiments comprises a device in which a small controlling base unit operates a smaller disposable unit containing the nucleic acid amplification and detection systems. This particular embodiment helps to reduce cost of an individual diagnostic test. A representative device designed for this purpose is shown in FIG. 10. As described above, the electronic functions of such a device is preferably split into two separate subassemblies. Disposable subassembly 260 comprises pin connector 270 or other similar electronic connector and the low-cost electronic components such as amplification chamber heating elements 100, labeling chamber heating elements 265, vent heating elements 70, temperature sensors such as thermistors, and optional LED indicators 214, including those components which directly interact with the fluidic system components. Connector 270 preferably provides current to the resistive heaters along with a power and signal line to the thermistor(s). Reusable subassembly or base unit 280 preferably incorporates reusable components such as the microcontroller, MOSFETs, switches, power supply or a power jack 275 and/or battery, optional cooling fan, optional user interface, and connector 272 compatible with connector 270 of disposable subassembly 260. When the subassemblies are mated via connectors 270 and 272, base unit 280 preferably supports disposable subassembly 260 in a substantially vertical or near-vertical orientation. Although a substantially vertical orientation is preferable in some of the embodiments described herein, similar results may be obtained if the device is operated at a tilt, especially if certain pathways are coated to reduce the wetting angle of solutions used.

Another embodiment comprises a device in which the entire assembly is disposable, as shown in FIG. 11. In this embodiment, there is only a single electronic assembly that is powered by 9-volt battery 305 preferably attached to the backside of the device via terminals 307, as shown in FIG. 11C. Microcontroller 300, power conditioning circuitry 302, and MOSFETs 310 are preferably also located on the back of the device, shown in FIG. 11B, whereas the opposing side, which is in contact with the fluidic layer and shown in FIG. 11A, comprises amplification chamber heating elements 100, labeling chamber heating elements 265, vent heating elements 70, and temperature sensors. The device depicted in FIG. 11 is designed to incorporate chambers and other components required to conduct two reactions amplification and labeling reactions in parallel for multiplexing applications. This particular embodiment is ideal for applications where testing is performed in remote locations. The device may alternatively be powered by a wall adaptor or another battery or batteries with sufficient capacity.

Figure 12:
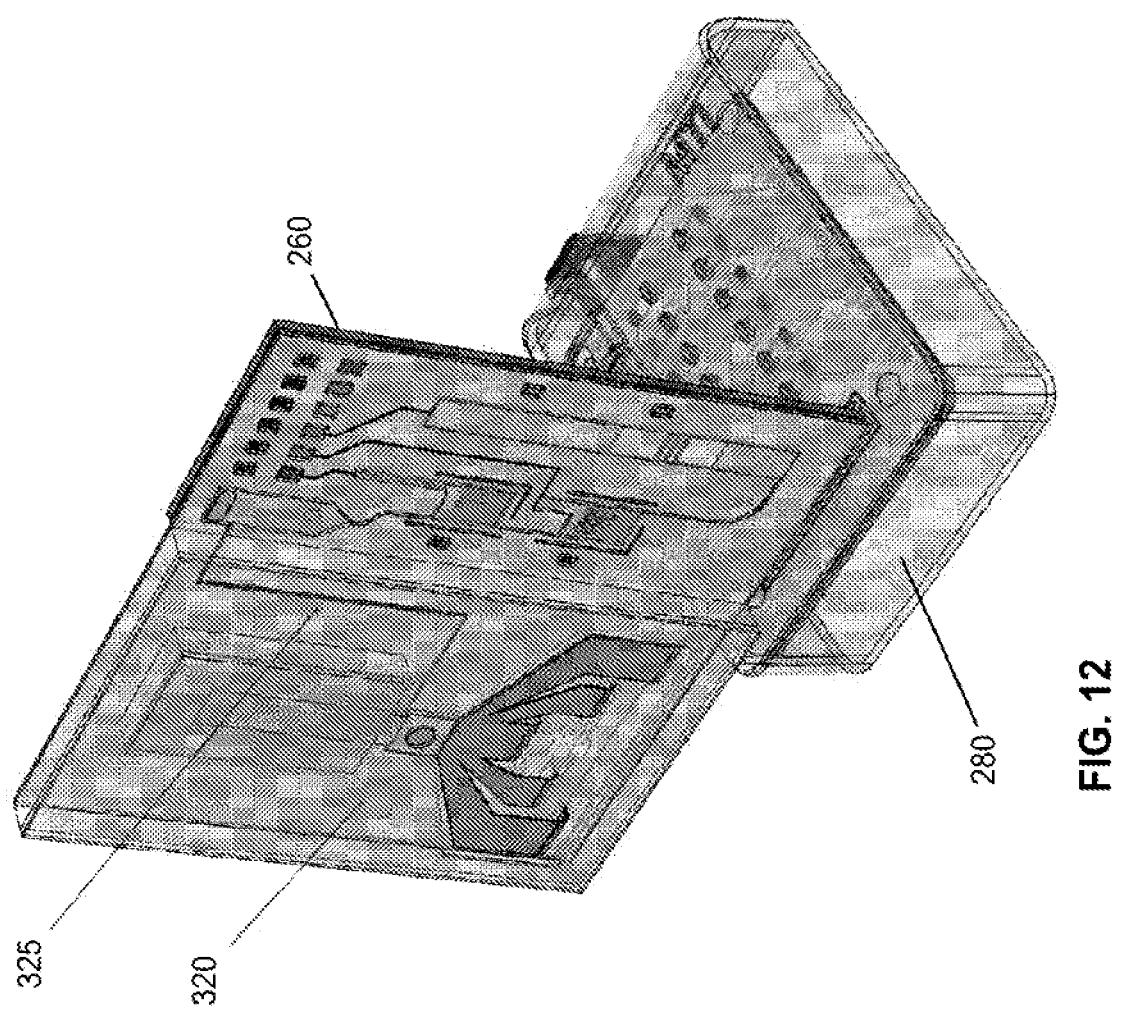
FIG. 12 is an illustration of a semi-disposable embodiment of the present invention wherein a sample preparation subsystem is interfaced with the amplification and detection fluidics and electronics.

In order to provide a complete sample-to-result molecular test, either of the above embodiments of the invention may be interfaced to a sample preparation system 320 that provides nucleic acids as output to sample chamber 10 via channel 325. This has been demonstrated using the sample preparation technology described in International Publication No. WO 2009/137059 A1, entitled "Highly Simplified Lateral Flow-Based Nucleic Acid Sample Preparation and Passive Fluid Flow Control". An embodiment of the resulting integrated device is illustrated in FIG. 12.

Fluidic Subassembly with Multiple Wall Components

In some embodiments, such as that illustrated in FIG. 7, the fluidic subassembly may comprise three laminated plastic sheets, where one sheet forms the walls of fluidic chambers and the other two components are laminated to the first to form the faces. In alternative embodiments, the fluidic subassembly may comprise two plastic components, where one component forms the walls and one face, and the other component is laminated to the first to seal the chamber and form the second face. In embodiments of the present invention, plastic components of the fluidic subassembly may be manufactured by means of industrial laser- or water-jet cutting, punch or stamp processes, and injection molding. In other alternative embodiments the fluidic subassembly may comprise laminated layers such that the detection chamber is situated in a separate layer of the device so that it is disposed in front of a layer comprising the amplification and labeling chambers. This physical configuration reduces the width of the device while also imparting additional functionality. Specifically, this embodiment places a detection strip in the detection chamber such that it is situated over the labeling chamber, allowing the heater elements underlying the labeling chamber to be used (during the detection step of an assay) for the control of temperature in the detection chamber. Control of detection chamber temperature enables the use of elevated temperatures during hybridization to the detection strip. Temperature mediated modulation of hybridization stringency during hybridization based detection can be used to achieve enhanced hybridization specificity which is of utility, for example, in the discrimination of closely related nucleic acid sequences (e.g. single nucleotide polymorphisms).

Figure 13:
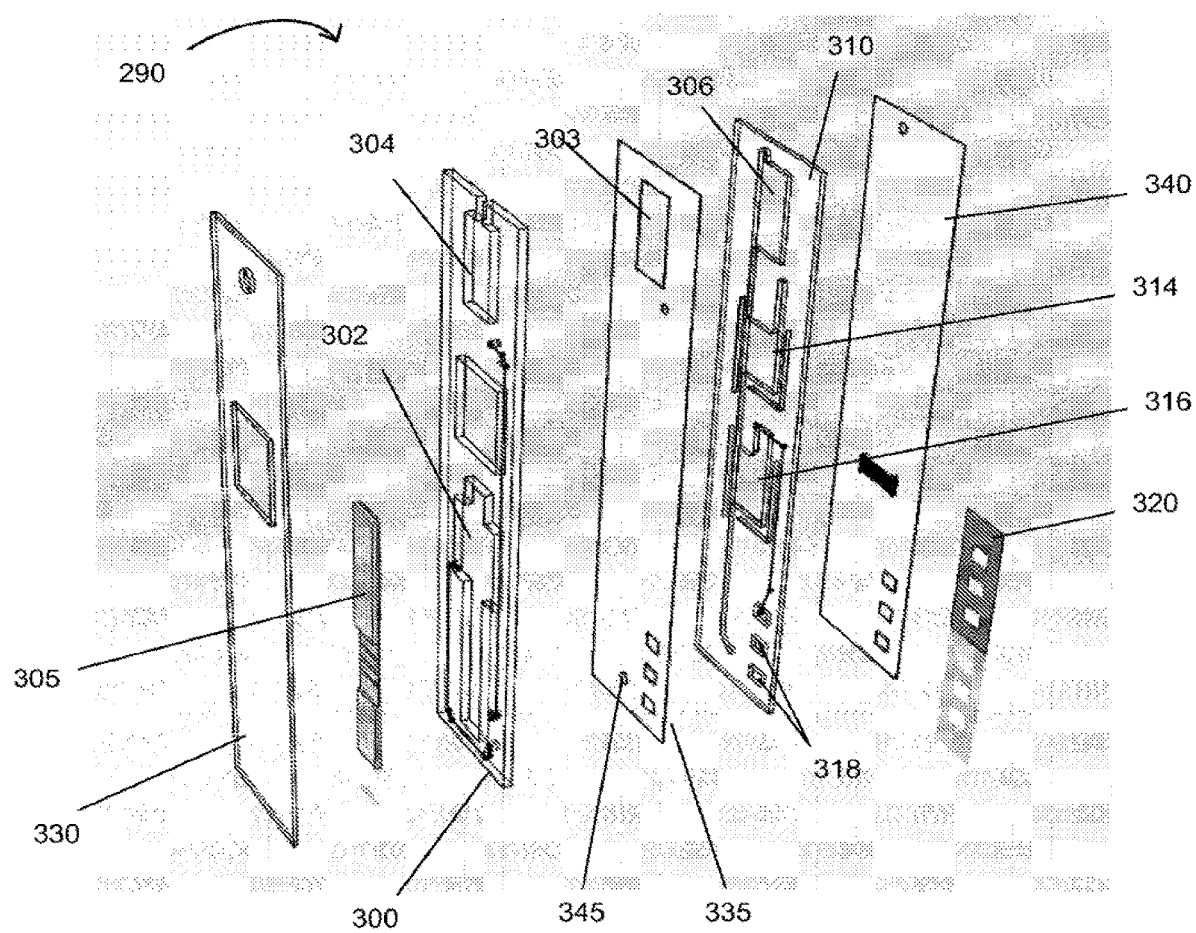
FIG. 13 shows the components of an embodiment of a multilayer fluidic layer incorporated into a disposable assay.

FIG. 13 shows the components of a multilayer fluidic cassette assembly 290 of an embodiment of the present invention such as that described immediately above. First wall component 300 comprises detection chamber 302 for accommodating detection strip 305 and portion 304 of the sample chamber. Second wall component 310 comprises another portion 306 of the sample chamber, amplification chamber 314, labeling chamber 316, vent pockets 318, and corresponding channels. Three face components 330, 335, 340 form the chambers, pockets and channels. Face component 335 acts as the rear face of wall component 300 and the front face of wall component 310 and comprises opening 303 for forming the sample chamber and opening 345 for the solution comprising labeled target nucleic acids to transfer from labeling chamber 316 to detection chamber 302. The component layers are preferably bonded together with a silicone transfer adhesive. Interior surfaces are preferably treated to control wetting. Reagents, the lateral flow assembly comprising detection strip 305, and heat-fusible thermoplastic vent valves 320 are preferably added during fabrication. An adhesive membrane is preferably sealed over the vent pockets.

Figure 14:
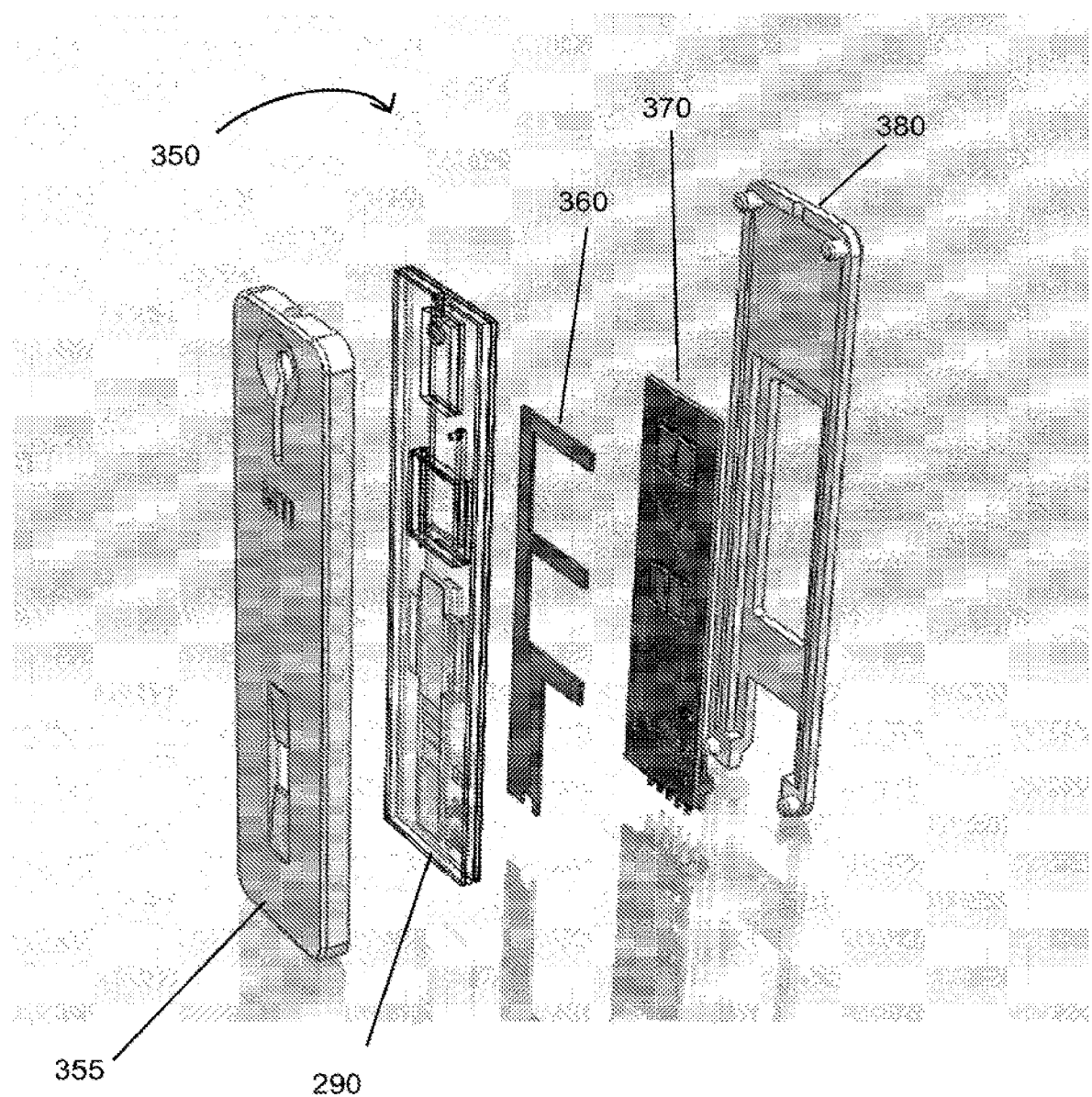
FIG. 14 shows an exploded view of a disposable assay cartridge incorporating the fluidic layer of FIG. 13.
Figure 15:
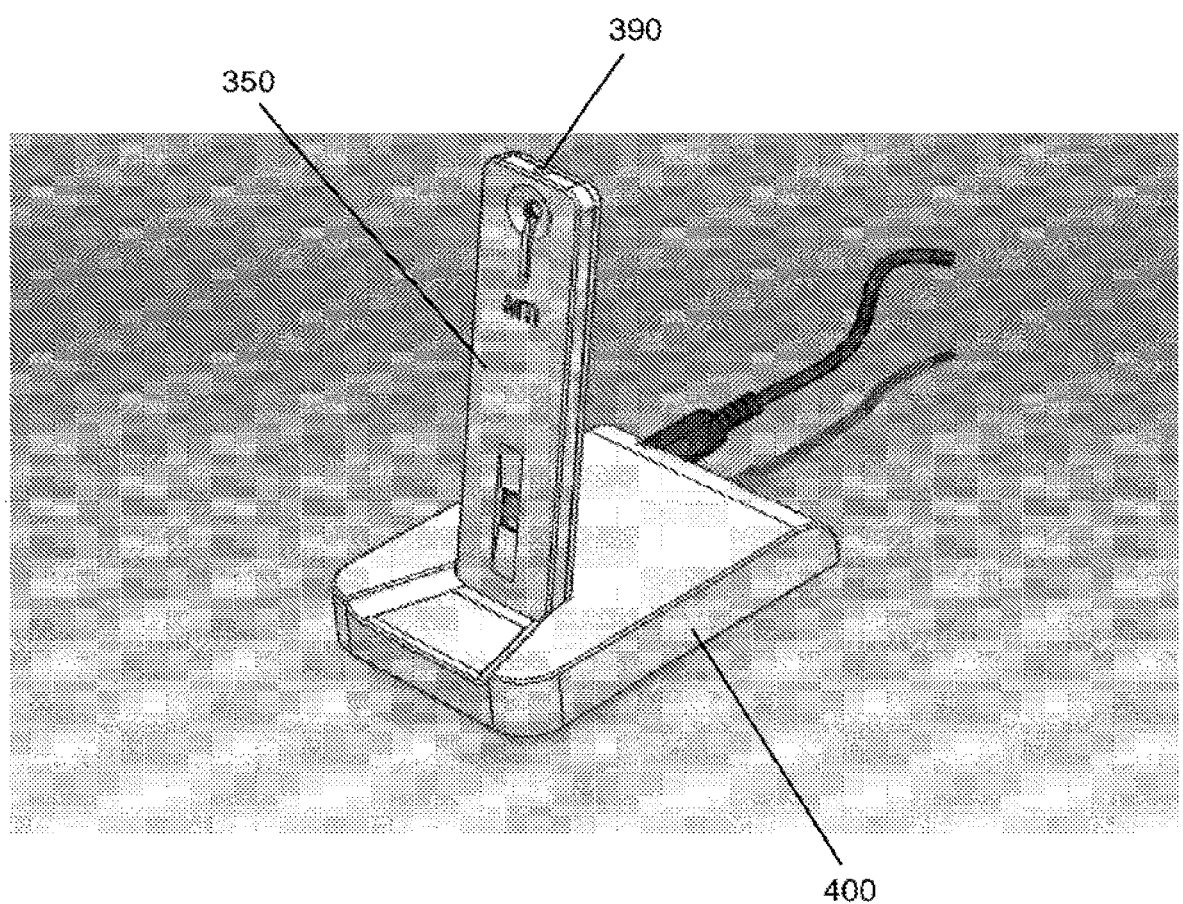
FIG. 15 is an illustration of the assembled disposable PCA/fluidic assembly of FIG. 14 in place in a docking station.

FIG. 14 shows an exploded view of a disposable assay cartridge 350 that incorporates the fluidic layer 290 of FIG. 13. Assay cartridge 350 comprises front shell, micro-fluidic cassette assembly 290, bonding tape 360, circuit board 370, and rear shell 380. FIG. 15 is an illustration of disposable PCA/fluidic assembly 350 in place in docking station 400. Sample is added to the sample chamber via sample port 390. The docking station preferably contains the control electronics and power supply and may include buttons to initiate electronic processes required for the assay.

Example 1: Method of Amplification and Detection of a Target Nucleic Acid for the Diagnosis of Candidatus Liberibacter Infection in Citrus An embodiment of the invention wherein a disposable component interfaces with a reusable dock was employed to test citrus leaf tissue for the presence of *Candidatus Liberibacter asiaticus*, the etiologic agent of citrus greening.

A partially disposable device as described above was constructed. The reusable unit comprised a standard 1.5 oz copper-clad PCB. Circuit components included an ATmega328 microcontroller, 0.5 Amp N-channel MOSFETs, SMD resistors, and power conditioning components. A stereolithography (SLA) formed plastic shell covered the board and tactile switches. A female pin connector was mounted to the top surface to allow for a vertical connection to the disposable PCA. The disposable PCA comprised a similar PCB along with thick-film resistors, 0402 thermistor, and 0603 LEDs. A right angle male pin connector was placed one end of the board to allow for vertical orientation when inserted into the female socket of the reusable unit.

The fluidic layer comprised two face components, a wall component, and a thin membrane. Face components were made from 0.004" polyester (PET). The wall components were made from 0.5 mm acrylic that was laminated with 0.002" silicone transfer film from Advanced Adhesives, Inc. The vent membrane was made with 0.0005" polyolefin with 0.004" solvent resistant acrylic adhesive from 3M, Inc. Individual components were cut to shape using a Universal Laser Systems, Inc. VersaLaser 3.5 laser cutter. Prior to assembly, all laser cut plastic fluidic components, except the membrane component, were placed in a sonicator bath containing 100 mM sodium hydroxide and 0.1% sodium dodecyl sulfate, and sonicated for 30 minutes to remove any debris, contaminating nucleic acids, or nucleases. The cleaned plastic components were finally washed with nuclease-free water. The wall and face components (PCA-oriented) were first laminated by applying 5000 psi pressure. Detection oligonucleotide conjugated polystyrene beads in 500 mM sucrose were deposited into the labeling chamber and dried under vacuum. After drying, a piece of double sided tape was placed into the detection chamber and the detection membrane component was assembled using a nitrocellulose membrane strip, an Accuflow-P surfactant pad, and blotting paper to serve as an absorbent pad. In some cases, a lyophilized bead composed of reaction enzymes and excipients, was added to the sample chamber. Finally, the fluidic layer was sealed with the other face component, and the vent membrane component was laminated to seal the vent pockets. Silicone thermal compound (Radio Shack, Inc.) was lightly applied to amplification and labeling resistors, and the fluidic and electronic layers were laminated using an adhesive shim.

Figures 16A, 16B:
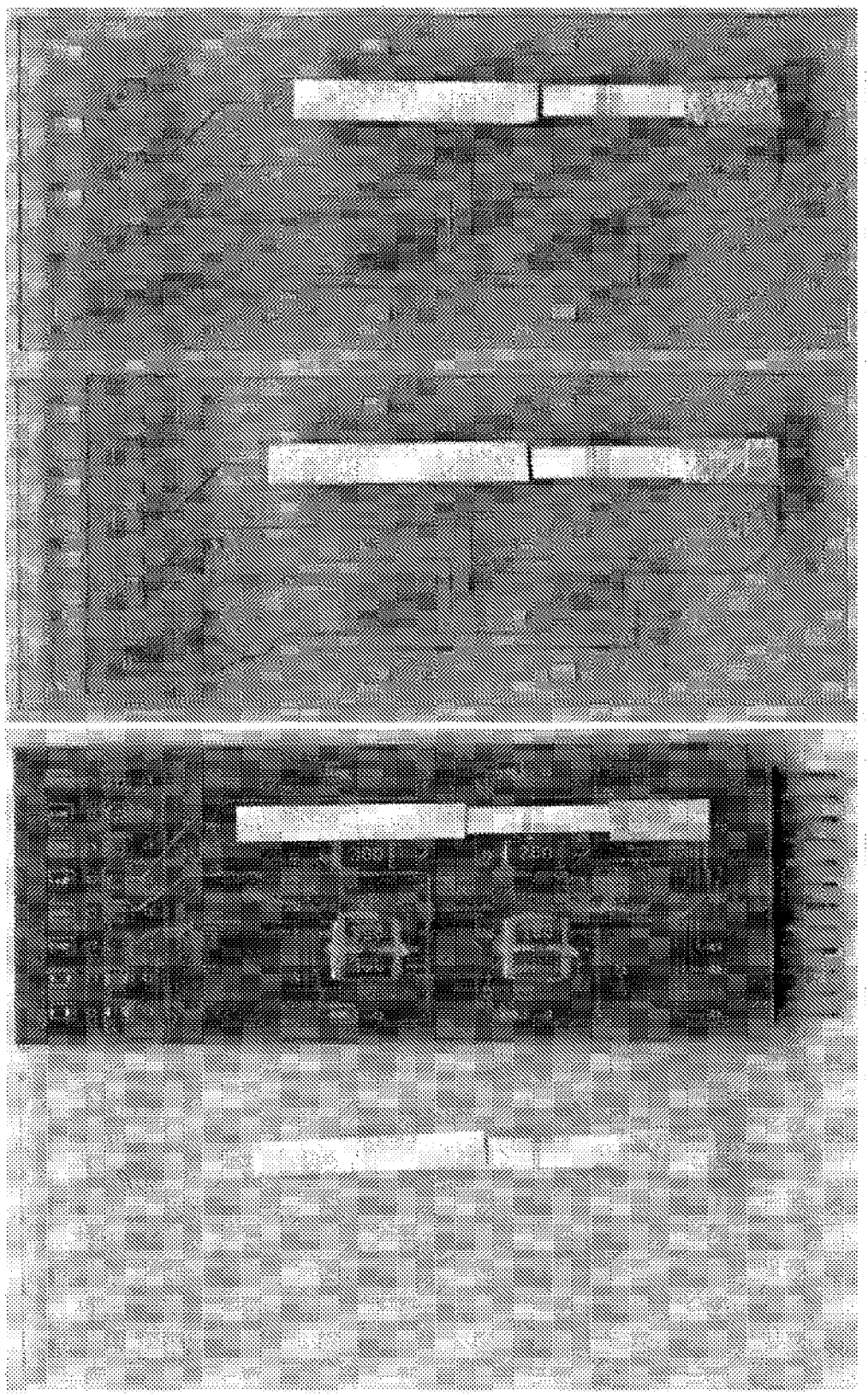
FIG. 16A-B are photographs of the fluidic layers of an embodiment of the present invention which supports thermal cycling based nucleic acid amplification and detection. A reaction solution containing all reagents necessary to support nucleic acid amplification was added to the sample chamber.
Figures 17A, 17B:
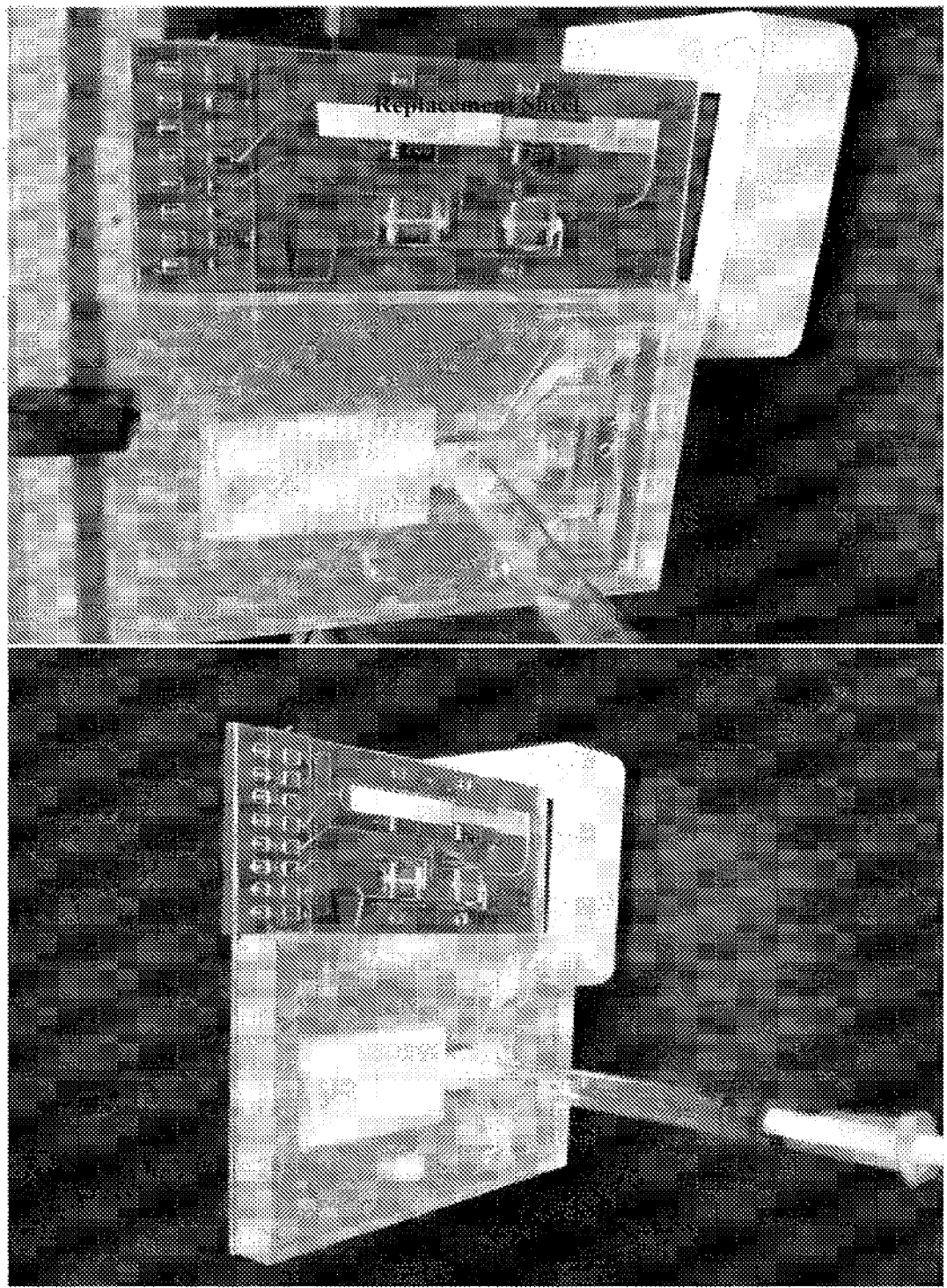
FIGS. 17A and 17B are photographs of an integrated sample-to-result nucleic acid testing device fabricated by interfacing a sample preparation sub-system with the invention. Embodiments of the present invention support nucleic acid isolation, amplification, and detection in a single integrated device. Nucleic acid isolation, amplification, and detection was performed as described in Example 2. The top line of the lateral flow assembly represents the positive control, an oligonucleotide complementary to the detection probe. The line immediately below the positive control represents the capture line, an immobilized oligonucleotide complementary to the same amplification product strand as the detection probe. The device is shown following completion of processing macerated leaf tissue from a citrus tree suffering from citrus greening disease and assaying the nucleic acids isolated by the integrated sample preparation system for *Candidatus Liberibacter* the etiologic agent of citrus greening.

After completion of device assembly, 28 µL of a reaction mixture was added to the sample chamber. Depending on the experiment, enzymes required for amplification were either added to this reaction mixture in liquid form (FIG. 16A), or present in a lyophilized cake incorporated into the sample chamber of the fluidic layer (FIG. 16B). In both cases, the nucleic acid template used was extracted from infected plant tissue using a QIAshredder and spin column kit (Qiagen, Inc.). The primers hyv1_For and hyv1_Rev were used to amplify a 139 bp nucleic acid sequence diagnostic for the presence of plant pathogenic bacteria *Candidatus Liberibacter asiaticus*. Proprietary amplification reaction chemistry was performed using a premade amplification buffer (10×) comprising 400 mM Tris-HCl (pH 8.4), 10 mM ammonium sulfate, 100 mM potassium chloride, and 0.25% Triton X-100. Each twenty µL of reaction solution contained:

9.4 µL water
2.0 µL 10× amplification Buffer
2.0 µL DMSO
0.4 µL potassium chloride (2 M)
0.5 µL magnesium chloride (100 mM)
0.5 µL dithiothreitol (100 mM)
0.5 µL dNTPs (10 mM)
2.0 µL Primer set hyv1_For and hyv1_Rev (8 µM each)
0.5 µL VentR (exo-) DNA Polymerase (2 U/µL)*
0.2 µL Et SSB, Extreme Thermostable Single Stranded Binding Protein (500 µg/mL)*
2.0 µL of DNA extracted from healthy or *C. Liberibacter* infected tissue (17.2 ng/µL)
*either included in solution, or in the case that lyophilized enzyme was used, substituted by water Venting of the amplification chamber and initiation of the amplification and detection program was accomplished by pressing a tactile switch on the reusable unit that serves as a start button. After venting, the reaction solution entered the amplification chamber where the solution was heated to 85° C. for 2 minutes, followed by 40 cycles of: 76° C. for 10 seconds and 60° C. for 25 seconds. After thermal cycling was complete, the reaction was allowed to flow into the labeling chamber by microcontroller initiated venting. The labeling chamber contained blue dyed polystyrene detection microspheres dried to one interior face of the labeling chamber in the presence of 500 mM sucrose. The detection oligonucleotide conjugated to the dyed microspheres was complementary to the sense strand of the nucleic acid amplification product. The labeling chamber was heated to 105° C. for 2 minutes and then maintained at 90° C. for 30 seconds to induce boiling and thorough mixing of the polystyrene beads and denature the double-stranded DNA product. After heating, reaction solution in the labeling chamber was allowed to cool for two minutes. The detection chamber was vented, causing the solution to flow from the labeling chamber to the detection chamber and onto the detection strip assembly. Three capture lines were immobilized on the lateral flow membrane; from the bottom of the device they were: a negative control oligonucleotide not complementary to any assayed targets; capture probe complementary to the amplification product; and a positive control oligonucleotide complementary to the detection probe. As can clearly be seen in FIG. 16A-B, the invention successfully amplified and detected the target nucleic acid with no detectable cross-hybridization to the negative control line.

The sequences of the amplification primers used were:
hyv1_For
ggccgtttta acacaaaaga tgaatatcat agatggggta gtcaa (SEQ ID NO 1)
hyv1_Rev
cggccatttt agataaatca atttgttcta gtttagatac atcaatttgt t (SEQ ID NO 2)
The sequences for capture and detection oligonucleotides used were:
Capture
tcgtttgagt agctagatcc nnnnnnnnnn nt (SEQ ID NO 3)
Detection
/5AmMC12/aattgatgga tgacgtgata gtttacgacc aacatctt/3Phos/(SEQ ID NO 4)

A more complete description of the amplification process may be found in commonly owned U.S. Provisional Patent Application Ser. No. 61/477,437, entitled "Oscillating Amplification Reaction for Nucleic Acids", incorporated herein by reference. This process enables the use of larger solution volumes with higher sensitivities, and doesn't require active cooling to perform thermal cycling. Because the process requires only passive cooling, a narrow cycling temperature range, and isn't substantially affected by looser temperature tolerances than those typically used in PCR, simple resistive heating elements may be used, thus enabling the device to be compact and inexpensive. Furthermore, superior thermal coupling is achievable because the amplification chamber is preferably flat on the side adjacent to the heating resistor, thus providing good thermal contact. This thermal interface may be enhanced by the use of a thermally conductive adhesive compound.

Example 2: Method of Isolation. Amplification, and Detection of a Target Nucleic Acid for the Diagnosis of *Candidatus Liberibacter* Infection in Citrus A partially disposable device as described above was constructed. The reusable unit comprised a standard 1.5 oz copper-clad PCB. Circuit components included an ATmega328 microcontroller, 0.5 Amp N-channel MOSFETs, SMD resistors, and power conditioning components. A stereolithography (SLA) formed plastic shell covers the board and tactile switches. A female pin connector was mounted to the top surface to allow for a vertical connection to the disposable PCA. The disposable PCA comprised a similar PCB along with thick-film resistors, 0402 thermistor, and 0603 LEDs. A right angle male pin connector was placed at one end of the board to provide vertical orientation when inserted into the female socket of the reusable unit.

The fluidic layer comprised two face components, a wall component, and a thin membrane. Face components comprised 0.004" polyester. The wall components comprised 0.5 mm acrylic that was laminated with 0.002" silicone transfer film from Advanced Adhesives, Inc. To accommodate the integration of the fluidic layer with the sample preparation sub-system, the wall and face components were fabricated to provide an opening and channel situated such that, when laminated to the sample preparation sub-system, purified nucleic acids would be communicated into the sample chamber of the invention during the elution phase of the sample preparation process. The vent membrane was made with 0.0005" polyolefin with 0.004" solvent resistant acrylic adhesive from 3M, Inc. Individual components were cut to shape using a Universal Laser Systems, Inc. VersaLaser 3.5 laser cutter. Prior to assembly, all laser cut plastic fluidic components, except the membrane component, were placed in a sonicator bath containing 100 mM sodium hydroxide and 0.1% sodiumdodecyl sulfate, and sonicated for 30 minutes to remove any debris, contaminating nucleic acids, or nucleases. The cleaned plastic components were finally washed with nuclease-free water. The wall and face components (PCA-oriented) were first laminated by applying 5000 psi pressure. Detection oligonucleotide conjugated polystyrene beads in 500 mM sucrose were deposited into the labeling chamber and dried under vacuum. After drying, a piece of double sided tape was placed into the detection chamber and the detection membrane component was assembled using a nitrocellulose membrane strip, an Accuflow-P surfactant pad, and blotting paper to serve as an absorbent pad. In some cases, a lyophilized bead composed of reaction enzymes and excipients, was added to the sample chamber. Finally, the fluidic layer was sealed with the other face component, and the vent membrane component was laminated to seal the vent pockets. Silicone thermal compound (Radio Shack, Inc.) was lightly applied to amplification and labeling resistors, and the fluidic and electronic layers were laminated using an adhesive shim.

The sample preparation sub-system, to which the fluidic layer of the invention was interfaced, was fabricated from laser cut acrylic laminated to form buffer reservoirs and physical supports for absorbent material components of the sub-system. A passive buffer exchange structure was cut in a geometry described in International Publication No. WO 2009/137059 A1, entitled "Highly Simplified Lateral Flow-Based Nucleic Acid Sample Preparation and Passive Fluid Flow Control". Nonwoven nylon was used as the buffer exchanger material. Whatman GF/B glass fiber filter was employed as the nucleic acid affinity matrix. Cotton gauze was used as an absorbent pad to provide an absorbent sink of suitable capacity.

Plant tissue, specifically four 1.5 mm biopsy punches collected from citrus leaf midrib near the petiole, was briefly ground in a microcentrifuge tube in 150 µL of extract buffer (4M guanidinium thiocyanate, 25 mM tris, pH 6.4). The resulting crude extract was introduced to the sample reservoir of the sample preparation sub-system immediately following the addition of 200 µL of wash buffer 1 (2M guanidinium thiocyanate, 30% ethanol, 25 mM tris, pH 7.4) and 800 µL wash buffer 2 (400 mM NaCl, 50% ethanol, 50 mM tris, pH 6.4) to their respective reservoirs. 15 minutes following the addition of sample, the nucleic acid binding matrix of the sample preparation component was "punched" into the underlying elution chamber and nucleic acids were eluted with 50 µL of reaction buffer. Punch-through and reaction buffer injection was accomplished by pushing a 1 cc tuberculin syringe (without needle) through the hole overlying the affinity matrix to displace the matrix into the underlying elution chamber. The elution chamber was connected to the sample chamber of the invention by a channel in the specially designed fluidic layer. Depressing the syringe plunger resulted in elution of captured nucleic acid, which flowed through said channel into the sample chamber.

With the exception of the enzymes, the elution buffer contained all reagents necessary for target amplification by a proprietary amplification technique, including the primers hyvl_For and hyvl_Rev, which selectively amplify a 139 bp sequence diagnostic for the presence of plant pathogenic bacteria *Candidatus Liberibacter asiaticus*. Amplification buffer (10×) was premade and contained 400 mM Tris-HCl (pH 8.4), 10 mM ammonium sulfate, 100 mM potassium chloride, and 0.25% Triton X-100. Twenty μL of elution buffer contained:

12.1 μL water
2.0 μL 10× amplification Buffer
2.0 μL DMSO
0.4 μL potassium chloride (2 M)
0.5 μL magnesium chloride (100 mM)
0.5 μL dithiothreitol (100 mM)
0.5 μL dNTPs (10 mM)
2.0 μL Primer set hyvl_For and hyvl_Rev (8 μM each)

Prior to energizing the device, the following enzymes were added to the eluted nucleic acid sample in the sample chamber and briefly mixed using a gel-loading pipette tip.

1.0 μL VentR (exo-) DNA Polymerase (2 U/μL)
0.4 μL Et SSB, Extreme Thermostable Single Stranded Binding Protein (500 μg/mL)

Venting of the amplification chamber and initiation of the amplification and detection program was accomplished by pressing a tactile switch on the reusable unit that serves as a start button. After venting, the reaction solution entered the amplification chamber where the solution was heated to 85° C. for 2 minutes, followed by 40 cycles of: 76° C. for 10 seconds and 60° C. for 25 seconds. After thermal cycling was complete, the reaction was allowed to flow into the labeling chamber by microcontroller initiated venting. The labeling chamber contained blue dyed polystyrene detection microspheres dried to one interior face of the labeling chamber in the presence of 500 mM sucrose. The detection oligonucleotide conjugated to the dyed microspheres was complementary to the sense strand of the nucleic acid amplification product. The labeling chamber was heated to 105° C. for 2 minutes and then maintained at 90° C. for 30 seconds to induce boiling and thorough mixing of the polystyrene beads and denature the double-stranded DNA product. After heating, reaction solution in the labeling chamber was allowed to cool for two minutes. The detection chamber was vented, causing the solution to flow from the labeling chamber to the detection chamber and onto the detection strip assembly. Three capture lines were immobilized on the lateral flow membrane, from the bottom of the device they were: A negative control oligonucleotide not complementary to any assayed targets; capture probe complementary to the amplification product; and a positive control oligonucleotide complementary to the detection probe. As can clearly be seen in FIG. 14, the fully integrated device resulted in successful nucleic acid isolation, amplification and detection of the target nucleic acid.

Example 3: Method of Amplification and Detection of a Target Nucleic Acid for the Diagnosis of *Candidatus Liberibacter* Infection in Citrus An embodiment of the invention wherein a disposable component interfaces with a reusable dock was employed to test crude citrus leaf tissue extracts for the presence of *Candidatus Liberibacter asiaticus*, the etiologic agent of citrus greening without a preceding nucleic acid isolation step.

A partially disposable device as described above was constructed. The reusable unit comprised a standard 1.5 oz copper-clad PCB. Circuit components included an ATmega328 microcontroller, 0.5 Amp N-channel MOSFETs, SMD resistors, and power conditioning components. A stereolithography (SLA) formed plastic shell covered the board and tactile switches. A female pin connector was mounted to the top surface to allow for a vertical connection to the disposable PCA. The disposable PCA comprised a similar PCB along with thick-film resistors, 0402 thermistor, and 0603 LEDs. A right angle male pin connector was placed one end of the board to allow for vertical orientation when inserted into the female socket of the reusable unit.

The fluidic layer comprised two face components, a wall component, and a thin membrane. Face components were made from 0.004" polyester. The wall components were made from 0.5 mm acrylic that was laminated with 0.002" silicone transfer film from Advanced Adhesives, Inc. The vent membrane comprised 0.0005" polyolefin with 0.004" solvent resistant acrylic adhesive from 3M, Inc. Individual components were cut to shape using a Universal Laser Systems, Inc. VersaLaser 3.5 laser cutter. Prior to assembly, all laser cut plastic fluidic components, except the membrane component, were placed in a sonicator bath containing 100 mM sodium hydroxide and 0.1% sodiumdodecyl sulfate, and sonicated for 30 minutes to remove any debris, contaminating nucleic acids, or nucleases. The cleaned plastic components were finally washed with nuclease-free water. The wall and face components (PCA-oriented) were first laminated by applying 5000 psi pressure. Detection oligonucleotide conjugated polystyrene beads in 500 mM sucrose were deposited into the labeling chamber and dried under vacuum. After drying, a piece of double sided tape was placed into the detection chamber and the detection membrane component was assembled using a nitrocellulose membrane strip, an Accuflow-P surfactant pad, and blotting paper to serve as an absorbent pad. In some cases, a lyophilized bead composed of reaction enzymes and excipients, was added to the sample chamber. Finally, the fluidic layer was sealed with the other face component, and the vent membrane component was laminated to seal the vent pockets. Silicone thermal compound (Radio Shack, Inc.) was lightly applied to amplification and labeling resistors, and the fluidic and electronic layers were laminated using an adhesive shim.

After completion of device assembly, 40 μL of a reaction mixture was added to the sample chamber. Depending on the experiment, enzymes required for amplification were either present in this reaction mixture in liquid form, or present in a lyophilized cake incorporated into the sample chamber of the fluidic layer. In both cases, the assayed specimen was comprised of 4 μL of crude citrus tissue extract prepared by crushing 5 biopsy punches of 1.5 mm diameter in 500 μL of nuclease free water. The primers hyvl_For and hyvl_Rev were used to amplify a 139 bp nucleic acid sequence diagnostic for the presence of plant pathogenic bacteria *Candidatus Liberibacter asiaticus*. Proprietary amplification reaction chemistry was performed. Amplification buffer (10×) was premade and contained 400 mM Tris-HCl (pH 8.4), 10 mM ammonium sulfate, 100 mM potassium chloride, and 0.25% Triton X-100. Each fourty μL of reaction solution contained:

18.8 μL water
4.0 μL 10× amplification buffer
4.0 μL DMSO
0.8 μL potassium chloride (2 M)
1.0 μL magnesium chloride (100 mM)
1.0 μL dithiothreitol (100 mM)
1.0 μL dNTPs (10 mM)
4.0 μL Primer set hyvl_For and hyvl_Rev (8 μM each)
1.0 μL VentR (exo-) DNA Polymerase (2 U/μL)*
0.4 μL Et SSB, Extreme Thermostable Single Stranded Binding Protein (500 μg/mL)*
4.0 μL of citrus tissue extract generated by briefly crushing 5 biopsy punches (1.5 mm diameter obtained from citrus leaf petiole or the midrib proximal to the petiole of either healthy or *C. Liberibacter* infected citrus trees) or a ~4 mm length of petiole tissue in 500 μL of nuclease free water

*either included in solution, or in the case that lyophilized enzyme was used, substituted by water Venting of the amplification chamber and initiation of the amplification and detection program was accomplished by pressing a tactile switch on the reusable unit that serves as a start button. After venting, the reaction solution entered the amplification chamber where the solution was heated to 85° C. for 2 minutes, followed by 40 cycles of: 76° C. for 10 seconds and 60° C. for 25 seconds. After thermal cycling was complete, the reaction was allowed to flow into the labeling chamber by microcontroller-initiated venting. The labeling chamber contained blue dyed polystyrene detection microspheres dried to one interior face of the labeling chamber in the presence of 500 mM sucrose. The detection oligonucleotide conjugated to the dyed microspheres was complementary to the sense strand of the nucleic acid amplification product. The labeling chamber was heated to 105° C. for 2 minutes and then maintained at 90° C. for 30 seconds to induce boiling and thorough mixing of the polystyrene beads and denature the double-stranded DNA product. After heating, reaction solution in the labeling chamber was allowed to cool for two minutes. The detection chamber was vented, causing the solution to flow from the labeling chamber to the detection chamber and onto the detection strip assembly. Three capture lines were immobilized on the lateral flow membrane, from the bottom of the device they were: A negative control oligonucleotide not complementary to any assayed targets; capture probe complementary to the amplification product; and a positive control oligonucleotide complementary to the detection probe. The invention successfully amplified and detected the target nucleic acid with no detectable cross-hybridization to the negative control lines of the detection strip.

Example 4: Method of Amplification and Detection of a Target Nucleic Acid for the Detection of *Candidatus Liberibacter* in the Asian Citrus Psyllid *Diaphorina citri Kuwayama*

An embodiment of the invention wherein a disposable component interfaces with a reusable dock was fabricated as described in Example 3 and employed to test crude whole insect extracts prepared from *Diaphorina citri Kuwayama* for the presence of *Candidatus Liberibacter asiaticus*, the etiologic agent of citrus greening without a preceding nucleic acid isolation step.

In some cases, a lyophilized bead composed of reaction enzymes and excipients, was added to the sample chamber. After completion of device assembly, 40 μL of a reaction mixture was added to the sample chamber. Depending on the experiment, enzymes required for amplification were either present in this reaction mixture in liquid form, or present in a lyophilized cake incorporated into the sample chamber of the fluidic layer. In both cases, the sample was comprised of 4 µL of a solution prepared by crushing 5 whole live *Diaphorina citri* Kuwavama in 500 µL of nuclease free water. The primers hyvl_For and hyvl_Rev were used to amplify a 139 bp nucleic acid sequence diagnostic for the presence of plant pathogenic bacteria *Candidatus Liberibacter asiaticus*. Proprietary amplification reaction chemistry was performed. Amplification buffer (10×) was premade and contained 400 mM Tris-HCl (pH 8.4), 10 mM ammonium sulfate, 100 mM potassium chloride, and 0.25% Triton X-100. Each fourty µL of reaction solution contained:

18.8 µL water
4.0 µL 10× amplification buffer
4.0 µL DMSO
0.8 µL potassium chloride (2 M)
1.0 µL magnesium chloride (100 mM)
1.0 µL dithiothreitol (100 mM)
1.0 µL dNTPs (10 mM)
4.0 µL Primer set hyvl_For and hyvl_Rev (8 µM each)
1.0 µL VentR (exo-) DNA Polymerase (2 U/µL)*
0.4 µL Et SSB, Extreme Thermostable Single Stranded Binding Protein (500 µg/mL)*
4.0 µL of whole *Diaphorina citri Kuwayama* extract generated by briefly crushing 5 whole insects in 500 μL of nuclease free water

*either included in solution, or in the case that lyophilized enzyme was used, substituted by water Venting of the amplification chamber and initiation of the amplification and detection program was accomplished by pressing a tactile switch on the reusable unit that serves as a start button. After venting, the reaction solution entered the amplification chamber where the solution was heated to 85° C. for 2 minutes, followed by 40 cycles of: 76° C. for 10 seconds and 60° C. for 25 seconds. After thermal cycling was complete, the reaction was allowed to flow into the labeling chamber by microcontroller-initiated venting. The labeling chamber contained blue dyed polystyrene detection microspheres dried to one interior face of the labeling chamber in the presence of 500 mM sucrose. The detection oligonucleotide conjugated to the dyed microspheres was complementary to the sense strand of the nucleic acid amplification product. The labeling chamber was heated to 105° C. for 2 minutes and then maintained at 90° C. for 30 seconds to induce boiling and thorough mixing of the polystyrene beads and denature the double-stranded DNA product. After heating, reaction solution in the labeling chamber was allowed to cool for two minutes. The detection chamber was vented, causing the solution to flow from the labeling chamber to the detection chamber and onto the detection strip assembly. Three capture lines were immobilized on the lateral flow membrane, from the bottom of the device they were: A negative control oligonucleotide not complementary to any assayed targets; capture probe complementary to the amplification product; and a positive control oligonucleotide complementary to the detection probe. The invention successfully amplified and detected the target nucleic acid with no detectable cross-hybridization to the negative control lines of the detection strip.

Example 5: Method of Amplification and Detection of a Target Nucleic Acid for the Detection of *Candidatus Liberibacter* in Periwinkle (*Catharanthus roseus*)

An embodiment of the invention wherein a disposable component interfaces with a reusable dock was fabricated as described in Example 3 and employed to test crude periwinkle (*Catharanthus roseus*) tissue extracts for the presence of *Candidatus Liberibacter asiaticus*, the etiologic agent of citrus greening without a preceding nucleic acid isolation step.

In some cases, a lyophilized bead composed of reaction enzymes and excipients, was added to the sample chamber. After completion of device assembly, 40 μL of a reaction mixture was added to the sample chamber. Depending on the experiment, enzymes required for amplification were either present in this reaction mixture in liquid form, or present in a lyophilized cake incorporated into the sample chamber of the fluidic layer. In both cases, the sample was comprised of 4 μL of a solution prepared by crushing 5 biopsy punches of 1.5 mm diameter each in 500 μL of nuclease free water. Biopsy punches were obtained from either *Candidatus Liberibacter asiaticus* infected or uninfected periwinkle (*Catharanthus roseus*). The primers hyvl_For and hyvl_Rev were used to amplify a 139 bp nucleic acid sequence diagnostic for the presence of plant pathogenic bacteria *Candidatus Liberibacter asiaticus*. Proprietary amplification reaction chemistry was performed. Amplification buffer (10×) was premade and contained 400 mM Tris-HCl (pH 8.4), 10 mM ammonium sulfate, 100 mM potassium chloride, and 0.25% Triton X-100. Each fourty μL of reaction solution contained:

18.8 μL water
4.0 μL 10× amplification buffer
4.0 μL DMSO
0.8 μL potassium chloride (2 M)
1.0 μL magnesium chloride (100 mM)
1.0 μL dithiothreitol (100 mM)
1.0 μL dNTPs (10 mM)
4.0 μL Primer set hyvl_For and hyvl_Rev (8 μM each)
1.0 μL VentR (exo-) DNA Polymerase (2 U/μL)*
0.4 μL Et SSB, Extreme Thermostable Single Stranded Binding Protein (500 μg/mL)*
4.0 μL of periwinkle tissue extract generated by briefly crushing 5 biopsy punches of 1.5 mm diameter (taken from the petiole of a periwinkle leaf) in 500 μL of nuclease free water

*either included in solution, or in the case that lyophilized enzyme was used, substituted by water Venting of the amplification chamber and initiation of the amplification and detection program was accomplished by pressing a tactile switch on the reusable unit that serves as a start button. After venting, the reaction solution entered the amplification chamber where the solution was heated to 85° C. for 2 minutes, followed by 40 cycles of: 76° C. for 10 seconds and 60° C. for 25 seconds. After thermal cycling was complete, the reaction was allowed to flow into the labeling chamber by microcontroller-initiated venting. The labeling chamber contained blue dyed polystyrene detection microspheres dried to one interior face of the labeling chamber in the presence of 500 mM sucrose. The detection oligonucleotide conjugated to the dyed microspheres was complementary to the sense strand of the nucleic acid amplification product. The labeling chamber was heated to 105° C. for 2 minutes and then maintained at 90° C. for 30 seconds to induce boiling and thorough mixing of the polystyrene beads and denature the double-stranded DNA product. After heating, reaction solution in the labeling chamber was allowed to cool for two minutes. The detection chamber was vented, causing the solution to flow from the labeling chamber to the detection chamber and onto the detection strip assembly. Three capture lines were immobilized on the lateral flow membrane, from the bottom of the device they were: A negative control oligonucleotide not complementary to any assayed targets; capture probe complementary to the amplification product; and a positive control oligonucleotide complementary to the detection probe. The invention successfully amplified and detected the target nucleic acid with no detectable cross-hybridization to the negative control lines of the detection strip.

Example 6: Method of Amplification and Detection of a Target Nucleic Acid for the Detection of *Candidatus Liberibacter Asiaticus* in Dodder (*Cuscuta pentagona*)

An embodiment of the invention wherein a disposable component interfaces with a reusable dock was fabricated as described in Example 3 and employed to test crude periwinkle (*Catharanthus roseus*) tissue extracts for the presence of *Candidatus Liberibacter asiaticus*, the etiologic agent of citrus greening without a preceding nucleic acid isolation step.

In some cases, a lyophilized bead composed of reaction enzymes and excipients, was added to the sample chamber. After completion of device assembly, 40 µL of a reaction mixture was added to the sample chamber. Depending on the experiment, enzymes required for amplification were either present in this reaction mixture in liquid form, or present in a lyophilized cake incorporated into the sample chamber of the fluidic layer. In both cases, the sample was comprised of 4 µL of a solution prepared by crushing a 1 cm length of dodder (*Cuscuta pentagona*) vine in 500 µL of nuclease free water. The primers hyv1_For and hyv1_Rev were used to amplify a 139 bp nucleic acid sequence diagnostic for the presence of plant pathogenic bacteria *Candidatus Liberibacter asiaticus*. Proprietary amplification reaction chemistry was performed. Amplification buffer (10×) was premade and contained 400 mM Tris-HCl (pH 8.4), 10 mM ammonium sulfate, 100 mM potassium chloride, and 0.25% Triton X-100. Each fourty µL of reaction solution contained:

18.8 µL water
4.0 µL 10× amplification buffer
4.0 µL DMSO
0.8 µL potassium chloride (2 M)
1.0 µL magnesium chloride (100 mM)
1.0 µL dithiothreitol (100 mM)
1.0 µL dNTPs (10 mM)
4.0 µL Primer set hyv1_For and hyv1_Rev (8 µM each)
1.0 µL VentR (exo-) DNA Polymerase (2 U/µL)*
0.4 µL Et SSB, Extreme Thermostable Single Stranded Binding Protein (500 µg/mL)*
4.0 µL of *Cuscuta pentagona* extract generated by briefly crushing a 1 cm length of vine in 500 µL of nuclease free water.

Although the invention has been described in detail with particular reference to the described embodiments, other embodiments can achieve the same results. Variations and modifications of the present invention will be obvious to those skilled in the art and it is intended to cover all such modifications and equivalents. The entire disclosures of all patents and publications cited above are hereby incorporated by reference.

What is claimed is:

1. A disposable platform, comprising:
a sample chamber for receiving a sample comprising a target nucleic acid;
a first vent pocket;
an amplification chamber;
the amplification chamber being connected to said sample chamber and the amplification chamber being connected to the first vent pocket;
a further chamber connected to said amplification chamber; and
one or more resistive heating elements,
the first vent pocket being sealed by a heat labile membrane, and the one or more resistive heating elements being operable to effect disruption of the heat labile membrane and to place the amplification chamber into fluid communication with a volume exterior to the first vent pocket.

2. The disposable platform of claim 1, further comprising a sample preparation stage comprising an output in fluid connection with said sample chamber.

3. The disposable platform of claim 1, wherein the amplification chamber defines a substantially flat surface having dimensions, wherein a resistive heating element is in thermal contact with the amplification chamber and defines a substantially flat surface having dimensions, and wherein the dimensions of the substantially flat surface of the amplification chamber are approximately the same as the dimensions of the substantially flat surface of the resistive heating element.

4. The disposable platform of claim 1, wherein said amplification chamber is not cooled by an active cooling device.

5. The disposable platform of claim 1, wherein (i) the amplification chamber contains an amplification solution, (ii) wherein the sample chamber comprises a liquid amplification reagent mix or a lyophilized amplification reagent mix, (iii) wherein said further chamber comprises detection particles, or any combination thereof.

6. The disposable platform of claim 1, wherein said further chamber is heatable using one of said resistive heating elements.

7. The disposable platform of claim 1, further comprising a detection subsystem that comprises a lateral flow strip.

8. The disposable platform of claim 1, wherein said sample chamber, said amplification chamber, said further chamber, and said first vent pocket are comprised in a fluid assembly layer and said one or more resistive heating elements are comprised in a separate layer comprising a printed circuit board, said separate layer being bonded to said fluid assembly layer.

9. The disposable platform of claim 8, further comprising a detection subsystem, and (i) the detection subsystem being comprised in said fluid assembly layer or (ii) the disposable platform comprising a second fluid assembly layer, the detection subsystem being comprised in said second fluid assembly layer.

10. The disposable platform of claim 1, wherein a volume of at least one of said sample chamber, said amplification chamber, and said further chamber is between approximately 1 microliter and approximately 50 microliters.

11. The disposable platform of claim 1, further comprising a connector for docking said disposable platform with a docking unit that maintains the disposable platform in a vertical or tilted orientation.

12. A method, comprising:
introducing a sample comprising nucleic acid to a sample chamber of a disposable platform;
orienting the disposable platform vertically or at a tilt;
opening a sealed vent pocket connected to an amplification chamber of the disposable platform to effect movement of the sample into the amplification chamber,
wherein the sealed vent pocket is opened by disrupting a heat labile membrane that seals the first vent pocket;
in the amplification chamber of the disposable platform, reacting the sample with a liquid or previously lyophilized amplification reagent mix to effect amplification and give rise to an amplification product that comprises amplified nucleic acid;
labeling the amplification product using detection particles; and
detecting amplified nucleic acid with a detection subsystem of the disposable platform.

13. The method of claim 12, wherein the amplification comprises heating the amplification chamber using a resistive heating element located within the disposable platform.

14. The method of claim 12, further comprising passively cooling the amplification chamber.

15. The method of claim 12, further comprising heating the labeling chamber using a resistive heating element located within the disposable platform in a vicinity of the labeling chamber.

16. The method of claim 12, further comprising controlling operation of the disposable platform by using a docking station.

17. The disposable platform of claim 1, wherein the one or more resistive heating elements are controllable by control electronics disposed in a docking station configured to receive the disposable platform.

18. The disposable platform of claim 1, wherein movement of the sample from the sample chamber to the amplification chamber is effected hydrostatically without pumping.

19. The method of claim 12, wherein the movement of the sample into the amplification chamber is effected hydrostatically without pumping.

* * * * *

SEQUENCE LISTING

```
<160> NUMBER OF SEQ ID NOS: 4

<210> SEQ ID NO 1
<211> LENGTH: 45
<212> TYPE: DNA
<213> ORGANISM: Artificial Sequence
<220> FEATURE:
<223> OTHER INFORMATION: forward primer "hyv1_For"

<400> SEQUENCE: 1
ggccgtttta acacaaaaga tgaatatcat agatggggta gtcaa              45

<210> SEQ ID NO 2
<211> LENGTH: 51
<212> TYPE: DNA
<213> ORGANISM: Artificial Sequence
<220> FEATURE:
<223> OTHER INFORMATION: reverse primer "hyv1_Rev"

<400> SEQUENCE: 2
cggccatttt agataaatca atttgttcta gtttagatac atcaatttgt t        51

<210> SEQ ID NO 3
<211> LENGTH: 32
<212> TYPE: DNA
<213> ORGANISM: Artificial Sequence
<220> FEATURE:
<223> OTHER INFORMATION: capture
<220> FEATURE:
<221> NAME/KEY: misc_feature
<222> LOCATION: (21)..(31)
<223> OTHER INFORMATION: n is a, c, g, or t

<400> SEQUENCE: 3
tcgtttgagt agctagatcc nnnnnnnnnn nt                            32
```

```
<210> SEQ ID NO 4
<211> LENGTH: 38
<212> TYPE: DNA
<213> ORGANISM: Artificial Sequence
<220> FEATURE:
<223> OTHER INFORMATION: detection

<400> SEQUENCE: 4
aattgatgga tgacgtgata gtttacgacc aacatctt                           38
```